(12) United States Patent
De Haard et al.

(10) Patent No.: US 12,240,875 B2
(45) Date of Patent: Mar. 4, 2025

(54) USE OF FCRN ANTAGONISTS FOR TREATMENT OF GENERALIZED MYASTHENIA GRAVIS

(71) Applicant: argenx BV, Ghent (BE)

(72) Inventors: Johannes De Haard, Oudelande (NL); Torsten Dreier, Sint-Martens-Latem (BE); Peter Ulrichts, Destelbergen (BE); Antonio Guglietta, Barcelona (ES); Nicolas Leupin, Zurich (CH)

(73) Assignee: argenx BV, Ghent (BE)

( * ) Notice: Subject to any disclaimer, the term of this patent is extended or adjusted under 35 U.S.C. 154(b) by 436 days.

(21) Appl. No.: 16/213,422

(22) Filed: Dec. 7, 2018

(65) Prior Publication Data

US 2019/0194277 A1    Jun. 27, 2019

Related U.S. Application Data

(60) Provisional application No. 62/596,562, filed on Dec. 8, 2017.

(51) Int. Cl.
| | | |
|---|---|---|
| A61K 39/00 | (2006.01) | |
| A61P 37/00 | (2006.01) | |
| C07K 14/47 | (2006.01) | |
| C07K 14/735 | (2006.01) | |
| C07K 16/00 | (2006.01) | |
| A61K 9/00 | (2006.01) | |
| A61K 38/00 | (2006.01) | |
| A61K 45/06 | (2006.01) | |
| A61K 47/18 | (2017.01) | |
| A61K 47/26 | (2006.01) | |

(52) U.S. Cl.
CPC .......... *C07K 14/4703* (2013.01); *A61P 37/00* (2018.01); *C07K 14/70535* (2013.01); *C07K 16/00* (2013.01); *A61K 9/0019* (2013.01); *A61K 38/00* (2013.01); *A61K 45/06* (2013.01); *A61K 47/183* (2013.01); *A61K 47/26* (2013.01); *C07K 2317/52* (2013.01); *C07K 2317/526* (2013.01); *C07K 2317/92* (2013.01); *C07K 2317/94* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,326,856 A | 7/1994 | Coughlin et al. | |
| 5,624,821 A | 4/1997 | Winter et al. | |
| 5,648,260 A | 7/1997 | Winter et al. | |
| 5,677,425 A | 10/1997 | Bodmer et al. | |
| 5,869,046 A | 2/1999 | Presta et al. | |
| 5,885,573 A | 3/1999 | Bluestone et al. | |
| 6,121,022 A | 9/2000 | Presta et al. | |
| 6,165,745 A | 12/2000 | Ward et al. | |
| 6,194,551 B1 | 2/2001 | Idusogie et al. | |
| 6,277,375 B1 | 8/2001 | Ward | |
| 6,528,624 B1 | 3/2003 | Idusogie et al. | |
| 6,737,056 B1 | 5/2004 | Presta et al. | |
| 6,821,505 B2 | 11/2004 | Ward | |
| 6,992,234 B2 | 1/2006 | Roopenian et al. | |
| 7,083,784 B2 | 8/2006 | Dall'Acqua et al. | |
| 7,183,387 B1 | 2/2007 | Presta | |
| 7,670,600 B2 | 3/2010 | Dall'Acqua et al. | |
| 7,683,784 B2 | 3/2010 | Nagai et al. | |
| 7,704,497 B2 | 4/2010 | Dall'Acqua et al. | |
| 8,012,476 B2 | 9/2011 | Dall'Acqua et al. | |
| 8,021,856 B2 | 9/2011 | Umaña et al. | |
| 8,067,232 B2 | 11/2011 | Kanda | |
| 8,101,186 B2 | 1/2012 | Mezo et al. | |
| 8,163,881 B2 | 4/2012 | Ober et al. | |
| 8,195,661 B2 | 6/2012 | Asawaree | |
| 8,216,805 B2 | 7/2012 | Carter et al. | |
| 8,273,351 B2 | 9/2012 | Tenhoor et al. | |
| 8,323,962 B2 | 12/2012 | Dall'Acqua et al. | |
| 8,475,792 B2 | 7/2013 | Dall'Acqua et al. | |
| 8,680,237 B2 | 3/2014 | Strome et al. | |
| 8,795,661 B2 | 8/2014 | Dall'Acqua et al. | |
| 8,815,246 B2 | 8/2014 | Tenhoor et al. | |
| 8,834,871 B2 | 9/2014 | Ober | |
| 9,260,520 B2 | 2/2016 | Tenhoor et al. | |
| 10,316,073 B2 * | 6/2019 | Ulrichts | ........... A61P 17/14 |
| 11,505,585 B2 | 11/2022 | Ulrichts et al. | |
| 11,591,388 B2 | 2/2023 | Borgions | |
| 2004/0002587 A1 | 1/2004 | Watkins et al. | |

(Continued)

FOREIGN PATENT DOCUMENTS

| | | |
|---|---|---|
| EP | 0227110 A2 | 7/1987 |
| EP | 0904107 B1 | 3/1999 |

(Continued)

OTHER PUBLICATIONS

Jaretzki III et al. Ann Thorac Srg 2000, 70:327-34. (Year: 2000).*
Kang et al. BioProcess International, Apr. 12, 2016, pp. 40-44. (Year: 2016).*
Anonymous: "A Study to Evaluate the Safety, Efficacy, and Pharmacokinetics of ARGX-113 in Patients with ITP", clinicaltrials.gov Identifier NCT03102593, Apr. 6, 2017, pp. 1-7.
Bussel et al., "A Randomized, Double-Blind Study of Romiplostim to Determine its Safety and Efficacy in Children with Immune Thrombocytopenia", Blood, vol. 118, No. 1, Jul. 7, 2011, pp. 28-36.

(Continued)

*Primary Examiner* — Chun W Dahle
(74) *Attorney, Agent, or Firm* — Dechert LLP; Andrew T. Wilkins; Sharla F. Flohr

(57) ABSTRACT

Provided are novel methods of treating generalized myasthenia gravis in a subject. These methods generally comprise administering to the subject an effective amount of an isolated FcRn antagonist. In certain embodiments the FcRn antagonist binds to FcRn with increased affinity and reduced pH dependence relative to native Fc region.

21 Claims, 23 Drawing Sheets
Specification includes a Sequence Listing.

(56) References Cited

U.S. PATENT DOCUMENTS

| | | | |
|---|---|---|---|
| 2004/0010124 A1 | 1/2004 | Johnson et al. | |
| 2004/0047862 A1 | 3/2004 | Lazarus et al. | |
| 2004/0265321 A1 | 12/2004 | Johnson et al. | |
| 2005/0053598 A1* | 3/2005 | Burke | A61P 1/14 424/130.1 |
| 2006/0210557 A1 | 9/2006 | Luisi et al. | |
| 2007/0041907 A1 | 2/2007 | Ober | |
| 2007/0092507 A1 | 4/2007 | Balthasar et al. | |
| 2009/0252729 A1 | 10/2009 | Farrington et al. | |
| 2011/0066111 A1 | 3/2011 | Teschner et al. | |
| 2011/0081345 A1 | 4/2011 | Moore | |
| 2011/0243966 A1 | 10/2011 | Farrington et al. | |
| 2012/0219551 A1 | 8/2012 | Johnson | |
| 2013/0142802 A1 | 6/2013 | Chang et al. | |
| 2014/0302028 A1 | 10/2014 | Zha et al. | |
| 2015/0218239 A1* | 8/2015 | Ulrichts | A61K 45/06 424/133.1 |
| 2016/0264669 A1* | 9/2016 | Ulrichts | C07K 16/00 |
| 2020/0024344 A1 | 1/2020 | de Haard et al. | |
| 2021/0236596 A1 | 8/2021 | Verheesen et al. | |
| 2022/0275035 A1 | 9/2022 | Ulrichts et al. | |
| 2023/0357382 A1 | 11/2023 | Borgions et al. | |

FOREIGN PATENT DOCUMENTS

| | | | |
|---|---|---|---|
| EP | 1355919 B1 | 11/2010 | |
| EP | 1896503 B1 | 10/2014 | |
| EP | 3087095 B1 | 8/2019 | |
| JP | 2013-507128 A | 3/2013 | |
| WO | WO 1994/029351 A2 | 12/1994 | |
| WO | WO 1996/022024 A1 | 7/1996 | |
| WO | WO 1997/034631 A1 | 9/1997 | |
| WO | WO 1999/004813 A1 | 2/1999 | |
| WO | WO 1999/058572 A1 | 11/1999 | |
| WO | WO 2000/042072 A2 | 7/2000 | |
| WO | WO 2001/058957 A1 | 8/2001 | |
| WO | WO 2002/043658 A2 | 6/2002 | |
| WO | WO 2002/060919 A2 | 8/2002 | |
| WO | WO 2004/016750 A2 | 2/2004 | |
| WO | WO 2004/029207 A2 | 4/2004 | |
| WO | WO 2004/035752 A2 | 4/2004 | |
| WO | 2004063343 A2 | 7/2004 | |
| WO | WO 2004/063351 A2 | 7/2004 | |
| WO | WO 2004/099249 A2 | 11/2004 | |
| WO | WO 2005/040217 A2 | 5/2005 | |
| WO | WO 2006/118772 A2 | 11/2006 | |
| WO | WO 2006/130834 A2 | 12/2006 | |
| WO | WO 2007/098420 A2 | 8/2007 | |
| WO | WO 2009/100105 A2 | 8/2009 | |
| WO | WO 2009/131702 A2 | 10/2009 | |
| WO | WO 2010/014909 A1 | 2/2010 | |
| WO | WO 2010/106180 A2 | 9/2010 | |
| WO | WO2010111254 A1 | 9/2010 | |
| WO | WO 2011/044368 A1 | 4/2011 | |
| WO | WO2011080209 A2 | 7/2011 | |
| WO | WO2012167039 A1 | 12/2012 | |
| WO | WO 2013/063186 A2 | 5/2013 | |
| WO | WO 2013/074598 A1 | 5/2013 | |
| WO | WO 2013/100702 A1 | 7/2013 | |
| WO | 2013166604 A1 | 11/2013 | |
| WO | 2014008391 A1 | 1/2014 | |
| WO | WO 2014/019727 A1 | 2/2014 | |
| WO | 2014140366 A1 | 9/2014 | |
| WO | WO 2014/204280 A1 | 12/2014 | |
| WO | 2015071330 A1 | 5/2015 | |
| WO | 2015073721 A1 | 5/2015 | |
| WO | WO 2015/081073 A2 | 6/2015 | |
| WO | WO 2015/100299 A1 | 7/2015 | |
| WO | WO 2016/042083 A1 | 3/2016 | |
| WO | WO 2016/123521 A2 | 8/2016 | |
| WO | WO 2016/142782 A1 | 9/2016 | |
| WO | WO 2016/180765 A1 | 11/2016 | |
| WO | WO 2016/183352 A1 | 11/2016 | |
| WO | WO 2017/012959 A1 | 1/2017 | |
| WO | WO 2017/121330 A1 | 7/2017 | |
| WO | 2017189959 A1 | 11/2017 | |
| WO | 2018023136 A1 | 2/2018 | |
| WO | WO 2018/083122 A1 | 5/2018 | |
| WO | 2019110823 A1 | 6/2019 | |
| WO | WO2019118791 A1 | 6/2019 | |
| WO | 2019234713 A2 | 12/2019 | |
| WO | 2020078905 A1 | 4/2020 | |
| WO | WO2020097099 A1 | 5/2020 | |
| WO | 2020227515 A1 | 11/2020 | |
| WO | WO2020236695 A1 | 11/2020 | |
| WO | 2020245420 A1 | 12/2020 | |
| WO | 2021022249 A1 | 2/2021 | |
| WO | 2020245420 A9 | 4/2021 | |
| WO | 2021140202 A1 | 7/2021 | |
| WO | 2021216756 A2 | 10/2021 | |
| WO | 2022098955 A1 | 5/2022 | |
| WO | 2023012515 A2 | 2/2023 | |
| WO | 2023135321 A1 | 7/2023 | |
| WO | 2023156614 A1 | 8/2023 | |
| WO | 2023209036 A1 | 11/2023 | |
| WO | 2023242361 A1 | 12/2023 | |
| WO | 2023242362 A1 | 12/2023 | |
| WO | 2023242371 A1 | 12/2023 | |
| WO | 2023242372 A1 | 12/2023 | |
| WO | 2024100453 A1 | 5/2024 | |
| WO | 2024100455 A1 | 5/2024 | |
| WO | 2024105445 A2 | 5/2024 | |
| WO | 2024147074 A1 | 7/2024 | |

OTHER PUBLICATIONS

Bussel et al., "Long-term use of the thrombopoietin-mimetic romiplostim in children with severe chronic immune thrombocytopenia (ITP): Romiplostim in Pediatric ITP" Pediatric Blood and Cancer, Feb. 1, 2015, vol. 62, No. 2, pp. 208-213.

De Haard et al., "Advancing ARGX-113 and ARGX-110 to Clinical Proof of Concept", Dec. 4, 2016, pp. 1-575.

Eddleston et al., "Blockade of the Neonatal Fc Receptor (FcRn) Represents an Effective Mechanism for the Removal of Pathogenic Autoantibodies in Primary Immune Thrombocytopenia", Database Biosis [Online] Biosciences Information Service, Philadelphia, PA, Dec. 7, 2017, XP002794883, Database accession No. PREV201900186122 abstract & BLOOD, vol. 130, No. Suppl. 1, p. 230.

International Search Report and Written Opinion in related PCT International Patent Application No. PCT/IB2019/054786, mailed Dec. 18, 2019.

International Preliminary Report on Patentability in related PCT International Patent Application No. PCT/IB2019/054786, mailed Dec. 8, 2020.

International Search Report with Written Opinion in related PCT International Patent Application No. PCT/IB2016/000398, mailed Aug. 22, 2016.

International Preliminary Report on Patentability in related PCT International Patent Application No. PCT/IB2016/000398, mailed Sep. 12, 2017.

Swiss Webster Mice, by TACONIC, Aug. 23, 2018, pp. 1-7.

Ulrichts et al., "ARGX-113, a Novel Fc-Based Approach for Antibody-Induced Pathologies Such as Primary Immune Thrombocytopenia", Blood, 2016, vol. 128, No. 22: 4919.

Abdiche et al. (2015) "The neonatal Fc receptor (FcRn) binds independently to both sites of the IgG homodimer with identical affinity," mAbs, 7(2):331-343.

Akilesh et al. (2004) "The MHC class I-like Fc receptor promotes humorally mediated autoimmune disease," J. Clin. Invest. 113(9):1328-1333.

Alegre et al. (1994) "A Non-Activating "Humanized" Anti-CD3 Monoclonal Antibody Retains Immunosuppressive Properties In Vivo," Transplantation, 57(11):1537-1543.

Alipour-Faz et al. (2017) "A comparison between IVIG and plasma exchange as preparations before thymectomy in myasthenia gravis patients," Acta Neurol Belg, 117:245-249.

(56) References Cited

OTHER PUBLICATIONS

Andersen et al. (2012) "Structure-based mutagenesis reveals the albumin-binding site of the neonatal Fc receptor," Nat. Commun. 3:610. pp. 1-9.
Anonymous (2016) "Argenx announces initial results from Phase 1 multiple ascending dose (MAD) study of ARGX-113 in healthy volunteers—Argenx," 1 pg.
ARGEN-X "ARGX-113," http://www.argen-x.com. Accessible on the Internet at URL: http://www.argen-x.com/en-GB/content/argx-113/22. [Last Accessed Jul. 5, 2017].
ARGEN-X (Oct. 2013) "An Emerging Antibody Force: Company Presentation," Presentation Slides.
ARGEN-X (Oct. 2013) "ARGX-113: Development Opportunity in Autoimmunity," Presentation Slides.
ARGEN-X N.V. (Apr. 24, 2014) "arGEN-X advances ARGX-113 into preclinical development for autoimmune disorders," Press Release. arGEN-X. Accessible on the Internet at URL: http://www.argen-x.com/en-GB/news-internal/argen-x-advances-argx-113-into-preclinical-devlopment-for-autoimmune-disorders/60. [Last Accessed Aug. 1, 2016].
ARGEN-X N.V. (Jun. 20, 2014) Prospectus for Public Offering of arGEN-X N.V.
ARGEN-X N.V. (Aug. 19, 2014) "arGEN-X announces positive preclinical results for ARGX-113," Press Release. EURONEXT. Accessible on the Internet at URL: https://www.euronext.com/nl/node/506652. [Last Accessed Aug. 1, 2016].
Armour et al. (1999) "Recombinant human IgG molecules lacking Fcgamma receptor I binding and monocyte triggering activities," Eur. J. Immunol. 29:2613-2624.
Ballow (1991) "Mechanism of action of IVIG therapy and potential uses in autoimmune connective tissue diseases," Cancer 68:1430-1436.
Barth et al. (2011) "Comparison of IVIg and PLEX in patients with myasthenia gravis," Neurology. 76(23):2017-2023.
Blanchette et al. (1984) "Intensive plasma exchange therapy in ten patients with idiopathic thrombocytopenia purpura," Transfusion. 24(5):388-394.
Burns (2012) "Of Mice and Children: Lessons From a Kawasaki Mouse Model," Circulation. 125:1480-1481.
Burns et al. (2010) "History of outcome measures for myasthenia gravis," Muscle Nerve. 42(1):5-13.
Challa (2013) "Autoantibody depletion ameliorates disease in murine experimental autoimmune encephalomyelitis," mAbs, 5(5):655-659.
Chaudhury et al. (2003) "The major histocompatibility complex-related Fc receptor for IgG (FcRn) binds albumin and prolongs its lifespan," J. Exp. Med. 197(3):315-322.
Cipriani et al. (2009) "MET as a target for treatment of chest tumor," Lung Cancer. 63(2):169-179.
Clarkson et al. (1986) "Treatment of Refractory Immune Thrombocytopeniarpura with an Anti-Fcgamma-Receptor Antibody," New England Journal of Medicine. 314(9):1236-1239.
Coetzee et al. (2000) "The Effect of Monoclonal Anti-human-platelet Antibodies on Platelet Kinetics in a Baboon Model: IgG Subclass Dependency," Thromb. Haemost. 83:148-156.
Crow et al. (2008) "The Mechanisms of Action of Intravenous Immunoglobulin and Polyclonal Anti-D Immunoglobulin in the Amelioration of Immune Thrombocytopenia Purpura: What Do We Really Know?" Transfusion Medicine Reviews. 22:103-116.
Crow et al. (2011) "The neonatal Fc receptor (FcRn) is not required for IVIg or anti-CD44 monoclonal antibody-mediated amelioration of murine immune thrombocytopenia," Blood. 118:6403-6406.
Darabi et al. (2006) "Current usage of intravenous immune globulin and the rationale behind it: the Massachusetts General Hospital data and a review of the literature," Transfusion. 46(5):741-753.
Debre et al. (1993) "Infusion of Fc gamma fragments for treatment of children with acute immune thrombocytopenia purpura," Lancet. 342(8877):945-949.

Deng et al. (2007) "Pharmacokinetic/pharmacodynamic modeling of IVIG effects in a murine model of immune thrombocytopenia," J. Pharm. Sci. 96(6):1625-1637.
Duncan et al. (1988) "Localization of the binding site for the human high-affinity Fc receptor on IgG," Nature, 332:563-564.
Edelman et al. (1969) "The covalent structure of an entire gammaG immunoglobulin molecule," The Journal of Immunology, 63:5335-5342.
El-Salem et al. (2014) "Treatment of MuSK-Associated Myasthenia Gravis," Curr. Treat. Options Neurol., 16:283, 17 pages.
Eymard et al. (2009) "[Antibodies in myasthenia gravis]," Rev. Neurol. (Paris). 165(2):137-143.
Federico et al. (2000) "Multifocal motor neuropathy improved by IVIg: randomized, double-blind, placebo-controlled study," Neurology. 55:1256-1262.
Flaherty et al. (Oct. 24, 2011) "Nonclinical evaluation of GMA161—an antihuman CD16 (FORM) monoclonal antibody for treatment of autoimmune disorders in CD16 transgenic mice," Toxicological Sciences. 125(1):299-309.
Frusho et al. (1984) "High-dose intravenous gammaglobulin for Kawasaki disease," Lancet. 2:1055-1058.
Gan et al. (2009) "Analyses of the recycling receptor, FcRn, in live cells reveal novel pathways for lysosomal delivery," Traffic. 10:600-614.
Garcia et al. (2001) "Kinetics and thermodynamics of T cell receptor-autoantigen interactions in murine experimental autoimmune encephalomyelitis," Proc. Natl. Acad. Sci. USA. 98:6818-6823.
Genbank Database [online] (Jul. 2, 2016) "*Homo sapiens* Fc fragment of IgG receptor IIIa (FCGR3A), transcript variant 1, mRNA," Accession No. NM_000569. Accessible on the Internet at URL: http://www.ncbi.nlm.nih.gov/nuccore/NM_000569. [Last Accessed Aug. 19, 2016].
Ghetie et al. (1996) "Abnormally short serum half lives of IgGs in beta2-microglobulin deficient mice," Eur. J. Immunol. 26:690-696.
Ghetie et al. (1997) "Increasing the serum persistence of an IgG fragment by random mutagenesis," Nature Biotech. 15:637-640.
Ghetie et al. (2002) "Transcytosis and catabolismof antibody," Immunol. Res. 25(2):97-113.
Gilhus et al. (2011) "Myasthenia Gravis: A Review of Available Treatment Approaches," Autoimmune Diseases, Article ID 847393, 6 pages.
Grau (Sep. 21, 2011) "IgG core a-fucosylation and its impact on FcγRIIIa binding," Roche Glycart AG. In; MipTec 2011, Basel, Switzerland.
Grevys et al. (Apr. 22, 2015) "Fc Engineering of Human IgG1 for Altered Binding to the Neonatal Fc Receptor Affects Fc Effector Functions," J Immunol. 194(11):5497-5508.
Guptill et al. (Aug. 11, 2016) "Effect of therapeutic plasma exchange on immunoglobulins in myasthenia gravis," Autoimmunity. 49(7):472-479.
Hansen et al. (2002) "Intravenous Immunoglobulin Mediates an Increase in Anti-Platelet Antibody Clearance via the FcRn Receptor," Thromb. Haemost. 88:898-899.
Hanson (2014) "The role of the immunoglobulin G1 Fc N-glycan in FcγRIIIa affinity," Thesis for partial fulfillment of the degree of Master of Science. Iowa State University. Paper 14135.
Howard et al. (Apr. 30, 2013) "A randomized, double-blind, placebo-controlled phase II study of eculizumab in patients with refractory generalized myasthenia gravis," Muscle Nerve. 48(1):76-84.
Huang et al. (2005) "The central residues of a T cell receptor sequence motif are key determinants of autoantigen recognition in murine experimental autoimmune encephalomyelitis," Eur. J. Immunol. 35:299-304.
Hutchins et al. (1995) "Improved biodistribution, tumor targeting, and reduced immunogenicity in mice with a gamma4 variant of Campath-1H," Proc. Natl. Acad. Sci., USA, 92:11980-11984.
Idusogie et al. (2000) "Mapping of the C1q Binding Site on Rituxan, a Chimeric Antibody with a Human IgG1 Fc," J. Immunol., 164:4178-4184.
Idusogie et al. (2001) "Engineered Antibodies with Increased Activity to Recruit Complement," J. Immunol., 166:2571-2575.

(56) References Cited

OTHER PUBLICATIONS

Imbach et al. (1981) "High-dose intravenous gammaglobulin for idiopathic thrombocytopeni purpura in childhood," The Lancet, 1228-1231.
Imbach et al. (1985) "Intravenous immunoglobulin versus oral corticosteroids in acute immune thrombocytopenia purpura in childhood," The Lancet, 464-468.
Imbach et al. (2009) "Intravenous immunoglobulins induce potentially synergistic immunomodulations in autoimmune disorders," Vox Sanguinis, 10 pages.
Imbach, Paul (2012) "Treatment of immune thrombocytopenia with intravenous immunoglobulin and insights for other diseases," Swiss Medical Weekly, 10 pages.
International Preliminary Report on Patentability corresponding to International Patent Application No. PCT/EP2013/068399, issued Mar. 10, 2015.
International Preliminary Report on Patentability corresponding to International Patent Application No. PCT/US2014/072087, issued Jun. 28, 2016.
International Search Report and Written Opinion corresponding to International Patent Application PCT/EP2017/077966, mailed Jan. 29, 2018.
International Search Report corresponding to International Patent Application No. PCT/EP2013/068399, mailed Apr. 9, 2014.
International Search Report with Written Opinion corresponding to International Patent Application No. PCT/US2014/072087, mailed May 12, 2015.
International Search Report with Written Opinion corresponding to International Patent Application No. PCT/EP2018/084034, mailed Feb. 18, 2019.
Jacob et al. (2012) "Presence and Pathogenic Relevance of Antibodies to Clustered Acetylcholine Receptor in Ocular and Generalized Myasthenia Gravis," Arch Neurol., 69(8):994-1001.
Jain et al. (Aug. 20, 2012) "Fully recombinant IgG2a Fc multimers (stradomers) effectively treat collagen-induced arthritis and prevent idiopathic thrombocytopenia purpura in mice," Arthritis Research & Therapy 14:R192. pp. 1-12.
Jefferis et al. (1995) "Recognition sites on human IgG for Fcgamma receptors: the role of glycosylation," Immunology Letters, 44:111-117.
Jefferis et al. (1996) "Modulation of Fc(gamma)R and human complement activation by IgG3-core oligosaccharide interactions," Immunol. Lett. 54:101-104.
Jefferis et al. (2002) "Interaction sites on human IgG-Fc for FcgammaR: current models," Immunology Letters, 82:57-65.
Junghans et al. (1996) "The protection receptor for IgG catabolismis the beta2-microglobulin-containing neonatal intestinal transport receptor," Proc. Natl. Acad. Sci. USA. 93:5512-5516.
Junghans (1997) "Finally! The Brambell receptor (FcRB). Mediator of transmission of immunity and protection from catabolismfor IgG," Immunologic Research. 16(1):29-57.
Kanda et al. (2006) "Comparison of biological activity among nonfucosylated therapeutic IgG1 antibodies with three different N-linked Fc oligosaccharides: the high-mannose, hybrid, and complex types," Glycobiol. 17(1): 104-118.
Kim et al. (1999) "Mapping of the site on human IgG1 for binding of the MHC class I related receptor, FcRn," Eur. J. Immunol. 29:2819-2825.
Law et al. (1997) "High-dose intravenous immune globulin and the response to splenectomy in patients with idiopathic thrombocytopenia purpura," N. Engl. J. Med. 336:1494-1498.
Li et al. (2005) "Complete FcRn dependence for intravenous Ig therapy in autoimmune skin blistering diseases," J. Clin. Invest. 115(12):3440-3450.
Liu et al. (2007) "Amelioration of experimental autoimmune myasthenia gravis in rats by neonatal FcR blockade," J. Immunol. 178(8):5390-5398.
Liu et al. (2009) "Comparing the Autoantibody Levels and Clinical Efficacy of Double Filtration Plasmapheresis, Immunoadsorption, and Intravenous Immunoglobulin for the Treatment of Late-Onset Myasthenia Gravis," Therapeutic Apheresis and Dialysis, 14(2):153-160.
Low et al. (2009) "Inhibitors of the FcRn:IgG Protein-Protein Interaction," AAPS Journal. 11(3):432-434.
Lund et al. (1991) "Human Fc gamma RI and Fc gamma RII interact with distinct but overlapping sites on human IgG," J. Immunol. 147:2657-2662.
Lund et al. (1992) "Multiple binding sites on the CH2 Domain of IgG for Mouse FcgammaRII," Molecular Immunology, 29(1):53-59.
Lund et al. (1995) "Oligosaccharide-protein interactions in IgG can modulate recognition by Fcgamma receptors," The FASEB Journal 9:115-119.
Lund et al. (1996) "Multiple interactions of IgG with its core oligosaccharide can modulate recognition by complement and human Fc gamma receptor I and influence the synthesis of its oligosaccharide chains," J. Immunol. 157:4963-4969.
Lutterbach et al. (2007) "Lung cancer cell lines harboring MET gene amplification are dependent on Met for growth and survival," Cancer Research. 67(5):2081-2088.
MacCallum et al. (1996) "Antibody-antigen Interactions: Contact Analysis and Binding Site Topography," J. Mol. Biol., 262:732-745.
Martin et al. (2001) "Crystal Structure at 2.8 A of an FcRn/Heterodimeric Fc Complex Mechanism of pH-Dependent Binding," Molecular Cell, 7:867-877.
Massachusetts General Hospital (Dec. 10, 2012) "Suppremol's Sm101 shows a sustained clinical activity and a favorable safety profile in primary immune thrombocytopenia (ITP) patients," Press Release. Evaluate Ltd.
Medesan et al. (1997) "Delineation of the amino acid residues involved in transcytosis and catabolismof mouse LgG," J. Immunol. 158:2211-2217.
Mendell et al. (2001) "Randomized controlled trial of IVIg in untreated chronic inflammatory demyelinating polyradiculoneuropathy," Neurology. 56:445-449.
Meriggioli et al. (2009) "Autoimmune myasthenia gravis: emerging clinical and biological heterogeneity," Lancet Neurol. 8:475-490.
Mezo et al. (2008) "Reduction of IgG in nonhuman primates by a peptide antagonist of the neonatal Fc receptor FcRn," Proc. Natl. Acad. Sci. USA. 105(7):2337-2342.
Mi et al. (2008) "Targeting the neonatal Fc receptor for antigen delivery using engineered Fc fragments," J. Immunol. 181:7550-7561.
Mohamed et al. (Jan. 7, 2013) "Massive intravascular haemolysis after high dose intravenous immunoglobulin therapy," British Journal of Haematology. 160:570.
Montoyo et al. (2009) "Conditional deletion of the MHC class I-related receptor FcRn reveals the sites of IgG homeostasis in mice," Proc. Natl. Acad. Sci. USA. 106:2788-2793.
Morea et al. (2000) "Antibody Modeling: Implications for Engineering and Design," Methods, 20:267-279.
Newburger et al. (2004) "Diagnosis, Treatment, and Long-Term Management of Kawasaki Disease: A Statement for Health Professionals From the Committee on Rheumatic Fever, Endocarditis, and Kawasaki Disease, Council on Cardiovascular Disease in the Young, American Heart Association," Pediatrics. 114:1708-1733.
Newland et al. (1983) "High-dose intravenous IgG in adults with autoimmune thrombocytopenia," The Lancet, 84-87.
Nieswandt et al. (1999) "Acute systemic reaction and lung alterations induced by an antiplatelet integrin gpIIb/IIIa antibody in mice," Blood. 94:684-693.
Niknami et al. (Jun. 2013) "Beneficial effect of a multimerized immunoglobulin Fc in an animal model of inflammatory neuropathy (experimental autoimmune neuritis)," J. Peripher. Nerv. Syst. 18(2):141-52.
Ober et al. (2004) "Exocytosis of IgG as mediated by the receptor, FcRn: an analysis at the single-molecule level," Proc. Natl. Acad. Sci. USA. 101:11076-11081.
Ober et al. (2004) "Visualizing the site and dynamics of IgG salvage by the MHC Class I-related receptor, FcRn," J. Immunol. 172:2021-2029.

(56) References Cited

OTHER PUBLICATIONS

Oshima et al. (1998) "Characterization of murine CD70 by molecular cloning and mAb," Int. Immunol. 10(4):517-526.

Patel et al. (2011) "Neonatal Fc receptor blockade by Fc engineering ameliorates arthritis in a murine model," J. Immunol. 187(2):1015-1022.

Pevzner et al. (2011) "Anti-LRP4 autoantibodies in AChR-and MuSK-antibody-negative myasthenia gravis," J. Neurol., 9 pages.

Prabhat et al. (2007) "Elucidation of intracellular recycling pathways leading to exocytosis of the Fc receptor, FcRn, by using multifocal plane microscopy," Proc. Natl. Acad. Sci. USA. 104:5889-5894.

Presta et al. (2002) "Engineering therapeutic antibodies for improved function," Biochemical Society Transactions, 30(4):487-490.

Reddy et al. (2000) "Elimination of Fc Receptor-Dependent Effector Functions of a Modified IgG4 Monoclonal Antibody to Human CD4," J. Immunol., 164:1925-1933.

Roopenian et al. (2003) "The MHC class I-like IgG receptor controls perinatal IgG transport, IgG homeostasis, and fate of IgG-Fc-coupled drugs," J. Immunology. 170:3528-3533.

Roopenian et al. (2007) "FcRn: the neonatal Fc receptor comes of age," Nat. Rev. Immunol. 7(9):715-725.

Roux et al. (1998) "Comparisons of the Ability of Human IgG3 Hinge Mutants, IgM, IgE, and IgA2, to Form Small Immune Complexes: A Role for Flexibility and Geometry," The Journal of Immunology, 4083-4090.

Schwab et al. (Mar. 2013) "Intravenous immunoglobulin therapy: how does IgG modulate the immune system?" Nat. Rev. Immunol. 176(13).

Seidling et al. (2013) "Analysis of high-dose intravenous immunoglobulin therapy in 16 patients with refractory autoimmune blistering skin disease: high efficacy and no serious adverse events," Acta Derm Venereol. 93:346-349.

Semple (2010) "Animal models of immune thrombocytopenia (ITP)," Annals of Hematology. 89:37-44.

Sesarman et al. (2010) "The neonatal Fc receptor as therapeutic target in IgG-mediated autoimmune diseases," Cell. Mol. Life Sci. 67(15):2533-2550.

Sewell: Ed. (Jan. 22, 2010) First National Immunoglobulin Database Report. Department of Health.

Shelton (1999) "Acquired myasthenia gravis: what we have learned from experimental and spontaneous animal models," Veterinary Immunology and Immunopathology. 69:239-249.

Shields et al. (2001) "High Resolution Mapping of the Binding Site on Human IgG1 for FcgammaRI, FcgammaRII, FcgammaRIII, and FcRn and Design of IgG1 Variants with Improved Binding to the FcgammaR," The Journal of Biological Chemistry, 276(9):6591-6604.

Sockolosky et al. (2015) "The neonatal Fc receptor, FcRn, as a target for drug delivery and therapy," Advanced Drug Delivery Reviews, 91:109-124.

Soliven (2012) "Autoimmune neuropathies: insights from animal models," Journal of the Peripheral Nervous System. 17:28-33.

Sorde et al. (2017) "Massive immune response against IVIg interferes with response against other antigens in mice: A new mode of action?," PLoS ONE, 12(10):e0186046, 15 pages.

Stamos et al. (2004) "Crystal structure of the HGF beta-chain in complex with the Sema domain of the Met receptor," EMBO J. 23(12):2325-2335.

Swiercz et al. (May 27, 2014) "Use of Fc-engineered antibodies as clearing agents to increase contrast during PET," J. Nucl. Med. 55:1204-1207.

Task Force of the Medical Scientific Advisory Board of the Myasthenia Gravis Foundation of America, et al. (2000) "Myasthenia gravis," Neurology, 55:16-23.

Tramontano et al. (1990) "Framework Residue 71 is a Major Determinant of the Position and Conformation of the Second Hypervariable Region in the VH Domains of Immunoglobulins," J. Mol. Biol., 215:175-182.

Ulrichts et al. (May 2017) "ARGX-113: Towards a Safe and Selective Elimination of Pathogenic Autoantibodies," 13th International Conference on Myasthenia Gravis and Related Disorders, May 15-17, 2017. New York, New York. Poster Presentation.

Ulrichts et al. (2018) "Neonatal Fc receptor antagonist efgartigimod safely and sustainably reduces IgGs in humans," J. Clin. Invest., 128(1):4372-4386.

Vaccaro et al. (2005) "Engineering the Fc region of immunoglobulin G to modulate in vivo antibody levels," Nat. Biotechnol. 23(10):1283-1288.

Vaccaro et al. (2006) "Divergent activities of an engineered antibody in murine and human systems have implications for therapeutic antibodies" Proc. Natl. Acad. Sci. USA. 103(49):18709-18714.

Van Der Meche et al. (1992) "A randomized trial comparing intravenous immune globulin and plasma exchange in Guillain-Barre syndrome. Dutch Guillain-Barre Study Group," N. Engl. J. Med. 326:1123-1129.

Wani et al. (2006) "Familial hypercatabolic hypoproteinemia caused by deficiency of the neonatal Fc receptor, FcRn, due to a mutant beta2-microglobulin gene," Proc. Natl. Acad. Sci. USA. 103(13):5084-5989.

Woods et al. (1984) "Autoantibodies against platelet glycoprotein Ib in patients with chronic immune thrombocytopeniarpura," Blood. 64:156-160.

Written Opinion corresponding to International Patent Application No. PCT/EP2013/068399, mailed Apr. 14, 2014.

Xu et al. (2000) "In Vitro Characterization of Five Humanized OKT3 Effector Function Variant Antibodies," Cellular Immunology, 200:16-26.

Yang et al., (2011) "Non-radioactive serological diagnosis of myasthenia gravis and clinical features of patients from Tianjin, China," Journal of Neurological Sciences, 301:71-76, 2011.

Ying et al. (2012) "Soluble Monomeric IgG1 Fc," The Journal of Biological Chemistry, 287(23):19399-19408.

Ying et al. (2013) "Engineered Soluble Monomeric IgG1 CH3 Domain," The Journal of Biological Chemistry, 288 (35):25154-25164.

Zhang et al. (2012) "Autoantibodies to Lipoprotein-Related Protein in Patients With Double-Seronegative Myasthenia Gravis," Arch Neurol, 69(4):445-451.

Zhou et al. (2003) "Generation of mutated variants of the human form of the MHC class I-related receptor, FcRn, with increased affinity for mouse immunoglobulin G," J. Mol. Biol. 332:901-913.

Zhou et al. (2005) "Conferring the binding properties of the mouse MHC Class I related receptor, FcRn, onto the human ortholog by sequential rounds of site-directed mutagenesis," J. Mol. Biol. 345:1071-1081.

Zinman et al. (2007) "IV immunoglobulin in patients with myasthenia gravis: a randomized controlled trial," Neurology 68:837-841.

U.S. Appl. No. 16/893,863, filed Jun. 5, 2020, Filip Borgions.

Azevedo, "argenx Doses First Subject in Study Evaluating Subcutaneous ARGX-113 for Autoimmune Diseases." Myasthenia Gravis News. 2017;1-2.

Bas Van Der Woning, "R&D Day: Fifth Efgartigimod Indication: Myositis," ARGENX, Jul. 20, 2021, pp. 23-37.

Basta and Dalakas, "High-dose intravenous immunoglobulin exerts its beneficial effect in patients with dermatomyositis by blocking endomysial deposition of activated complement fragments," J Clin Invest. 1994;94(5):1729-35.

Dalakas et al., "High-dose intravenous immune globulin for stiff-person syndrome," N Engl J Med. 2001;345(26):1870-6.

Dalakas, "Update on Intravenous Immunoglobulin in Neurology: Modulating Neuro-autoimmunity, Evolving Factors on Efficacy and Dosing and Challenges on Stopping Chronic IVIg Therapy," Neurotherapeutics. 2021;18(4):2397-2418.

Daugherty Ann L et al: "Chapter 8: Formulation and delivery issues for monoclonal antibody therapeutics", Jan. 1, 2010 (Jan. 1, 2010), Current Trends in Monoclonal Antibody Development and Manufacturing, Springer, US, pp. 103-129, XP009180430, ISBN: 978-0-387-76642-3.

(56) References Cited

OTHER PUBLICATIONS

Heo, "Efgartigimod: First Approval," Drugs. 2022;82(3):341-348.
Howard et al., "A double-blind placebo-controlled study to evaluate safety and efficacy of FcRn antagonist ARGX-113 (efgartigimod) in generalized myasthenia gravis," Elsevier 70th Annual Meeting of the American Academmy of Neurology, AAN, 2018.
Julien et al., "Abstract No. L10 Efgartigimod Prevents Necrosis and Allows for Muscle Fiber Regeneration in a Humanized Mouse Model of Immune-mediated Necrotizing Myopathy (IMNM)," ACR Meeting Abstracts, ACR Conference 2022, Oct. 18, 2022, pp. 1-4.
Kiessling, "Safety, Pharmacokinetics and Pharmacodynamics of the FCRN Inhibitor UCB7665: A Phase I Study," Journal of the Peripheral Nervous System. 2017;22(3):226-414.
Miyagawa, "Idiopathic Thrombocytopenia Purpura," Mebio. 2017;34(6):102-107.
PCT Search Report and Written Opinion for PCT/EP2023/054065, mailed May 3, 2023.
Verschuuren, "A double-blind placebocontrolled study to evaluate safety and efficacy of forn antagonist ARGX-113 in generalized MG," Elsevier Science Publishers, Amsterdam, NL, 2018.
Wang et al., "Antibody structure, instability, and formulation," J Pharm Sci. 2007;96(1):1-26.
Response to Final Office Action as Filed in U.S. Appl. No. 15/064,195 dated Jul. 28, 2023.
Tavakolpour, Current and future treatment options for pemphigus: Is it time to move towards more effective treatments?, Int Immunopharmacol. 2017;53:133-142.
"Assignment submission for U.S. Appl. No. 61/920,547 confirming change of legal form of arGEN-X B.V. to arGEN-X N.V. on May 28, 2014", Document D30 submitted with Notice of Opposition for European Patent No. 3087095 (Application No. 14827372.5), dated May 7, 2020, 4 pages.
"Auxiliary Request 1—Annotated Version" for European Patent No. 3087095 (Application No. 14827372.5), dated Oct. 28, 2020, 5 pages.
"Auxiliary Request 1—Clean Version" for European Patent No. 3087095 (Application No. 14827372.5), dated Oct. 28, 2020, 5 pages.
"Auxiliary Request 2—Annotated Version" for European Patent No. 3087095 (Application No. 14827372.5), dated Oct. 28, 2020, 5 pages.
"Auxiliary Request 2—Clean Version" for European Patent No. 3087095 (Application No. 14827372.5), dated Oct. 28, 2020, 4 pages.
"Declaration of Pieter Spuijbroek", Document D42 submitted with Reply to Notice of Opposition for European Patent No. 3087095 (Application No. 14827372.5), dated Oct. 28, 2020, 5 pages.
"Main Request—Annotated Version" for European Patent No. 3087095 (Application No. 14827372.5), dated Oct. 28, 2020, 5 pages.
"Main Request—Clean Version" for European Patent No. 3087095 (Application No. 14827372.5), dated Oct. 28, 2020, 5 pages.
"Sequence Alignment of Seq ID No. 22 from D6 and Seq ID Nos. 1, 2, and 3 from the Patent", Document D32 submitted with Notice of Opposition for European Patent No. 3087095 (Application No. 14827372.5), dated May 7, 2020, 1 page.
"Sequence Alignment of Seq ID Nos. 1-3 from Patent and corresponding portion of Uniprot ID: P01857", Document D24 submitted with Notice of Opposition for European Patent No. 3087095 (Application No. 14827372.5), dated May 7, 2020, 1 page.
"UniProtKB—P01857 (IGHG1_HUMAN)", Document D43 submitted with Reply to Notice of Opposition for European Patent No. 3087095 (Application No. 14827372.5), dated Oct. 28, 2020, 6 pages.
Allen et al., "Efgartigimod in chronic inflammatory demyelinating polyneuropathy: Adhere phase 2 trial design", Muscle and Nerve Oct. 1, 2020 John Wiley and Sons Inc. NLD, Oct. 1, 2020, 62(Suppl. 1):abstract(1 page).
Anonymous, "A Randomized, Double-Blinded, Placebo-Controlled Trial of Efgartigimod PH20 SC in Adult Patients With Pemphigus (Vulgaris or Foliaceus)", Jul. 16, 2021, Retrieved from the Internet: URL:https://rctportal.niph.go.jp/en/detail?trial_id=jRCT2061210025, 4 pages.
Anonymous, "Evaluating the Long-Term Safety and Tolerability of Efgartigimod PH20 Sc Administered Subcutaneously in Patients With Generalized Myasthenia Gravis (ADAPTSC+)", Mar. 27, 2021, ClinicalTrials.gov, Retrieved from the Internet: URL:https://web.archive.org/web/20210327211859/https://clinicaltrials.gov/ct2/show/NCT04818671, 7 pages.
Anonymous, "History of Changes for Study: NCT05267600, A Phase 2/3 Study of Efgartigimod PH20 SC in Adult Participants With Bullous Pemphigoid (BALLAD)", Apr. 14, 2022, p. 1-7.
Anthony et al., "Recapitulation of IVIG anti-inflammatory activity with a recombinant IgG Fc", Science, Apr. 18, 2008, 320(5874):373-376.
Antohe et al., "Expression of functionally active FcRn and the differentiated bidirectional transport of IgG in human placental endothelial cells," Human Immunol., 2001, 62:93-105.
Arduin et al., "Highly reduced binding to high and low affinity mouse Fc gamma receptors by L234A/L235A and N297A Fc mutations engineered into mouse IgG2a", 2015, Molecular Immunology, 63:456-463.
Balighi et al., "Comparing early and late treatments with rituximab in pemphigus vulgaris: which one is better?", Archives of Dermatological Research, Dec. 1, 2018, 311(1):63-69.
Bitonti et al., "Pulmonary delivery of an erythropoietin Fc fusion protein in non-human primates through an immunoglobulin transport pathway," Proc. Natl. Acad. Sci. USA, 2004, 101:9763-9768.
Blumberg et al., "Anitbodies in the breakdown lane," Nature Biotechnology, 2005, 23(10):1232-1234.
Brinkhaus Maximilian et al., "The Fab region of IgG impairs the internalization pathway of FcRn upon Fc management," Nature Communications, 2022, 13(1):6073(14 pages).
Broome C. et al., "Efficacy and Safety of Efgartigimod PH20 Subcutaneous in Adult Patients with Primary Immune Thrombocytopenia: Advance SC, a Global Phase 3 Clinical Trial in Progress" [abstract]. Res Pract Thromb Haemost., 2021, 5(Suppl 2):2 pages (Year: 2021).
Bruhns et al., "Colony-Stimulating Factor-1-Dependent Macrophages are Responsible for IVIG Protection in Antibody-Induced Autoimmune Disease", Immunity, Apr. 2003, 18(4):573-581.
Brych et al., "Characterization of antibody aggregation: role of buried, unpaired cysteines in particle formation", J Pharm Sci., Feb. 2010, 99(2):764-781.
Bystryn and Jiao, "IVIg selectively and rapidly decreases circulating pathogenic autoantibodies in pemphigus vulgaris", Autoimmunity, vol. 39, No. 7, pp. 601-607, Nov. 2006 (Nov. 2006).
Burmeister et al., "Crystal structure at 2.2 A resolution of the MHC-related neonatal Fc receptor," Nature, 1994, 372(6504):336-343.
Bussel et al., "Eltrombopag for the treatment of chronic idiopathic thrombocytopenia purpura," N Engl J Med., 2007, 357(22):2237-2247.
Carter, "Potent antibody therapeutics by design", Nat Rev Immunol., May 2006, 6(5):343-357.
Challa et al., "Neonatal Fc receptor expression in macrophages is indispensable for IgG homeostasis," MAbs., 2019, 11(5):848-860 doi: 10.1080/19420862.2019.1602459. Epub Apr. 30, 2019.
ClinicalTrials.gov, "A Study to Evaluate the Safety, PD, PK and Efficacy of ARGX-113 in Patients with Pemphigus", ClinicalTrials.gov Identifier: NCT03334058, Nov. 7, 2017, 8 pages.
ClinicalTrials.gov, "A Study to Evaluate the Safety, PD, PK and Efficacy of ARGX-113 in Patients with Pemphigus", ClinicalTrials.gov Identifier: NCT04598477, Oct. 22, 2020, 10 pages.
Dalakas et al., "A controlled trial of high-dose intravenous immune globulin infusions as treatment for dermatomyositis," N Engl J Med., 1993, 329(27):1993-2000.
Dall'Acqua et al., "Increasing the affinity of a human IgG1 for the neonatal Fc receptor: biological consequences," J. Immunol., 2002, 169:5171-5180.
Dall'Acqua et al., "Properties of human IgG1s engineered for enhanced binding to the neonatal Fc receptor (FcRn)," J. Biol. Chem., 2006, 281:23514-23524.

(56) References Cited

OTHER PUBLICATIONS

Deisenhofer, "Crystallographic refinement and atomic models of a human Fc fragment and its complex with fragment B of protein A from *Staphylococcus aureus* at 2.9- and 2.8-A resolution," Biochemistry, Apr. 28, 1981, 20(9):2361-2370.
Dick Jr. et al., "C-Terminal Lysine Variants in Fully Human Monoclonal Antibodies: Investigation of Test Methods and Possible Causes", Biotechnology and Bioengineering, 2008, 100(6):1132-1143.
Dickinson et al., "Bidirectional FcRn-dependent IgG transport in a polarized human intestinal epithelial cell line," J. Clin. Invest., Oct. 1999, 104(7):903-911.
Dimitrov, "Engineered CH2 domains (nanoantibodies)", MAbs, Jan.-Feb. 2009, 1(1):26-28.
Evoli et al., "Diagnosis and therapy of myasthenia gravis with antibodies to muscle-specific kinase", Autoimmunity Review, 2013, 12:931-935.
Firan et al., "The MHC class I-related receptor, FcRn, plays an essential role in the maternofetal transfer of gamma-globulin in humans", Int. Immunol., 2001, 13(8):993-1002.
Ghanima et al., "Pharmacokinetic / Pharmacodynamic (PK/PD) Simulations Guide Selection of the Dose for Administration of Efgartigimod Subcutaneously in a Phase 3 Clinical Trial in Patients with Primary Immune Thrombocytopenia", Blood, Nov. 5, 2021, 138(Suppl. 1):3165-3165.
Ghetie et al., "FcRn: the MHC class I-related receptor that is more than an IgG transporter", Immunol Today, 1997, 18(12):592-598.
Ghetie et al., "Multiple roles for the major histocompatibility complex class I-related receptor FcRn", Annu. Rev. Immunol., 2000, 18:739-766.
Goh et al., "Impact of host cell line choice on glycan profile", Crit Rev Biotechnol., Sep. 2018, 38(6):851-867.
Gomez-Guerrero et al., "Administration of IgG Fc Fragments Prevents Glomerular Injury in Experimental Immune Complex Nephritis", J Immunol., Feb. 15, 2000, 164(4):2092-2101.
Guidance for Industry Estimating the maximum safe starting dose in initial clinical trials for therapeutics in adult healthy volunteers FDA, Jul. 2005, pp. 1-27. (Year: 2005), 30 pages.
Ha et al., "Immunoglobulin Fc Heterodimer Platform Technology: From Design to Applications in Therapeutic Antibodies and Proteins", Frontiers in Immunology, 2016, 7(394):1-16.
Hans-Hartmut et al., "Targeting FcRn for immunomodulation: Benefits, risks, and practical considerations", J Allergy Clin Immunol, Sep. 1, 2020, 146(3):479-491.
Hinton et al., "Engineered human IgG antibodies with longer serum half-lives in primates," J. Biol. Chem., 2004, 279:6213-6216.
Howard et al., "Randomized phase 2 study of FcRn antagonist efgartigimod in generalized myasthenia gravis", Neurology, 2019, 92(23):1-8.
Israel et al., "Increased clearance of IgG in mice that lack beta 2-microglobulin: possible protective role of FcRn," Immunolgy, 1996, 89:573-578.
Janeway et al., "Immunobiology: the immune system in health and disease", 6th Garland Science, New York, 2005, 5 pages.
Jefferis et al., "Human immunoglobulin allotypes: possible implications for immunogenicity", MAbs, Jul.-Aug. 2009, 1(4):332-338.
Joshi et al., "An Update on Disease Modifying Antirheumatic Drugs", Inflammation & Allergy—Drug Targets, 2014, 13:249-261.
Kabat et al., "In: Sequences of proteins of immunological interest", U.S. Department of Health and Human Services, 1991, (Title Page and Table of Contents), 11 pages.
Kabat et al., "Unusual Distributions of amino Acids in Complementarity-determining (Hypervariable) Segments of Heavy and Light Chains of Immunoglobulins and Their Possible Roles in Specificity of Antibody-combining Sites", The Journal of Biological Chemistry, Oct. 1, 1977, 252(19):6609-6616.
Kaneko et al., "Anti-inflammatory activity of immunoglobulin G resulting from Fc sialylation", Science, Aug. 4, 2006, 313(5787):670-673.

Kasperkiewicz et al., "Pemphigus." Nat Rev Dis Primers., 2017, 3:17026(40 pages).
Kasprick et al., "Treatment with anti-neonatal Fc receptor (FcRn) antibody ameliorates experimental epidermolysis bullosa acquisita in mice", British Journal of Pharmacology, Wiley-Blackwell, Mar. 6, 2020, 177(10):2381-2392.
Khan et al., "Clinical Practice Updates in the Management of Immune Thrombocytopenia," P & T., 2017, 42(12):756-763.
Kiessling Peter et al, "The FcRn inhibitor rozanolixizumab reduces human serum IgG concentration: A randomized phase 1 study", Science Translational Medicine, Nov. 1, 2017, 9(414):1-12.
Kim et al., "Localization of the site of the murine IgG1 molecule that is involved in binding to the murine intestinal Fc receptor," Eur. J. Immunol., 1994, 24:2429-2434.
Kobayashi et al., "FcRn-mediated transcytosis of immunoglobulin G in human renal proximal tubular epithelial cells", Am. J. Physiol. Renal Physiol., 2002, 282:F358-F365.
Li et al., "Myasthenia gravis: newer therapies offer sustained improvement", Cleveland Clinic Journal of Medicine, 2013, 80(11):711-721.
Ishii-Watabe et al., "Molecular Design of Therapeutics Monoclonal Antibodies," Journal of Pharmaceutical Science and Technology, Japan, 2014, 74(1):4-11.
Maho-Vaillant et al., "FcRn Antagonism Leads to a Decrease of Desmoglein-Specific B Cells: Secondary Analysis of a Phase 2 Study of Efgartigimod in Pemphigus Vulgaris and Pemphigus Foliaceus", Frontiers in Immunology, May 18, 2022, 13(Article 863095):14 pages.
Matt Hoffman, "Subcutaneous Efgartigimod Shows Noninferiority to IV Formulation in Generalized Myasthenia Gravis", Mar. 23, 2022, Neurology, Retrieved from the Internet:URL:https://web.archive.org/web/20220326043901/https://www.neurologylive.com/view/subcutaneous-efgartigimod-noninferior-iv-formulation-vygart-generalized-myasthenia-gravis, 3 pages.
McCarthy et al., "Bidirectional transcytosis of IgG by the rat neonatal Fc receptor expressed in a rat kidney cell line: a system to study protein transport across epithelia", J. Cell Sci., 2000, 113:1277-1285.
Medesan et al., "Comparative studies of rat IgG to further delineate the Fc:FcRn interaction site," Eur. J. Immunol., 1998, 28:2092-2100.
Michael F. Halle, "Converting Intravenous Dosing to Subcutaneous Dosing with Recombinant human Hyaluronidase", Pharmaceutical Technology, Advanstar Communications Inc., Oct. 2, 2007, 31(10):10 pages.
Newland et al., "Phase 2 study of efgartigimod, a novel FcRn antagonist, in adult patients with primary immune thrombocytopenia," Am J Hematol., 2020, 95(2):178-187.
Nih, A Study to Assess the Long-term Safety and Efficacy of a Subcutaneous Formulation of Efgartigimod PH20 SC in Adults With Pemphigus (Vulgaris or Foliaceus), Oct. 22, 2020, Retrieved from the Internet: URL:https://web.archive.org/web/20201101124721/https://clinicaltrials.gov/ct2/show/NCT04598477, 10 pages.
Popov et al., "The stoichiometry and affinity of the interaction of murine Fc fragments with the MHC class I-related receptor, FcRn," Mol. Immol., 1996, 33:521-530.
Putnam et al., "Proteins in Multiple Myeloma: VIII. Biosynthesis of Abnormal Proteins", J Biol Chem., Apr. 1958, 231(2):671-684.
Pyzik et al., "The Neonatal Fc Receptor (FcRn): A Misnomer?", Front Immunol., Jul. 10, 2019, 10:1540(24 pages).
Raghavan et al., "Analysis of the pH Dependence of the Neonatal Fc Receptor/Immunoglobulin G Interaction Using Antibody and Receptor Variants," Biochemistry, 1995, 34:14649-14657.
Robak et al, "Single-Agent Ibrutinib Vs Chemoimmunotherapy Regimens for Treatment-Naive Patients with Chronic Lymphocytic Leukemia (CLL): A Cross-Trial Comparison", Blood, 2017, 130(Suppl. 1):1750(6 pages).
Robak et al., "Efficacy and Safety of a new intravenous immunoglobulin 10% formulation (octagam 10%) in patients with immune throbmbocytopenia", Hematology, 2010, 15(5):351-359.
Robak et al., "Phase II, Multiple-Dose Study of Anti-FcRn Antibody, Rozanolixizumab (UCB7665), in Patients with Primary Immune

(56) References Cited

OTHER PUBLICATIONS

Thrombocytopenia: Interim Analysis", Blood, Dec. 7, 2017, 130(Suppl. 1):15(8 pages), 59th Annual Meeting of the American-Society-of-Hematology, Dec. 9-12, 2017.
Rosenwasser et al., "Anti-CD23", Clinical Reviews in Allergy and Immunology, 2005, 29:61-72.
Rudikoff et al., "Single amino acid substitution altering antigen-binding specificity", Proc. Natl. Acad. Sci. USA, 1982, 79(6):1979-1983.
Samuelsson et al., "Anti-inflammatory activity of IVIG mediated through the inhibitory Fc receptor", Science, Jan. 19, 2001, 291(5503):484-486.
Schwab et al., "Intravenous immunoglobulin therapy: how does IgG modulate the immune system?", Nat. Rev. Immunol., Mar. 2013, 13(3):176-189.
Shang et al., "Modular protein expression by RNA trans-splicing enables flexible expression of antibody formats in mammalian cells from a dual-host phage display vector", Protein Engineering, Design & Selection, 2015, 28(10):437-444.
Silvestri et al., "Treatment-Refractory Myasthenia Gravis", Journal of Clinical Neuromuscular Disease, 2014, 15(4):167-178.
Spiekermann et al., "Receptor-mediated Immunoglobulin G Transport Across Mucosal Barriers in Adult Life: Functional Expression of FcRn in the Mammalian Lung", J. Exp. Med., 2002, 196(3):303-310.
Ulrichts et al., "Supplemental data Neonatal Fc receptor antagonist efgartigimod safely and sustainably reduces IgGs in humans", J. Clin. Invest., 2018, 128(10):4372-4386.
Van Faassen et al., "Serum albumin-binding VHHs with variable pH sensitivities enable tailored half-life extension of biologics," FASEB J., 2020, 34(6):8155-8171. doi: 10.1096/fj.201903231R. Epub Apr. 28, 2020.
Vitetta et al., "Considering therapeutic antibodies", Science, Jul. 21, 2006, 313(2):308-309.
Wang, "Protein aggregation and its inhibition on biopharmaceutics", International Journal of Pharmaceutics, Jan. 31, 2005, 289(1-2):1-30.
Ward et al., "Chapter 4: Multitasking by exploitation of intracellular transport functions the many faces of FcRn", Chapter 4, Adv. Immunol., 2009, 103:77-115.
Weiner et al., "Tunable antibodies", Nature Biotechnology, May 2005, 23(5):556-557.
Wittlin et al. "Pharmacokinetic/Pharmacodynamic Simulations Guide Selection of the Dose for Administration of Efgartigimod Subcutaneously in a Phase 3 Clinical Trial in Patients with Primary Immune Thrombocytopenia", British Journal of Haematology; 62nd Annual Scientific Meeting of The British Society for Haematology 20220403 to 0220405 Virtual, Blackwell Publishing Ltd, Apr. 1, 2022, 197(Suppl. 1):44.
Yoshida et al., "Human Neonatal Fc Receptor Mediates Transport of IgG into Luminal Secretions for Delivery of Antigens to Mucosal Dendritic Cells," Immunity, 2004, 20:769-783.
"Corrected Filing Receipt for U.S. Appl. No. 61/920,547 dated Apr. 16, 2015", Document D27 submitted with Notice of Opposition for European Patent No. 3087095 (Application No. 14827372.5), dated May 7, 2020, 3 pages.
"Corrected Filing Receipt for U.S. Appl. No. 61/920,547 dated Apr. 18, 2014", Document D26 submitted with to Notice of Opposition for European Patent No. 3087095 (Application No. 14827372.5), dated May 7, 2020, 3 pages.
"Cover Letter to the European Patent Office" for European Patent No. 3087095 (Application No. 14827372.5), dated Oct. 28, 2020, 1 page.
"Filing Receipt for U.S. Appl. No. 61/920,547 dated Jan. 21, 2014", Document D25 submitted with Notice of Opposition for European Patent No. 3087095 (Application No. 14827372.5), dated May 7, 2020, 3 pages.
"Inventor Assignment of U.S. Appl. No. 61/920,547 to arGEN-X B.V. executed Oct. 31, 2014 and Nov. 4, 2014", Document D29 submitted with Notice of Opposition for European Patent No. 3087095 (Application No. 14827372.5), dated May 7, 2020, 10 pages.
"Inventor Assignment of U.S. Appl. No. 61/920,547 to The Board of Regents of the University of Texas System executed Dec. 23, 2014", Document D28 submitted with Notice of Opposition for European Patent No. 3087095 (Application No. 14827372.5), dated May 7, 2020, 4 pages.
"Notice of Opposition" to European Patent No. 3087095 (Application No. 14827372.5), dated May 7, 2020, 47 pages.
"Online Filing Acknowledgement for Notice of Opposition" for European Patent No. 3087095 (Application No. 14827372.5), dated May 7, 2020, 3 pages.
"Online Filing Acknowledgement for Reply to Notice of Opposition" for European Patent No. 3087095 (Application No. 14827372.5), dated Oct. 28, 2020, 2 pages.
"PCT Request for as filed for PCT/US2014/072087 on Dec. 23, 2014", Document D34 submitted with Notice of Opposition for European Patent No. 3087095 (Application No. 14827372.5), dated May 7, 2020, 6 pages.
"Proof of Employment for Inventor/Applicant Sally Ward", Document D40 submitted with Reply to Notice of Opposition for European Patent No. 3087095 (Application No. 14827372.5), dated Oct. 28, 2020, 1 page.
"Reply to Notice of Opposition" for European Patent No. 3087095 (Application No. 14827372.5), dated Oct. 28, 2020, 35 pages.
"Rule 90101 of the Rules and Regulations of the Board of Regents of the University of Texas System governing intellectual property" dated Feb. 27, 2012, Document D41 submitted with Reply to Notice of Opposition for European Patent No. 3087095 (Application No. 14827372.5), on Oct. 28, 2020, 21 pages.
International Preliminary Report on Patentability received for PCT/EP2020/065716, mailed on Dec. 7, 2021, 8 pages.
International Preliminary Report on Patentability received for PCT/EP2018/084034, mailed on Jun. 18, 2020, 11 pages.
International Preliminary Report on Patentability received for PCT/US2006/021456, mailed on Dec. 6, 2007, 8 pages.
International Search Report and Written Opinion received for PCT/EP2020/065716, mailed Sep. 14, 2020.
International Search Report and Written Opinion received for PCT/EP2021/050275, mailed Apr. 8, 2021.
International Search Report and Written Opinion received for PCT/EP2023/050980 mailed on Apr. 12, 2023, 13 pages.
International Search Report and Written Opinion received for PCT/EP2023/061012 mailed on Aug. 3, 2023, 15 pages.
International Search Report and Written Opinion received for PCT/EP2023/066162, mailed on Aug. 16, 2023, 18 pages.
International Search Report and Written Opinion received for PCT/EP2023/066163, mailed on Sep. 27, 2023, 22 pages.
International Search Report and Written Opinion received for PCT/IB2022/000443, mailed on Mar. 6, 2023, 29 pages.
International Search Report and Written Opinion received for PCT/US2006/021456, mailed on Nov. 17, 2006, 8 pages.
Invitation to Pay Additional Fees received for PCT/IB2022/000443 mailed on Dec. 16, 2022, 19 pages.
Invitation to Pay Additional Fees received for PCT/EP2023/066180, mailed Sep. 27, 2023, 13 pages.
Howard Jr. et al., "Safety, efficacy, and tolerability of efgartigimod in patients with generalised myasthenia gravis (ADAPT): a multicentre, randomised, placebo-controlled, phase 3 trial", Lancet Neurol, 2021, 20:526-536.
Press Release "argenx Reports Topline Results from ADVANCE-SC Study of VYVGART Hytrulo in Primary Immune Thrombocytopenia", Nov. 28, 2023, 4 pages.
Press Release "argenx Reports Topline Results from ADDRESS Study of Efgartigimod SC in Pemphigus", Dec. 20, 2023, 5 pages.
Blumberg et al., "Blocking FcRn in humans reduces circulating IgG levels and inhibits IgG immune complex-mediated immune responses", Sci. Adv., Dec. 18, 2019, 5(12):eaax9586, 12 pages.
Broome et al, "Efficacy and safety of the neonatal Fc receptor inhibitor efgartigimod in adults with primary immune thrombocytopenia (ADVANCE IV): a multicentre, randomised, placebo-controlled, phase 3 trial", Lancet, Nov. 4, 2023, 402(10413):1648-1659.

(56) References Cited

OTHER PUBLICATIONS

ClinicalTrials.gov, "History of Changes for Study: NCT05810961—A Study to Assess Effectiveness and Safety of Efgartigimod in Chinese Patients With Primary Membranous Nephropathy (ZL-1103-014)", ClinicalTrials.gov Identifier: NCT05810961, Oct. 2, 2023, 11 pages.
ClinicalTrials.gov, "A Study of Nipocalimab in Adults With Primary Sjogren's Syndrome (pSS)", ClinicalTrials.gov Identifier: NCT04968912, Janssen Research & Development, LLC, Jul. 20, 2021, 9 pages.
ClinicalTrials.gov, "A Study to Assess Effectiveness and Safety of Efgartigimod in Chinese Patients With Lupus Nephritis (ZL-1103-013)", ClinicalTrials.gov Identifier: NCT05810948, Oct. 2, 2023, 17 pages.
ClinicalTrials.gov, "Efficacy and Safety Study of Efgartigimod in Adults With Post-COVID-19 POTS (POTS)", ClinicalTrials.gov Identifier: NCT05633407, Nov. 29, 2022, 13 pages.
Dylewski et al., "Exploiting the neonatal crystallizable fragment receptor to treat kidney disease", Kidney International, 2024, 105(1):54-64.
Goebeler et al., "Treatment of pemphigus vulgaris and foliaceus with efgartigimod, a neonatal Fc receptor inhibitor: a phase II multicentre, open-label feasibility trial", British Journal of Dermatology, 2022, 186(3):429-439.
Hettmann et al., "Development of the clinical candidate PBD-C06, a humanized pGlu3-ABeta-specific antibody against Alzheimer's disease with reduced complement activation", Scientific Reports, 2020, 10(3294):13 pages.
Hubbard et al., "Design of a Phase 2, Multicenter, Randomized, Placebo-Controlled, Double-blind Study to Assess the Efficacy and Safety of Nipocalimab, an FcRn Antagonist, in Adults with Primary Sjogrens Syndrome", Evolving Topics in pSS Therapy, 15th International Symposium on Sjogren's Syndrome, 2022, 40:2477-2597, Poster—97.
Knoebl et al., "Pb2305-Efgartigimod: Clinical Development of a Novel FcRn Antagonist in the Treatment of Autoimmune Diseases", Hemasphere, Jan. 1, 2022, 6:2175-2176.
Lobner et al., "Engineered IgG1-Fc—one fragment to bind them all", Immunological Reviews, 2016, 270(1):113-131.
Olaru et al., "Neonatal Fc Receptor Promotes Immune Complex-Mediated Glomerular Disease", J Am Soc Nephrol, 2014, 25(5):918-925.
Patel et al., "FcRn blockade by Fc engineering ameliorates arthritis in a murine model", J Immunol., Jul. 15, 2011, 187(2):1015-1022.
Patel et al., "Neonatal Fc receptor in human immunity: Function and role in therapeutic intervention", J Allergy Clin Immunol, Sep. 2020, 146(3):467-478.
Peene et al., "AB0520-Treatment of Primary Sjogren's Syndrome by Inhibiting FcRn: A Phase 2 Randomized, Placebo Controlled, Double-Blind, Proof of Concept Study with Efgartigimod", Scientific Abstracts, May 30, 2023, 1455-1456.
Polanco et al., "Spontaneous Remission of Nephrotic Syndrome in Idiopathic Membranous Nephropathy", J Am Soc Nephrol, 2010, 21(4):697-704.
Press Release "argenx Advances Clinical Development of Efgartigimod in Primary Sjogren's Disease", Mar. 27, 2024, 3 pages.
Press Release "argenx Announces Approval of VYVGART (efgartigimod alfa) in Japan for Adults with Primary Immune Thrombocytopenia", Mar. 26, 2024, 4 pages.
Rojas-Rivera et al., "Recent Clinical Trials Insights into the Treatment of Primary Membranous Nephropathy", Drugs, 2022, 82(2):109-132.
Warne, "Development of high Concentration protein biopharmaceuticals: The use of platform approaches in formulation development", European Journal of Pharmaceutics and Biopharmaceutics, 2011, 78(2):208-212.
International Search Report and Written Opinion received for PCT Patent Application No. PCT/IB2023/000679, mailed on Apr. 3, 2024, 17 pages.
International Search Report and Written Opinion received for PCT Patent Application No. PCT/IB2023/000688, mailed on Apr. 29, 2024, 16 pages.
International Search Report and Written Opinion received for PCT Patent Application No. PCT/IB2024/000041, mailed on Jun. 3, 2024, 14 pages.
International Search Report and Written Opinion received for PCT Patent Application No. PCT/EP2023/066180, mailed on Nov. 17, 2023, 19 pages.
International Search Report and Written Opinion received for PCT Patent Application No. PCT/IB2023/000696, mailed on Jun. 4, 2024, 21 pages.
International Search Report and Written Opinion received for PCT Patent Application No. PCT/IB2024/000018, mailed on May 24, 2024, 16 pages.
Invitation to Pay Additional Fees received for PCT Patent Application No. PCT/IB2023/000696, mailed on Apr. 12, 2024, 15 pages.

* cited by examiner

Fig. 2
Schedule of Assessments

| Assessments | Screening | Screening | Visits | | | | | | | | | | | | | | | |
|---|---|---|---|---|---|---|---|---|---|---|---|---|---|---|---|---|---|---|
| | | | Treatment period (Visit 1 to Visit 7) | | | | | | | Follow-Up period (Immediately after last Infusion) | | | | | | | | Safety |
| Visits | | | V1 | V2** | V3 | V4** | V5 | V6** | V7 | V8** | V9 | V10 | V11 | V12 | V13 | V14 | V15 | V16 | |
| Study Day* | | 1 | 5±1 | 8±1 | 12±1 | 15±1 | 19±1 | 22±1 | 26±1 | 29±1 | 36±1 | 43±1 | 50±1 | 57±1 | 64±1 | 71±1 | 78±1 | | US |
| | | | | | | | | | EoT | | | | | | | | | EoS/ED | |
| Informed consent[b] | X | | | | | | | | | | | | | | | | | | |
| Inclusion and | X | xe | | | | | | | | | | | | | | | | | |
| Medical/surgical | X | | | | | | | | | | | | | | | | | | |
| Randomization | | Xe | | | | | | | | | | | | | | | | | |
| Demographic | X | | | | | | | | | | | | | | | | | | |
| Physical examination[c] including Height[d] and | xc, d | | X | | X | | X | | xc | | X | X | | X | | X | | Xc | X |
| Vital Signs (Blood Pressure, Heart | X | Xe | | Xe | | Xe | | Xe | | X | X | X | X | X | X | X | X | X | X |
| MGQoL15re | X | X | | X | | X | | X | | X | X | X | X | X | X | X | X | X | X |
| MG-ADLe | X | X | | X | | X | | X | | X | X | X | X | X | X | X | X | X | X |
| QMGe | X | X | | X | | X | | X | | X | X | X | X | X | X | X | X | X | X |
| MGCe | X | X | | X | | X | | X | | X | X | X | X | X | X | X | X | X | X |
| Clinical laboratory | | X | X | X | X | X | X | X | X | X | X | X | X | X | X | X | X | X | X |
| Pharmacodynamics: anti-AChR antibodies and ECG[h] | | xe Xe Xi Xe | Xe Xi | Xe Xi | Xe Xi | Xe Xi | Xi | xe Xe Xi Xe | | | | | | | | | | | |
| Urinalysis | | X | | | | | | | X | | X | X | X | | X | | X | | X X |
| Pharmacokinetics: | | X | X | X | X | X | X | X | X | X | X | X | | | | | | | X |
| Anti-drug antibodies | | X | | X | | X | | X | X | X | X | X | | X | | X | | X | X |
| Serum Pregnancy | X | X | | | | | | | | | | | | | | | | | |
| Urine Pregnancy test[k] | | | Xm | | | | | | | | | | | | | | | | |
| Viral and bacterial | X | | | | | | | | | | | | | | | | | | |
| Pharmacogenetics[m] | | X | X | X | X | X | X | X | X | X | X | | | | | | | | |
| Administration of ARGX-113 or | | | | | | | | | | | | | | | | | | | |
| Suicidality | X | X | X | X | X | X | X | X | X | X | X | X | X | X | X | X | X | X | X |
| Concomitant | X | X | X | X | X | X | X | X | X | X | X | X | X | X | X | X | X | X | X |
| Adverse events[p] | X | X | X | X | X | X | X | X | X | X | X | X | X | X | X | X | X | X | X |

Fig. 2 (CONTINUED)

Abbreviations: BMI = Body Mass Index; ECG = Electrocardiogram; ED = Early Discontinuation; EoS = End-of-Study; EoT = End-of-Treatment; FU = Follow-Up; MG-ADL = Myasthenia Gravis-Activities of Daily Living; QMG = Quantitative Myasthenia Gravis score; MGC = Myasthenia Gravis Composite score; MGQoL15r = 15-item quality of life scale for Myasthenia Gravis [Revised version]; US = Unscheduled; V = Visit.

*: The allowed window period between visits in Treatment period and Follow-up period is ±1 day provided that 2 consecutive visits are 3 days apart at a minimum. Every effort should be made to schedule every visit on the exact Day (which is relative to a baseline visit or [Visit 1]) as described in above Schedule of Assessments (Table) without the window.

**: The Visits 2, 4, 6, and 8 are optional a. To take place within 15 days prior to first administration of the Investigational Medicinal Product (IMP) at Visit 1.
b. No study-related assessment is to be carried out before the patient has signed informed consent.
c. A complete physical examination will be performed at Screening, Visit 7, and at Visit 16/EoS/ED. An abbreviated examination will be done at all other visits. On dosing days, physical examination including weight measurement should be performed pre-dose.
d. Height should only be measured at Screening (and Body Mass Index [BMI] to be calculated accordingly at Screening only).
e. Randomization to be performed only after confirmation of eligibility of the patient including the MG-ADL score assessed at Visit 1 and prior to dosing at Visit 1. The assessments for vital signs, urinalysis, and anti-drug antibodies, must be performed pre-dose at visits when the Investigational Medicinal Product (IMP) is administered (Visits 1, 3, 5, and 7). Efficacy assessments scheduled on designated Days should be completed pre-dose on each dosing day and should be performed prior to any other study specific assessment, except for obtaining informed consent at Screening. Efficacy assessments should be performed in the following sequence (at each study visit including these assessments): MGQoL15r, MG ADL, QMG, and MGC. Cholinesterase inhibitors must be held for at least 12 hours before the MGQoL15r, MG-ADL, QMG, and MGC assessments (consistent with the revised manual for the QMG test as recommended by the Myasthenia Gravis Foundation of America Inc [MGFA])¹. A total score ≥5 on the MG-ADL with more than 50% of this score attributed to non-ocular items should be met at both Screening and Baseline (Visit 1) to confirm eligibility.
f. Sampling for clinical laboratory tests is to be performed pre-dose on dosing days and tests will include hematology (hemoglobin, platelet count, white blood cell count with differential); blood chemistry (including creatinine, creatinine clearance, blood urea nitrogen [BUN], glucose, alanine aminotransferase [ALT], aspartate aminotransferase [AST], total bilirubin, gamma-glutamyl transferase [GGT], C-reactive protein [CRP], alkaline phosphatase [AP], lactate dehydrogenase [LDH], uric acid, albumin, potassium, calcium, sodium, thyroglobulin, International normalized ratio or activated partial thromboplastin time [aPTT], CD19 counts). Patients need to be fasting for at least 8 hours prior to this sampling.
g. Sampling for pharmacodynamic biomarkers is to be performed pre-dose on dosing days and include anti-AChR antibodies and immunoglobulin G and its sub-types. Analysis of anti-AChR antibodies will include anti-AChR binding antibodies and anti-AChR blocking antibodies. IgG measurements include total IgG, IgG subtypes (IgG 1, IgG 2, IgG 3, and IgG 4). In addition, IgA, IgD, IgE, and IgM will also be assessed.

Fig. 2 (CONTINUED)

h. ECG (heart rate, PR, QT, and QRS interval) will be read locally and should be performed pre-dose on dosing days.
i. Pharmacokinetic (PK) assessments should be done both pre- and post-dose (within 30 minutes prior to start of infusion for pre-dose sample and within 30 minutes after end of infusion for post-dose sample) on all IMP infusion days.
j. Serum pregnancy test must be performed in women of childbearing potential at Screening from the blood sample collected for clinical laboratory tests at the central laboratory.
k. Urine pregnancy test will be performed locally pre-dose at Visits 1, 3, 5, 7, 11, and 16/EoS/ED.
l. Tests to assess HbsAg, anti-HCV antibodies, Follicle stimulating hormone (FSH), HIV antibodies and tuberculosis serology (QuantiFERON®-TB Gold) test will be performed at the central laboratory.
m. A blood sample for the optional pharmacogenetic testing is to be collected before the first dose of the Investigational Medicinal Product is administered at Visit 1 (Baseline) after a separate pharmacogenetic ICF has been signed, and will be stored for pharmacogenetic analysis. Only if the blood sample at Visit 1 is missed, the sample should be drawn at Visit 3 before the administration of the Investigational Medicinal Product.
n. The Investigational Medicinal Product or placebo will be administered as an IV infusion over a period of 2 hours at Visits 1, 3, 5, and 7. Patients should remain at the site for at least 2 hours following the end of the infusion for safety monitoring based on the patient's clinical status.
o. Suicidal ideation and behavior will be assessed via a targeted question based on the Patient Health Questionnaire item 9 (PHQ-9)[2] at each scheduled visit except the optional visit.
p. Adverse events and intake of concomitant medication(s) will be monitored continuously from signing of informed consent until the last study-related activity at Visit 16. In case of early discontinuation, any AEs/SAEs should be assessed for 30 days following the early discontinuation visit and until satisfactory resolution or stabilization.

Fig. 3

MYASTHENIA GRAVIS ACTIVITIES OF DAILY LIVING (MG-ADL) SCORING

| Grade | 0 | 1 | 2 | 3 | Score |
|---|---|---|---|---|---|
| Talking | Normal | Intermittent slurring or nasal speech | Constant slurring or nasal, but can be understood | Difficult to understand speech | |
| Chewing | Normal | Fatigue with solid food | Fatigue with soft food | Gastric tube | |
| Swallowing | Normal | Rare episode of choking | Frequent choking necessitating changes in diet | Gastric tube | |
| Breathing | Normal | Shortness of breath with exertion | Shortness of breath at rest | Ventilator dependence | |
| Impairment of ability to brush teeth or comb hair | None | Extra effort, but no rest periods needed | Rest periods needed | Cannot do one of these functions | |
| Impairment of ability to arise from a chair | None | Mild, sometimes uses arms | Moderate, always uses arms | Severe, requires assistance | |
| Double vision | None | Occurs, but not daily | Daily, but not constant | Constant | |
| Eyelid droop | None | Occurs, but not daily | Daily, but not constant | Constant | |

Total score _____

Fig. 4

QUANTITATIVE MYASTHENIA GRAVIS TESTING FORM

Patient Name: _____ Patient #: _____ Date: _____
MR#: _____ DOB: _____ Sex: _____ Ht.(in) _____ Wt.(kg): _____
Evaluator: _____ Handedness: _____ Leggedness: _____ Time of Exam: _____
Anticholinesterase Medication: _____
Comments:

| TEST ITEMS WEAKNESS | NONE | MILD | MODERATE | SEVERE | SCORE |
|---|---|---|---|---|---|
| GRADE | 0 | 1 | 2 | 3 | |
| Double vision (lateral gaze) Sec. | 60 | 11-59 | 1-10 | Spontaneous | |
| Ptosis (upward gaze) Sec. | 60 | 11-59 | 1-10 | Spontaneous | |
| Facial Muscles | Normal lid closure | Complete, weak, some resistance | Complete, without resistance | Incomplete | |
| Swallowing 4 oz. Water (1/2 cup) | Normal | Minimal coughing or throat clearing | Severe coughing Choking or nasal regurgitation | Cannot swallow (test not attempted) | |
| Speech following counting aloud from 1- 50 (onset of dysarthria) | None at #50 | Dysarthria at #30-49 | Dysarthria at #10-29 | Dysarthria at #9 | |
| Right arm outstretched(90°, sitting) Sec. | 240 | 90-239 | 10-89 | 0-9 | |
| Left arm outstretched (90°, sitting) Sec. | 240 | 90-239 | 10-89 | 0-9 | |
| Forced vital capacity | >80% | 65-79% | 50-64% | <50% | |
| Rt hand grip: male (Kg):female | >45:>30 | 15-44:10-29 | 5-14:5-9 | 0-4:0-4 | |
| Left hand grip: male (Kg):female | >35:>25 | 15-34:10-24 | 5-14:5-9 | 0-4:0-4 | |
| Head, lifted (45%, supine) Sec. | 120 | 30-119 | 1-29 | 0 | |
| Right leg outstretched (45-50%,supine) | 100 | 31-99 | 1-30 | 0 | |
| Left leg outstretched (45-50%,supine) | 100 | 31-99 | 1-30 | 0 | |

TOTAL QMG SCORE: _____

Fig. 4 (CONTINUED)

GENERAL INSTRUCTIONS

1. Patients must be off pyridostigmine (or any acetylcholinesterase inhibitor medication) for twelve (12) hours prior to testing, (if medically safe to do so).

2. Perform the tests in the order given in this Manual and shown on the Videotape.

3. Calibrate the respiratory equipment on the day of the test, per manufacturers' instruction, before the test begins. Place the calibration record in folder in an accessible place.

4. For all measurements, record actual numbers as well as grade, i.e., if it takes 30 seconds before a patient sees double, record on the far right box 30/1 for 30 seconds and a grade of 1.

5. Patients must remain seated for the respiratory test.

6. At the end of the scoring sheet, add up the grade for that patient and that becomes the Total QMG Score.

QUANTITATIVE MG SCORE

I. DOUBLE VISION:

Patients' preparation: Patient is sitting. Ask if the patient is experiencing double vision looking straight ahead. If yes, record 0/3 (actual time/grade) on the scoring sheet. If no, ask the patient to look to the right for just an instant and then to the left without moving their head. If the patient sees double in only one direction, record side and record result as 0/3. If there is no eye movement, record as 0/3. If the patient does not see double, or sees double in both directions, have them perform the test as described below gazing to the right.

Explanation to patient: "I need for you to face forward. When I ask, look over to your right (left) side without turning your head. If or when you start to see double, please let me know."

Notes to examiner: Patient's head will usually start to turn in the direction of the gaze. Try to maintain the head in a forward position. Record the time and grade. Example: double vision is evident at 15 sec. In the scoring section, record 15/1.

Fig. 4 (CONTINUED)

II. PTOSIS (upward gaze):

Patients' preparation: Patient is sitting. Ask the patient to look straight ahead. If the upper lid is touching the pupil, record as 0/3. Ask the patient to look up at the ceiling without moving the head.

Explanation to patient: "I need you to face forward. When I ask, look up at the ceiling without moving your head. Keep looking up until I tell you to relax."

Notes to examiner: Patient's head will usually start to move up. Try to maintain the head in a forward position. Record time and grade when you see either eyelid (lashes) start to droop. Ex: Right eyelid starts to droop at 9 sec., record 9/2. If neither eyelid touches the pupil, record 60/0.

III. FACIAL MUSCLES:

Patients' preparation: Patient is sitting facing forward.

Explanation to patient: "Squeeze your eyes shut. Do not allow me to open your eyes."

Notes to examiner: If the patient cannot fully close either eye shut, record the grade as 3. No time score is needed on this test. Record grade of the weaker eye.

IV. SWALLOWING:

Patient's preparation: Patient is sitting. Four ounces of water (no ice) is poured into a cup. The water should be no cooler than water fountain cool.

Explanation to patient: "I need for you to drink this water as you normally would."

Notes to examiner: Listen for coughing and/or throat clearing during the test and immediately post test. Don't ask patients to drink faster than what they feel comfortable doing.

Fig. 4 (CONTINUED)

V. SPEECH:

Patient's preparation: Patient is sitting.

Explanation to patient: "Count out loud from 1 to 50 at a comfortable pace."

Notes to examiner: This is one of the most difficult tests to score because of varying accents. Record number when you notice a nasal or slurring of the speech. VI. RIGHT & LEFT ARM OUTSTRETCHED:

Patient's preparation: The patient needs to be sitting in a chair with both feet on the floor. They must be seated without leaning against the back of a chair. Test both arms at the same time. Arms need to be out to the side at 90o, palms down. (Demonstrate this position). If the patient cannot raise an arm out to 90° due to a shoulder problem, do not test that arm. The elbows are extended through full mechanical range.

Explanation to patient: "I need for you to hold both arms out to the side like this. Keep the arms out as long as possible. If one arm tires more than the other, you may lower that arm and keep the other arm up."

Notes to examiner: It is not uncommon that the arms start to droop. If the arms drop more than 10° from starting position, remind the patient to pull the arms up. If the patient can pull the arms up but cannot maintain that position for longer than two seconds, stop the test. If one arm is lowered, be careful that the patient does not start to lean to the side that the arm was lowered to give the appearance that he/she is maintaining a 90° angle. Record time/grade (ex: 45 sec for right arm is 45/2; whereas 100 sec for left arm is 100/1).

Fig. 4 (CONTINUED)

VII: FORCED VITAL CAPACITY:

Patient preparation: Patients must remain seated for this test.

Explanation to patient: "I am testing total lung capacity. I am going to ask you to hold this mouthpiece away from your face. I will then place the nose-clips on your nose. I will tell you to take a deep breath in, and then place the mouthpiece in your mouth. You will blow out as hard and as fast as you can. Keep blowing until I tell you to stop.

Notes to examiner: We are only testing FVC. A minimum of three trials and a maximum of five trials will be performed. The goal is to get the best two trials within 5% of each other. Give a lot of encouragement. Record best FVC (liters and percentage) and grade on sheet, (ex: 2.55 - 60% / 2).

The "normal" FVC values, and therefore the percent predicted calculations can vary with the spirometer that is used. Some spirometers come with specified normal values. That is why the same spirometer should be used each time you test a subject. For multi-site studies, parameters and normal values should be decided so that all sites are using the same information.

VIII: RIGHT & LEFT HAND GRIP:

Patient preparation: Patient is sitting in a chair. The elbow should be at 90o. Support should be under the medial aspect of the forearm and under the dynamometer.

Explanation to patient: "I am testing grip strength. I need for you to squeeze as hard as you can. Nothing will move, but it is measuring how hard you are squeezing."

Notes to examiner: Give vocal encouragement. Record the two trials (kgs) in column and score (ex: if testing a female and results are 10 and 8 kgs, record as 10/1.)

Fig. 4 (CONTINUED)

IX. HEAD LIFTED:

Patient preparation: The patient will lie down without a pillow under the head. A pillow may be placed under the knees or the knees bent so that the feet are flat on the bed.

Explanation to patient: "I need for you to lift your head off of the table. Keep it up as long as possible."

Notes to examiner: Place your hand under their head (without touching) to provide some cushion if the head drops back. The head should come up and forward, not just up to the ceiling. If the head drops within 10o of neutral, stop the test.

X. RIGHT & LEFT LEG OUTSTRETCHED:

Patient preparation: Patient is supine with a pillow under the head. Both legs must be out straight and shoes off.

Explanation to patient: "I need for you to hold your right leg up. Hold the leg up in this position as long as possible."

Notes to examiner: Leg must be maintained at 45-50% of hip flexion. If the leg starts to droop, ask the patient to lift the leg up. If the patient lifts the leg up, but cannot maintain that position for 2 seconds, stop the test. Watch for hands under the hips and/or rotation of the leg.

Fig. 5

Myasthenia Gravis Composite Score

| | | | |
|---|---|---|---|
| Ptosis, upward gaze (physician) | > 45 seconds = 0 | 11 – 45 seconds = 1 | 1 – 10 seconds = 2 | Immediate = 3 |
| Double vision on gaze, left or right (physician) | > 45 seconds = 0 | 11 – 45 seconds = 1 | 1 – 10 seconds = 3 | Immediate = 4 |
| Eye closure (physician) | Normal = 0 | Mild weakness (can be forced open with effort) | Moderate weakness (can be forced open easily) | Severe weakness (unable to keep eyes closed) |
| Talking (patient history) | Normal = 0 | Intermittent slurring or nasal speech = 2 | Constant slurring or nasal but can be | Difficult to understand speech = 6 |
| Chewing (patient history) | Normal = 0 | Fatigue with solid food = 2 | Fatigue with soft food = 4 | Gastric tube = 6 |
| Swallowing (patient history) | Normal = 0 | Rare episode of choking or trouble | Frequent trouble swallowing e.g. | Gastric tube = 6 |
| Breathing (thought to be) | Normal = 0 | Shortness of breath with exertion = 2 | Shortness of breath at rest = 4 | Ventilator dependence = 9 |
| Neck flexion or extension (weakest) (physician) | Normal = 0 | Mild weakness = 1 | Moderate weakness (i.e., ~50% weak, +/- 15%) = 3 | Severe weakness = 4 |
| Shoulder abduction (physician) | Normal = 0 | Mild weakness = 2 | Moderate weakness (i.e., ~50% | Severe weakness = 5 |
| Hip flexion (physician) | Normal = 0 | Mild weakness = 2 | Moderate weakness (i.e., ~50% weak, +/- 15%) | Severe weakness = 5 |

Total Score:

Please note that "moderate weakness" for neck and limb items should be construed as weakness that equals roughly 50% +/- 15% of expected normal strength. Any weakness milder than that would be "mild" and any weakness more severe than that would be classified as "severe".

Fig. 6

The 15-Item Quality of Life Scale for Myasthenia Gravis

| Please indicate how true each statement has been (over the past few weeks) | Not at all 0 | Somewhat 1 | Very much 2 |
|---|---|---|---|
| 1. I am frustrated by my MG | | | |
| 2. I have trouble with my eyes because of my MG (e.g., double vision) | | | |
| 3. I have trouble eating because of MG | | | |
| 4. I have limited my social activity because of my MG | | | |
| 5. My MG limits my ability to enjoy hobbies and fun activities | | | |
| 6. I have trouble meeting the needs of my family because of my MG | | | |
| 7. I have to make plans around my MG | | | |
| 8. I am bothered by limitations in performing my work (include work at home) because of my MG | | | |
| 9. I have difficulty speaking due to MG | | | |
| 10. I have lost some personal independence because of my MG (e.g., driving, shopping, running errands) | | | |
| 11. I am depressed about my MG | | | |
| 12. I have trouble walking due to MG | | | |
| 13. I have trouble getting around public places because of my MG | | | |
| 14. I feel overwhelmed by my MG | | | |
| 15. I have trouble performing my personal grooming needs due to MG | | | |

USE OF FCRN ANTAGONISTS FOR TREATMENT OF GENERALIZED MYASTHENIA GRAVIS

RELATED APPLICATIONS

This application claims priority to U.S. Provisional Application No. 62/596,562, entitled "Use of FcRn Antagonists for Treatment of Generalized Myasthenia Gravis", filed Dec. 8, 2017, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 7, 2018, is named 607492_AGX5-033_ST25.txt and is 16,667 obytes in size.

BACKGROUND

Myasthenia gravis (MG) is an autoimmune disorder characterized in most cases by T cell and antibody responses to neuromuscular junction (NMJ) proteins such as skeletal muscle nicotinic acetylcholine receptor (AChR) or, less frequently, a muscle-specific tyrosine kinase (MuSK) involved in AChR clustering. The disease affects males and females in equal ratio although the incidence in females peaks in the 3rd decade as compared to males in whom the peak age at onset is in the 6th or 7th decade. Mortality from MG is approximately 4%, mostly due to respiratory failure. Approximately 60,000 (14-20 per 100,000) of U.S. individuals are affected.

Antibodies, especially IgG, play a predominant role in the pathogenesis and the treatment of MG. High-affinity anti-AChR antibodies bind to the muscle endplate, leading to AChR dysfunction or loss via activation of complement, cross-linking of AChR receptors, or direct blockade of acetylcholine binding sites, thereby leading to an impaired signal transduction and resulting muscle weakness. The muscle weakness fluctuates with activity, and periods of rest offer only a temporary reprieve. MG may initially present with ocular muscle weakness affecting eye and eyelid movement, referred to as ocular MG (oMG). Ten percent of subjects have disease limited to ocular muscles. Ninety percent of subjects have generalized MG (gMG), with muscle weakness involving neck, head, spine, bulbar, respiratory, and/or limb muscles. Bulbar weakness refers to muscles controlled by nerves originating from the bulb-like part of the brainstem and manifests as difficulty in talking, chewing, swallowing, and control of the head. MG may cause life-threatening respiratory failure, referred to as myasthenic crisis. About 15% to 20% of subjects will experience a myasthenic crisis during the course of their disease, 75% within 2 years of diagnosis, requiring hospitalization and ventilatory support.

Generalized MG is typically managed with acetylcholinesterase inhibitors and immunosuppressive therapies (ISTs). Acute exacerbations are treated using either therapeutic plasma exchange (PE), immunoadsorption (IA) or intravenous immunoglobulin (IVIg). However, these therapeutic options can suffer from severe side effects and/or comorbidities. Moreover, some subjects do not respond adequately to ISTs, or cannot tolerate ISTs, and those who require repeated treatments with plasma exchange (PE) and/or intravenous immunoglobulin (IVIg) to maintain clinical stability.

Thus, there is an urgent need in the art for new therapeutic approaches to rapidly clear pathogenic anti-AChR autoantibodies in MG.

SUMMARY

The present disclosure provides novel methods of treating myasthenia gravis, including generalized myasthenia gravis, in a subject. These methods generally comprise administering to the subject an effective amount of an isolated FcRn antagonist that binds specifically to FcRn with increased affinity and reduced pH dependence relative to native Fc region. The disclosed methods are particularly useful for treating antibody-mediated disorders such as generalized myasthenia gravis.

Accordingly, in one aspect, the instant disclosure provides a method of treatment of myasthenia gravis, e.g., generalized myasthenia gravis, in a subject, the method comprising administering to the subject an effective amount of an isolated FcRn antagonist. The instant disclosure also provides an isolated FcRn antagonist for use in treating myasthenia gravis, e.g., generalized myasthenia gravis in a subject. The instant disclosure further provides use of an isolated FcRn antagonist, as described herein, in the manufacture of a medicament for the treatment of myasthenia gravis, e.g., generalized myasthenia gravis.

In an embodiment, the isolated FcRn antagonist comprises a variant Fc region, or FcRn-binding fragment thereof.

In certain embodiments, the Fc domains of the variant Fc region comprise the amino acids Y, T, E, K, F, and Y at EU positions 252, 254, 256, 433, 434, and 436 respectively.

In certain embodiments, the FcRn antagonist is an anti-FcRn antibody comprising an antigen binding region comprising variable domains which specifically bind human FcRn.

In certain embodiments, the FcRn antagonist does not comprise an antibody variable region. In certain embodiments, the FcRn antagonist does not comprise a CH1 domain. In certain embodiments, the FcRn antagonist does not comprise a free cysteine residue.

In certain embodiments, the variant Fc region is a variant IgG Fc region. In certain embodiments, the variant Fc region is a variant IgG1 Fc region. In certain embodiments, the variant Fc region is a variant human IgG Fc region.

In certain embodiments, the amino acid sequence of the Fc domains of the variant Fc region comprises an amino acid sequence selected from the group consisting of SEQ ID NOs: 1, 2, and 3.

In certain embodiments, the amino acid sequence of the Fc domains of the variant Fc region consists of the amino acid sequence set forth in SEQ ID NO: 1.

In certain embodiments, the amino acid sequence of the Fc domains of the variant Fc region consists of the amino acid sequence set forth in SEQ ID NO: 2.

In certain embodiments, the amino acid sequence of the Fc domains of the variant Fc region consists of the amino acid sequence set forth in SEQ ID NO: 3.

In certain embodiments, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 1.

In certain embodiments, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2.

In certain embodiments, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 3.

In certain embodiments, the variant Fc region has an increased affinity for an Fc gamma receptor (FcγR) relative to the affinity of a wild-type IgG1 Fc region for the Fc gamma receptor.

In certain embodiments, the variant Fc region binds to FcRn with increased affinity and reduced pH dependence relative to a native Fc region, for example a wild-type IgG Fc region, preferably a wild-type IgG1 Fc region.

In certain embodiments, the variant Fc region has increased affinity for CD16a. In certain embodiments, the variant Fc region does not have increased affinity for CD16a.

In certain embodiments, the Fc domains of the variant Fc region comprise an N-linked glycan at EU position 297.

In certain embodiments, the Fc domains of the variant Fc region comprise a fucosylated N-linked glycan at EU position 297.

In certain embodiments, the Fc domains of the variant Fc region comprise an N-linked glycan having a bisecting GlcNAc at EU position 297.

In certain embodiments, the Fc domains of the variant Fc region comprise an afucosylated N-linked glycan at EU position 297.

In certain embodiments, the FcRn antagonist comprises a plurality of FcRn antagonist molecules, wherein at least 50% of the plurality of FcRn antagonist molecules comprise a variant Fc region or FcRn-binding fragment thereof.

In certain embodiments, the FcRn antagonist is administered to the subject at least twice in 22 days.

In certain embodiments, the FcRn antagonist is administered to the subject 1, 2, 3, 4, 5, 6, 7, 8, 9, 10, 11, 12, 13, 14, 15, 16, 17, 18, 19, 20, 21, or 22 times in 22 days. In certain embodiments, the FcRn antagonist is administered to the subject at a frequency of once every 1, 2, 3, 4, 5, 6, 7, 8, 9, 10, 11, 12, 13, 14, 15, 16, 17, 18, 19, 20, 21, or 22 days. In certain embodiments, the FcRn antagonist is administered to the subject at a frequency of once every 3 days. In certain embodiments, the FcRn antagonist is administered to the subject at a frequency of once every 7 days.

In certain embodiments, the FcRn antagonist is administered to the subject in a dose of between about 1 and about 200 mg/kg. In certain embodiments, the FcRn antagonist is administered to the subject in a dose of about 1, 2, 3, 5, 10, 20, 25, 30, 50, 70, 100, or 200 mg/kg. In certain embodiments, the FcRn antagonist is administered to the subject in a dose of about 5 mg/kg. In certain embodiments, the FcRn antagonist is administered to the subject in a dose of about 10 mg/kg. In certain embodiments, the FcRn antagonist is administered to the subject in a dose of about 20 mg/kg. In certain embodiments, the FcRn antagonist is administered to the subject in a dose of about 25 mg/kg.

In certain embodiments, the FcRn antagonist is administered to the subject in a dose selected from the group consisting of about 150, 300, 450, 600, 750, 900, 1050, and 1200 mg.

In certain embodiments, the FcRn antagonist is administered to the subject in a dose of about 150 mg.

In certain embodiments, the FcRn antagonist is administered to the subject in a dose of about 300 mg.

In certain embodiments, the FcRn antagonist is administered to the subject in a dose of about 450 mg.

In certain embodiments, at least one additional dose of the FcRn antagonist is administered to the subject. For example, treatment with the FcRn antagonist can continue on a chronic basis, e.g., weekly, biweekly, monthly, bimonthly, etc.

In certain embodiments, the FcRn antagonist is administered intravenously. In certain embodiments, the FcRn antagonist is administered subcutaneously. In certain embodiments, a first dose is administered to the subject intravenously, and one or more subsequent doses are administered subcutaneously. In certain aspects, the invention provides a method of treating generalized myasthenia gravis in a subject, the method comprising administering to the subject an isolated FcRn antagonist using a phased dosing schedule with an induction phase comprising about 1-5 doses of the isolated FcRn antagonist within 1 month, followed by a maintenance phase comprising a dose of FcRn antagonist every week (q1w), every two weeks (q2w), every three weeks (q3w), or every 4 weeks (q4w) thereafter, thereby treating the generalized myasthenia gravis in the subject. The invention also provides an isolated FcRn antagonist for use in treating myasthenia gravis in a subject, wherein the subject is administered the isolated FcRn antagonist using a phased dosing schedule with an induction phase comprising about 1-5 doses of the isolated FcRn antagonist within 1 month, followed by a maintenance phase comprising a dose of FcRn antagonist every week (q1w), every two weeks (q2w), every three weeks (q3w), or every 4 weeks (q4w) thereafter.

In certain embodiments, the induction phase comprises administration of 1, 2, 3, 4, or 5 doses of about 5 mg/kg, about 10 mg/kg, about 15 mg/kg or about 20 mg/kg of FcRn antagonist, In certain embodiments, the 1-5 doses of the induction phase are administered intravenously (i.v.).

In certain embodiments, the maintenance phase doses comprise a fixed dose of about 150 mg or about 300 mg of FcRn antagonist. In certain embodiments, the maintenance phase doses are administered on an as-needed basis depending on clinical symptoms or clinical status of the subject. In certain embodiments, the maintenance phase doses are administered subcutaneously (s.c.) to the subject.

In certain embodiments, the first 1, 2, 3, or 4 doses are administered to the subject intravenously, and 1, 2, 3, or 4 subsequent doses are administered to the subject subcutaneously.

In certain embodiments, the first 4 doses are administered to the subject intravenously, and 1, 2, 3, or 4 subsequent doses are administered to the subject subcutaneously.

In certain embodiments, 1 dose is administered to the subject intravenously, and 4 subsequent doses are administered to the subject subcutaneously.

In certain embodiments, 2 doses are administered to the subject intravenously, and 4 subsequent doses are administered to the subject subcutaneously.

In one aspect, the instant disclosure provides a method of treating generalized myasthenia gravis in a subject, the method comprising administering to the subject a plurality of doses of an isolated FcRn antagonist, wherein one or more doses of the FcRn antagonist are administered intravenously to the subject in a dose of about 10 mg/kg per dose, and one or more subsequent doses of the FcRn antagonist are administered subcutaneously to the subject in a dose of about 150 mg per dose, thereby treating the generalized myasthenia gravis in the subject. The instant disclosure also provides an isolated FcRn antagonist for use in treating generalized myasthenia gravis in a subject, wherein the subject is administered a plurality of doses of the isolated FcRn antagonist, wherein one or more doses of the FcRn antagonist are administered intravenously to the subject in a dose of about 10 mg/kg per dose, and one or more subsequent doses of the FcRn antagonist are administered subcutaneously to the subject in a dose of about 150 mg per dose.

In one aspect, the instant disclosure provides a method of treating generalized myasthenia gravis in a subject, the method comprising administering to the subject more than one dose of an isolated FcRn antagonist, wherein one or more doses of the FcRn antagonist are administered intravenously to the subject in a dose of about 10 mg/kg per dose, and one or more subsequent doses of the FcRn antagonist are administered subcutaneously to the subject in a dose of about 300 mg per dose, thereby treating the generalized myasthenia gravis in the subject. The instant disclosure also provides an isolated FcRn antagonist for use in treating generalized myasthenia gravis in a subject, wherein the subject is administered more than one dose of the isolated FcRn antagonist, wherein one or more doses of the FcRn antagonist are administered intravenously to the subject in a dose of about 10 mg/kg per dose, and one or more subsequent doses of the FcRn antagonist are administered subcutaneously to the subject in a dose of about 300 mg per dose.

In certain embodiments, 1, 2, 3, or 4 doses are administered to the subject intravenously, and wherein 1, 2, 3, or 4 subsequent doses are administered to the subject subcutaneously.

In certain embodiments, 1 dose is administered to the subject intravenously and 1 subsequent dose is administered to the subject subcutaneously.

In certain embodiments, 1 dose is administered to the subject intravenously and 2 subsequent doses are administered to the subject subcutaneously.

In certain embodiments, 1 dose is administered to the subject intravenously and 3 subsequent doses are administered to the subject subcutaneously.

In certain embodiments, 1 dose is administered to the subject intravenously and 4 subsequent doses are administered to the subject subcutaneously.

In certain embodiments, 2 doses are administered to the subject intravenously and 1 subsequent dose is administered to the subject subcutaneously.

In certain embodiments, 2 doses are administered to the subject intravenously and 2 subsequent doses are administered to the subject subcutaneously.

In certain embodiments, 2 doses are administered to the subject intravenously and 3 subsequent doses are administered to the subject subcutaneously.

In certain embodiments, 2 doses are administered to the subject intravenously and 4 subsequent doses are administered to the subject subcutaneously.

In certain embodiments, 3 doses are administered to the subject intravenously and 1 subsequent dose is administered to the subject subcutaneously.

In certain embodiments, 3 doses are administered to the subject intravenously and 2 subsequent doses are administered to the subject subcutaneously.

In certain embodiments, 3 doses are administered to the subject intravenously and 3 subsequent doses are administered to the subject subcutaneously.

In certain embodiments, 3 doses are administered to the subject intravenously and 4 subsequent doses are administered to the subject subcutaneously.

In certain embodiments, 4 doses are administered to the subject intravenously and 1 subsequent dose is administered to the subject subcutaneously.

In certain embodiments, 4 doses are administered to the subject intravenously and 2 subsequent doses are administered to the subject subcutaneously.

In certain embodiments, 4 doses are administered to the subject intravenously and 3 subsequent doses are administered to the subject subcutaneously.

In certain embodiments, 4 doses are administered to the subject intravenously and 4 subsequent doses are administered to the subject subcutaneously.

In certain embodiments, the one or more subcutaneous doses are administered at a frequency selected from the group consisting of about daily, about weekly, about biweekly, and about monthly.

In certain embodiments, one or more doses of the FcRn antagonist are administered as a retreatment, a maintenance dose, or a tapering dose.

In certain embodiments, the FcRn antagonist is administered to the subject simultaneously with an additional therapeutic agent. In certain embodiments, the FcRn antagonist is administered to the subject sequentially with an additional therapeutic agent.

In certain embodiments, the dosage of the additional therapeutic agent is tapered in conjunction with treatment with the FcRn antagonist.

In certain embodiments, administration of the isolated FcRn antagonist treats one or more exacerbations of the generalized myasthenia gravis.

In certain embodiments, administration of the isolated FcRn antagonist improves one or more clinical symptoms of the generalized myasthenia gravis selected from the group consisting of ocular muscle fatigue or weakness, skeletal muscle fatigue or weakness, respiratory muscle fatigue or weakness, disabling fatigue, slurred speech, choking, impaired swallowing, double or blurred vision, immobility requiring assistance, shortness of breath, and respiratory failure.

In certain embodiments, administration of the isolated FcRn antagonist improves one or more therapeutic evaluation scores in the subject selected from the group consisting of Quantitative Myasthenia Gravis (QMG) score, Myasthenia Gravis activities of daily living (MG-ADL) score, Myasthenia Gravis composite (MGC) score, 15-item Quality of life scale for Myasthenia Gravis (MGQoL15r), and EuroQoL15 Dimension (EQ-5D) score.

In certain embodiments, the score on at least one scale selected from the group consisting of QMG, MG-ADL, MGC, MGQol 15r, and EQ-5D is improved by at least one point at day 8, 15, 22, 29, or 36 compared to a baseline score as measured using the same scale prior to administration of the isolated FcRn antagonist at day 1.

In certain embodiments, the QMG score is improved at day 8, 15, 22, 29, or 36 compared to a baseline QMG score as measured prior to administration of the isolated FcRn antagonist at day 1. In certain embodiments, the QMG score is decreased by at least 3 points at day 8, 15, 22, 29, or 36 compared to a baseline QMG score as measured prior to administration of the isolated FcRn antagonist at day 1. In certain embodiments, the QMG score is decreased by at least 4 points at day 8, 15, 22, 29, or 36 compared to a baseline QMG score as measured prior to administration of the isolated FcRn antagonist at day 1.

In certain embodiments, the MG-ADL score is improved at day 8, 15, 22, 29, or 36 compared to a baseline MG-ADL score as measured prior to administration of the isolated FcRn antagonist at day 1. In certain embodiments, the MG-ADL score is decreased by at least 2 points at day 8, 15, 22, 29, or 36 compared to a baseline MG-ADL score as measured prior to administration of the isolated FcRn antagonist at day 1. In certain embodiments, the MG-ADL score is decreased by at least 3 points at day 8, 15, 22, 29, or 36 compared to a baseline MG-ADL score as measured prior to administration of the isolated FcRn antagonist at day 1.

In certain embodiments, the MGC score is improved at day 8, 15, 22, 29, or 36 compared to a baseline MGC score as measured prior to administration of the isolated FcRn antagonist at day 1. In certain embodiments, the MGQoL15r score is improved at day 8, 15, 22, 29, or 36 compared to a baseline MGQoL15r score as measured prior to administration of the isolated FcRn antagonist at day 1. In certain embodiments, the EQ-5D score is improved at day 8, 15, 22, 29, or 36 compared to a baseline EQ-5D score as measured prior to administration of the isolated FcRn antagonist at day 1.

In certain embodiments, administration of the isolated FcRn antagonist reduces the serum level of at least one IgG antibody selected from the group consisting of total serum IgG, anti-acetylcholine receptor (AChR) antibody, anti-MuSK antibody, and anti-LRP4 antibody. In certain embodiments, the at least one IgG antibody is total serum IgG antibody. In certain embodiments, the at least one IgG antibody is an anti-AChR antibody. In certain embodiments, the at least one IgG antibody is an anti-MuSK antibody. In certain embodiments, the at least one IgG antibody is an anti-LRP4 antibody.

In certain embodiments, the FcRn antagonist is administered to the subject 1, 2, 3, 4, 5, 6, 7, 8, 9, 10, 11, 12, 13, 14, 15, 16, 17, 18, 19, 20, 21, or 22 times in 22 days, and the serum level of the at least one IgG antibody is reduced at day 8, 15, 22, 29, or 36 compared to a baseline serum level of the at least one IgG antibody as measured prior to administration of the isolated FcRn antagonist at day 1. In certain embodiments, the serum level of the at least one IgG antibody is reduced by at least about 25% at day 8, 15, 22, 29, or 36. In certain embodiments, the serum level of the at least one IgG antibody is reduced by at least about 50% at day 8, 15, 22, 29, or 36.

In certain embodiments, the subject has a QMG score of at least 11 points with no more than 25% of the total points due to ocular symptoms as measured prior to first administration of the isolated FcRn antagonist.

In certain embodiments, the subject has a MG-ADL score of at least 5 points with no more than 25% of the total points due to ocular symptoms as measured prior to first administration of the isolated FcRn antagonist.

In certain embodiments, the generalized myasthenia gravis is not responsive to a standard myasthenia gravis therapy selected from the group consisting of intravenous immunoglobulin (IVIg), plasmapheresis, azathioprine, non-steroidal immunosuppressant drugs, steroids, cholinesterase inhibitors, immunoadsorption, and eculizumab.

In certain embodiments, the subject is intolerant to a standard myasthenia gravis therapy selected from the group consisting of intravenous immunoglobulin (IVIg), plasmapheresis, azathioprine, non-steroidal immunosuppressant drugs, steroids, cholinesterase inhibitors, immunoadsorption, and eculizumab.

In certain embodiments, the subject is positive for auto-antibodies binding to nicotinic acetylcholine receptor (anti-AChR) (anti-AChR antibody positive). In certain embodiments, the subject is negative for auto-antibodies binding to nicotinic acetylcholine receptor (anti-AChR) (anti-AChR antibody negative).

In certain embodiments, the subject is anti-MuSK antibody positive. In certain embodiments, the subject is anti-MuSK antibody negative.

In certain embodiments, the subject is anti-LRP4 antibody positive. In certain embodiments, the subject is anti-LRP4 antibody negative. In certain embodiments, the subject is a human. In certain embodiments, the subject is an adult human.

An aspect of the invention is a method of treating generalized myasthenia gravis (MG) in a subject, the method comprising administering to the subject an effective amount of an isolated FcRn antagonist, thereby treating MG in the subject, wherein:
    the subject, prior to first administration of the isolated FcRn antagonist, has confirmed diagnosis generalized MG, has Class II-IVa disease according to the Myasthenia Gravis Foundation of America (MGFA) classification system, and has an MG-ADL score of at least 5 with more than 50% of the score attributable to non-ocular items,
    the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and
    the isolated FcRn antagonist is administered to the subject in a dose of about 10 mg/kg.

Also provided in accordance with this aspect of the invention is an isolated FcRn antagonist for use in a method of treating myasthenia gravis (MG) in a subject, the method comprising administering to the subject an effective amount of the isolated FcRn antagonist, thereby treating MG in the subject, wherein:
    the subject, prior to first administration of the isolated FcRn antagonist, has confirmed diagnosis generalized MG, has Class II-IVa disease according to the Myasthenia Gravis Foundation of America (MGFA) classification system, and has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and
    the isolated FcRn antagonist is administered to the subject in a dose of about 10 mg/kg.

An aspect of the invention is a method of treating generalized myasthenia gravis in a subject, the method comprising administering to the subject an isolated FcRn antagonist using a phased dosing schedule with an induction phase comprising about 1-5 doses of the isolated FcRn antagonist within 1 month, followed by a maintenance phase comprising a dose of FcRn antagonist every week (q1w), every two weeks (q2w), every three weeks (q3w), or every 4 weeks (q4w) thereafter, thereby treating the generalized myasthenia gravis in the subject, wherein:
    the subject, prior to first administration of the isolated FcRn antagonist, has confirmed diagnosis generalized MG, has Class II-IVa disease according to the Myasthenia Gravis Foundation of America (MGFA) classification system, and has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

Also provided in accordance with this aspect of the invention is an isolated FcRn antagonist for use in a method of treating myasthenia gravis (MG) in a subject, the method comprising administering to the subject the isolated FcRn antagonist using a phased dosing schedule with an induction phase comprising about 1-5 doses of the isolated FcRn antagonist within 1 month, followed by a maintenance phase comprising a dose of FcRn antagonist every week (q1w), every two weeks (q2w), every three weeks (q3w), or every 4 weeks (q4w) thereafter, thereby treating the generalized myasthenia gravis in the subject, wherein:

the subject, prior to first administration of the isolated FcRn antagonist, has confirmed diagnosis generalized MG, has Class II-IVa disease according to the Myasthenia Gravis Foundation of America (MGFA) classification system, and has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

An aspect of the invention is a method of treating generalized myasthenia gravis in a subject, the method comprising administering to the subject an isolated FcRn antagonist using a phased dosing schedule with an induction phase comprising about 1-5 doses of the isolated FcRn antagonist within 1 month, followed by a maintenance phase comprising one or more cycles as needed based on clinical need thereafter, each cycle comprising administering to the subject about 1-5 doses of the isolated FcRn antagonist within 1 month, thereby treating the generalized myasthenia gravis in the subject, wherein:

the subject, prior to first administration of the isolated FcRn antagonist in the induction phase, has confirmed diagnosis generalized MG, has Class II-IVa disease according to the Myasthenia Gravis Foundation of America (MGFA) classification system, and has an MG-ADL score of at least 5 with more than 50% of the score attributable to non-ocular items, the subject, prior to first administration of the isolated FcRn antagonist in any cycle of the maintenance phase, has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

Also provided in accordance with this aspect of the invention is an isolated FcRn antagonist for use in a method of treating myasthenia gravis (MG) in a subject, the method comprising administering to the subject the isolated FcRn antagonist using a phased dosing schedule with an induction phase comprising about 1-5 doses of the isolated FcRn antagonist within 1 month, followed by a maintenance phase comprising one or more cycles as needed based on clinical need thereafter, each cycle comprising administering to the subject about 1-5 doses of the isolated FcRn antagonist within 1 month, thereby treating the generalized myasthenia gravis in the subject, wherein:

the subject, prior to first administration of the isolated FcRn antagonist in the induction phase, has confirmed diagnosis generalized MG, has Class II-IVa disease according to the Myasthenia Gravis Foundation of America (MGFA) classification system, and has an MG-ADL score of at least 5 with more than 50% of the score attributable to non-ocular items, the subject, prior to first administration of the isolated FcRn antagonist in any cycle of the maintenance phase, has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

In certain embodiments in accordance with each of the foregoing aspects and embodiments, the subject is an adult human with generalized myasthenia gravis.

In certain embodiments in accordance with each of the foregoing aspects and embodiments, the subject is an adult human with generalized myasthenia gravis whose symptoms are inadequately controlled with acetylcholinesterase inhibitors, steroids, or immunosuppressive therapies.

In certain embodiments in accordance with each of the foregoing aspects and embodiments, the subject is an adult human with generalized myasthenia gravis who is positive for auto-antibodies binding to nicotinic acetylcholine receptor (anti-AChR).

In certain embodiments in accordance with each of the foregoing aspects and embodiments, the subject is an adult human with generalized myasthenia gravis who is positive for auto-antibodies binding to nicotinic acetylcholine receptor (anti-AChR antibodies) and whose symptoms are inadequately controlled with acetylcholinesterase inhibitors, steroids, or immunosuppressive therapies.

Alternatively, in certain embodiments in accordance with each of the foregoing aspects and embodiments, the subject is an adult human with generalized myasthenia gravis who is negative for auto-antibodies binding to nicotinic acetylcholine receptor (anti-AChR).

Alternatively, in certain embodiments in accordance with each of the foregoing aspects and embodiments, the subject is an adult human with generalized myasthenia gravis who is negative for auto-antibodies binding to nicotinic acetylcholine receptor (anti-AChR) and whose symptoms are inadequately controlled with acetylcholinesterase inhibitors, steroids, or immunosuppressive therapies.

Alternatively, in certain embodiments in accordance with each of the foregoing aspects and embodiments, the subject is an adult human with generalized myasthenia gravis who is positive for auto-antibodies binding to nicotinic acetylcholine receptor (anti-AChR) and positive for auto-antibodies binding to muscle-specific kinase (MuSK).

Alternatively, in certain embodiments in accordance with each of the foregoing aspects and embodiments, the subject is an adult human with generalized myasthenia gravis who is positive for auto-antibodies binding to nicotinic acetylcholine receptor (anti-AChR) and positive for auto-antibodies binding to muscle-specific kinase (MuSK) and whose symptoms are inadequately controlled with acetylcholinesterase inhibitors, steroids, or immunosuppressive therapies.

Alternatively, in certain embodiments in accordance with each of the foregoing aspects and embodiments, the subject is an adult human with generalized myasthenia gravis who is negative for auto-antibodies binding to nicotinic acetylcholine receptor (anti-AChR) and negative for auto-antibodies binding to muscle-specific kinase (MuSK).

Alternatively, in certain embodiments in accordance with each of the foregoing aspects and embodiments, the subject is an adult human with generalized myasthenia gravis who is negative for auto-antibodies binding to nicotinic acetylcholine receptor (anti-AChR) and negative for auto-antibodies binding to muscle-specific kinase (MuSK) and whose symptoms are inadequately controlled with acetylcholinesterase inhibitors, steroids, or immunosuppressive therapies.

BRIEF DESCRIPTION OF THE DRAWINGS

FIG. 2 is a table of the schedule of assessments for the ARGX-113-1602 Phase II clinical trial protocol.

FIG. 3 is a table to assess MG symptoms using the Myasthenia Gravis-Activities (MG-ADL) assessment criteria.

FIG. 4 depicts the Quantitative Myasthenia Gravis (QMG) Testing Form.

FIG. 5 depicts the Myasthenia Gravis Composite (MGC) Score sheet.

FIG. 6 is a table to assess the 15-Item Quality of Life Scale for Myasthenia Gravis (MGQoL15r).

DETAILED DESCRIPTION

Figure 1:
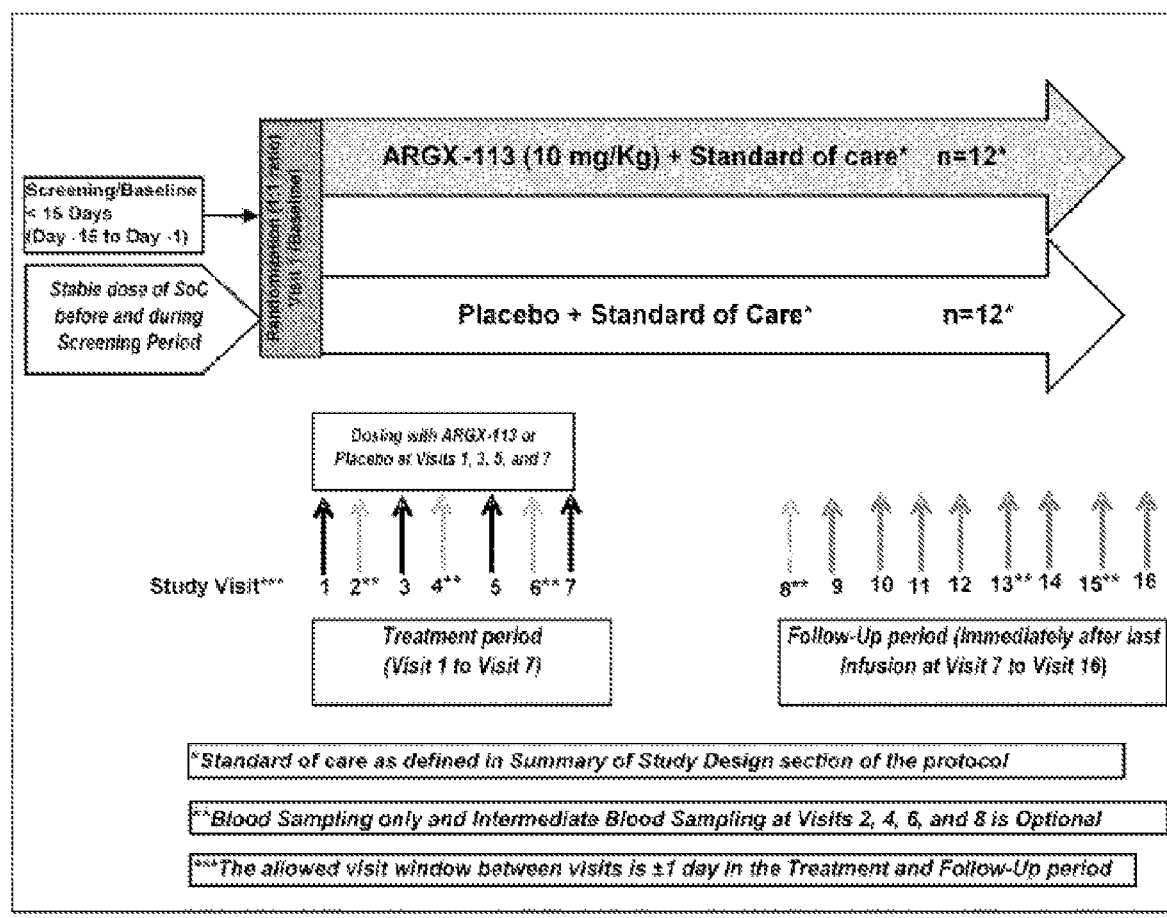
FIG. 1 depicts a schematic of the study design for the ARGX-113-1602 Phase II clinical trial protocol.

The present disclosure provides novel methods of treating myasthenia gravis, including in particular generalized myasthenia gravis, in a subject. These methods generally comprise administering to the subject an effective amount of an isolated FcRn antagonist. In certain embodiments, the isolated FcRn antagonist binds specifically to FcRn with increased affinity and reduced pH dependence relative to native Fc region. In certain embodiments, the isolated FcRn antagonist binds specifically to FcRn with increased affinity and reduced pH dependence relative to a wild-type IgG Fc region. In certain embodiments, the isolated FcRn antagonist binds specifically to FcRn with increased affinity and reduced pH dependence relative to a wild-type IgG1 Fc region.

I. Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art.

In order that the present invention may be more readily understood, certain terms are first defined.

As used herein the term "FcRn antagonist" refers to any agent comprising an Fc region (e.g., a variant Fc region disclosed herein) that binds specifically to FcRn through the Fc region and inhibits the binding of immunoglobulin to FcRn, with the proviso that the agent is not a naturally occurring antibody. In certain embodiments, the FcRn antagonist is not a full length IgG antibody. In certain embodiments, the FcRn antagonist is a monoclonal antibody. In certain embodiments, the FcRn antagonist is a monoclonal antibody characterized by complementarity determining regions (CDRs) specific for FcRn. In certain embodiments, the FcRn antagonist is ARGX-113.

As used herein, the term "Fc region" refers to the portion of a native immunoglobulin formed by the Fc domains of its two heavy chains. A native Fc region is homodimeric.

As used herein, the term "variant Fc region" refers to an Fc region with one or more alterations relative to a native Fc region. Alteration can include amino acid substitutions, additions and/or deletions, linkage of additional moieties, and/or alteration the native glycans. In certain embodiments the term encompasses homodimeric Fc regions where each of the constituent Fc domains is the same. In certain embodiments the term encompasses heterodimeric Fc regions where each of the constituent Fc domains is different. Examples of such heterodimeric Fc regions include, without limitation, Fc regions made using the "knobs and holes" technology as described in, for example, U.S. Pat. No. 8,216,805, which is incorporated by reference herein in its entirety. The term also encompasses single chain Fc regions where the constituent Fc domains are linked together by a linker moiety, as described in, for example, US Pat. Appl. Pub. 2009/0252729A1 and US Pat. Appl. Pub. 2011/0081345A1, which are each incorporated by reference herein in their entirety.

As used herein, the term "Fc domain" refers to the portion of a single immunoglobulin heavy chain beginning in the hinge region just upstream of the papain cleavage site and ending at the C-terminus of the antibody. Accordingly, a complete Fc domain comprises at least a portion of a hinge (e.g., upper, middle, and/or lower hinge region) domain, a CH2 domain, and a CH3 domain.

As used herein the term "FcRn binding fragment" refers to a portion of an Fc region that is sufficient to confer FcRn binding.

As used herein, the term "antibody" refers to immunoglobulin molecules comprising four polypeptide chains, two heavy (H) chains and two light (L) chains interconnected by disulfide bonds, as well as multimers thereof (e.g., IgM). Each heavy chain comprises a heavy chain variable region (abbreviated VH) and a heavy chain constant region. The heavy chain constant region comprises three domains, CH1, CH2 and CH3. Each light chain comprises a light chain variable region (abbreviated VL) and a light chain constant region. The light chain constant region comprises one domain (CL). The VH and VL regions can be further subdivided into regions of hypervariability, termed complementarity determining regions (CDRs), interspersed with regions that are more conserved, termed framework regions (FR).

As used herein, the term "binding site" comprises a region of a polypeptide which is responsible for selectively binding to a target antigen of interest (e.g., AChR). Binding domains comprise at least one binding site. Exemplary binding domains include an antibody variable domain. Antibody molecules may comprise a single binding site or multiple (e.g., two, three or four) binding sites.

The terms "variable region" and "variable domain" are used herein interchangeable and are intended to have equivalent meaning. The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1(λ), L2(λ) and L3(λ) and may be defined as comprising residues 24-33 (L1(λ), consisting of 9, 10 or 11 amino acid residues), 49-53 (L2(λ), consisting of 3 residues) and 90-96 (L3(λ), consisting of 5 residues) in the VL domain (Morea et al., Methods 20: 267-279 (2000)). The first, second and third hypervariable loops of the VKappa light chain domain are referred to herein as L1(κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the VL domain (Morea et al., Methods 20: 267-279 (2000)). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20: 267-279 (2000)).

Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including γ, ε, δ, α, or μ.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, MD, 1983) and the limits of the HVs and the CDRs may be different in some VH and VL domains.

The CDRs of the VL and VH domains can typically be defined as comprising the following amino acids: residues 24-34 (CDRL1), 50-56 (CDRL2) and 89-97 (CDRL3) in the light chain variable domain, and residues 31-35 or 31-35b (CDRH1), 50-65 (CDRH2) and 95-102 (CDRH3) in the heavy chain variable domain; (Kabat et al., Sequences of Proteins of Immunological Interest, 5th Ed. Public Health Service, National Institutes of Health, Bethesda, MD (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol. 215: 175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

As used herein, the term "CDR" or "complementarity determining region" means the non-contiguous antigen combining sites found within the variable region of both heavy and light chain polypeptides. These particular regions have been described by Kabat et al., J. Biol. Chem. 252: 6609-6616 (1977); Kabat et al., Sequences of protein of immunological interest. (1991); Chothia et al., J. Mol. Biol. 196: 901-917 (1987); and by MacCallum et al., J. Mol. Biol. 262: 732-745 (1996) where the definitions include overlapping or subsets of amino acid residues when compared against each other. The amino acid residues which encompass the CDRs as defined by each of the above cited references are set forth for comparison in Table 1. Preferably, the term "CDR" is a CDR as defined by Kabat based on sequence comparisons.

TABLE 1

CDR definitions

|  | Kabat | Chothia | MacCallum |
|---|---|---|---|
| VHCDR1 | 31-35 | 26-32 | 30-35 |
| VHCDR2 | 50-65 | 53-55 | 47-58 |
| VHCDR3 | 95-102 | 96-101 | 93-101 |
| VLCDR1 | 24-34 | 26-32 | 30-36 |
| VLCDR2 | 50-56 | 50-52 | 46-55 |
| VLCDR3 | 89-97 | 91-96 | 89-96 |

The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94; and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the noncovalent binding of the antibody to the immunoreactive antigen epitope. The position of CDRs can be readily identified by one of ordinary skill in the art.

As used herein, the term "EU position" refers to the amino acid position in the EU numbering convention for the Fc region described in Edelman, G. M. et al., Proc. Natl. Acad. Sci. USA, 63: 78-85 (1969) and Kabat et al., in "Sequences of Proteins of Immunological Interest", U.S. Dept. Health and Human Services, 5th edition, 1991.

As used herein, the term "CH1 domain" refers to the first (most amino terminal) constant region domain of an immunoglobulin heavy chain that extends from about EU positions 118-215. The CH1 domain is adjacent to the VH domain and amino terminal to the hinge region of an immunoglobulin heavy chain molecule, and does not form a part of the Fc region of an immunoglobulin heavy chain.

As used herein, the term "hinge region" refers to the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161: 4083 (1998)). The FcRn antagonists of the instant disclosure can include all or a portion of a hinge region.

As used herein, the term "CH2 domain" refers to the portion of a heavy chain immunoglobulin molecule that extends from about EU positions 231-340.

As used herein, the term "CH3 domain" includes the portion of a heavy chain immunoglobulin molecule that extends approximately 110 residues from C-terminus of the CH2 domain, e.g., from about position 341-446 (EU numbering system).

As used herein, the term "FcRn" refers to a neonatal Fc receptor. Exemplary FcRn molecules include human FcRn encoded by the FCGRT gene as set forth in RefSeq NM_004107.

As used herein, the term "CD16" refers to FcγRIII Fc receptors that are required for Antibody-Dependent Cell-mediated Cytotoxicity (ADCC). Exemplary CD16 molecules include human CD16a as set forth in RefSeq NM_000569.

As used herein, the term "free cysteine" refers to native or engineered cysteine amino acid residue that exists in a substantially reduced form in a mature FcRn antagonist.

As used herein the term "N-linked glycan" refers to the N-linked glycan attached to the nitrogen (N) in the side chain of asparagine in the sequon (i.e., Asn-X-Ser or Asn-X-Thr sequence, where X is any amino acid except proline) present in the CH2 domain of an Fc region. Such N-glycans are fully described in, for example, Drickamer K and Taylor M E (2006) Introduction to Glycobiology, 2nd ed., which is incorporated herein by reference in its entirety.

As used herein the term "afucosylated" refers to an N-linked glycan which lacks a core fucose molecule as described in U.S. Pat. No. 8,067,232, the contents of which is incorporated by reference herein in its entirety.

As used herein the term "bisecting GlcNAc" refers to an N-linked glycan having an N-acetylglucosamine (GlcNAc) molecule linked to a core mannose molecule, as described in U.S. Pat. No. 8,021,856, the contents of which is incorporated by reference herein in its entirety.

As used herein, the term "antibody-mediated disorder" refers to any disease or disorder caused or exacerbated by the presence of an antibody in a subject.

As used herein, the term "treat," "treating," and "treatment" refer to therapeutic or preventative measures described herein. The methods of "treatment" employ administration to a subject, for example, a subject having an antibody-mediated disease or disorder (e.g. autoimmune disease such as myasthenia gravis) or predisposed to having such a disease or disorder, an FcRn antagonist in accordance with the present invention, in order to prevent, cure, delay, reduce the severity of, or ameliorate one or more symptoms of the disease or disorder or recurring disease or disorder, or in order to prolong the survival of a subject beyond that expected in the absence of such treatment. In certain embodiments, "treat," "treating," and "treatment" refer to reducing the severity of, or ameliorating one or more symptoms of, myasthenia gravis or generalized myasthenia gravis.

As used herein, the term "subject" refers to any human or non-human animal. In certain embodiments, the term "subject" refers to any human or non-human mammal. In certain embodiments, the subject is a human. In certain embodiments the subject is an adult human. As used herein, an "adult human" is a human who is at least 18 years of age.

As used herein, the term "immunoadhesin" refers to an antibody-like molecule, which comprises a functional domain of a binding protein (e.g., a receptor, ligand, or cell-adhesion molecule) with an Fc region.

A number of abbreviations are used herein to describe aspects of the invention. Below is a list of commonly used abbreviations.

ACh Acetylcholine
AChE Anticholinesterase inhibitor
AChR Acetylcholine receptor
ADA Anti-drug antibody
CI Confidence interval
$C_{max}$ Maximum observed plasma concentration
$C_{trough}$ Concentration observed prior to dosing
FAS Full analysis set
$G_{mean}$ Geometric mean
IV Intravenous
IVIg Intravenous immunoglobulin
MG Myasthenia gravis
MG-ADL Myasthenia gravis activities of daily living
MGC Myasthenia gravis composite score
MGFA Myasthenia Gravis Foundation of America
MG-QOL Myasthenia Gravis Quality of Life scale
MGQoL15r 15-item Quality of Life scale for Myasthenia Gravis [revised version]
PD Pharmacodynamics
PK Pharmacokinetics
QMG Quantitative Myasthenia Gravis score
SD Standard deviation
SoC Standard of care
$t_{max}$ Time of occurrence of $C_{max}$ II. Myasthenia Gravis Myasthenia gravis is a well-recognized autoimmune disease which has a reported prevalence of about at least 1 in 7500 individuals. Cardinal features are weakness and fatigability of muscles. The course of MG is often variable. Exacerbations and partial remissions may occur, particularly during the first few years after onset of the disease, and unrelated infections or systemic disorders often lead to increased myasthenic weakness.

The distribution of muscle weakness has a characteristic pattern. The cranial muscles, particularly the eyelid and extraocular muscles, are often involved early, and diplopia and ptosis are common initial symptoms. In about 85 percent of patients, the weakness becomes generalized, affecting limb muscles as well.

When the symptoms of MG are isolated to the levator palpebrae superioris, orbicularis oculi, and the oculomotor muscles, it is referred to as "ocular MG."

As used herein, the term "generalized myasthenia gravis," or equivalently "generalized MG," refers to myasthenia gravis characterized by weakness that is not limited to but can include the eyelids and extraocular muscles (levator palpebrae superioris, orbicularis oculi, and/or oculomotor muscle). In certain embodiments, the term "generalized myasthenia gravis" refers to myasthenia gravis that is characterized at least in part by weakness of at least one limb muscle. In certain embodiments, the term "generalized myasthenia gravis" refers to myasthenia gravis that is characterized at least in part by weakness of at least one extraocular muscle and weakness of at least one limb muscle. Affected muscles may include those of the eyes, face, jaw, and throat region, arm and leg (limb) muscles and muscles involved in breathing (respiratory muscles).

As used herein, an "exacerbation of myasthenia gravis" refers to an objective worsening of myasthenia gravis symptoms in subject having myasthenia gravis. Such objective worsening can be determined, for example, by serial physical examination. Alternatively or in addition, such objective worsening can be determined, for example, by serially using any one or more of the quantitative clinical assessment tools discussed below.

As used herein, an "exacerbation of generalized myasthenia gravis" refers to an objective worsening of generalized myasthenia gravis symptoms in a subject having generalized myasthenia gravis. Such objective worsening can be determined, for example, by serial physical examination. Alternatively or in addition, such objective worsening can be determined, for example, by serially using any one or more of the quantitative clinical assessment tools discussed below.

Diagnosis of MG typically can be made using one or more of the following laboratory tests. In an anticholinesterase test, the patient is administered a drug that inhibits acetylcholinesterase (AChE), such as edrophonium, following which transient, objectively improved strength in myasthenic muscles, e.g., extraocular muscles, is highly suggestive of MG. Electrodiagnostic testing, where repetitive nerve stimulation (3 Hz) results in markedly (e.g., >15%) reduced amplitude of evoked responses, is also highly suggestive of MG.

The presence of anti-AChR antibodies, which are present in approximately 80 percent of all myasthenic patients but in only about 50 percent of patients with weakness confined to the ocular muscles, is virtually diagnostic of MG. In an individual patient, a treatment-induced reduction in the antibody level often correlates with clinical improvement. AChR autoantibodies can be measured using one or more art-recognized methods including radioimmunoprecipitation and cell-based assays (see Jacob et al., Arch. Neurol., 2012; 69: 994-1001), as well as ELISA and fluorescence assays based on immunoprecipitation (see Yang et al., J. Neurol. Sci., 2011; 301: 71-76).

Approximately 5-8% of myasthenia gravis patients test positive for antibodies against muscle-specific tyrosine kinase (MuSK), a receptor tyrosine kinase. Nearly all of these patients are acetylcholine receptor (AChR) antibody-negative. El-Salem K et al., Curr Treat Options Neurol 16(4): 283 (2014). MuSK autoantibodies can be identified using art-recognized radioimmunoprecipitation and cell-based assays.

Recently, autoantibodies to low-density lipoprotein receptor-related protein 4 (LRP4) have been identified in a subset of myasthenia gravis patients without detectable anti-AChR or anti-MuSK antibodies ("double seronegative" patients). Agrin is a large proteoglycan whose best-characterized role is in the development of the neuromuscular junction during embryogenesis. LRP4 interacts with agrin, and the binding of agrin activates MuSK, which leads to the formation of most if not all postsynaptic specializations, including aggregates containing acetylcholine receptors (AChRs) in the junctional plasma membrane. Pevzner A et al., J Neurol 259(3): 427-35 (2012); Zhang B et al., Arch Neurol 69(4): 445-51 (2012).

In certain embodiments, treatment of generalized MG includes the amelioration or improvement of one or more symptoms associated with MG. Symptoms associated with MG include muscle weakness and fatigability. Muscles primarily affected by MG include muscles that control eye and eyelid movement, facial expressions, chewing, talking, swallowing, breathing, neck movements, and limb movements.

In other embodiments, treatment of MG includes the improvement of a clinical marker for MG progression. These markers include MG activity of daily living profile (MG-ADL), quantitative Myasthenia Gravis (QMG) score for disease severity, Myasthenia Gravis composite (MGC), negative inspiratory force (NIF), forced vital capacity, MGFA post-intervention status, and other quality of life measurements. In certain embodiments, MG-ADL is the primary score for measuring improvement of MG.

Myasthenia Gravis Foundation of America (MGFA) Classification System

The Task Force of the Medical Scientific Advisory Board of the Myasthenia Gravis Foundation of America published a series of recommendations for clinical research standards in MG in 2000. Task Force of the Medical Scientific Advisory Board of the Myasthenia Gravis Foundation of America, Inc., Neurology 55: 16-23 (2000). This classification system was designed to identify subgroups of patients with MG who share distinct clinical features or severity of disease that may indicate different prognoses or responses to therapy.

The MGFA classification system based on clinical symptoms is as follows:

Class Clinical Symptoms
- I Any ocular muscle weakness. All other muscle strength is normal
- II Mild weakness affecting other than ocular muscles. May also have ocular muscle weakness of any severity
- IIa Predominantly affecting limb muscles, axial muscles, or both. May also have lesser involvement of oropharyngeal muscles, respiratory muscles, or both
- IIbb Predominantly affecting oropharyngeal muscles, respiratory muscles, or both. May also have lesser or equal involvement of limb muscles, axial muscles, or both
- III Moderate weakness affecting other than ocular muscles. May also have ocular muscle weakness of any severity
- IIIa Predominantly affecting limb muscles, axial muscles, or both. May also have lesser involvement of oropharyngeal muscles, respiratory muscles, or both
- IIIb Predominantly affecting oropharyngeal muscles, respiratory muscles, or both. May also have lesser or equal involvement of limb muscles, axial muscles, or both
- IV Severe weakness affecting other than ocular muscles. May also have ocular muscle weakness of any severity
- IVa Predominantly affecting limb muscles, axial muscles, or both. May also have lesser involvement of oropharyngeal muscles, respiratory muscles, or both
- IVb Predominantly affecting oropharyngeal muscles, respiratory muscles, or both. May also have lesser or equal involvement of limb muscles, axial muscles, or both
- V Defined by intubation, with or without mechanical ventilation, except when employed during routine postoperative management Myasthenia Gravis-Activities of Daily Living (MG-ADL)

The MG-ADL is an 8-item patient-reported scale to assess MG symptoms and their effects on daily activities. It evaluates the capacity to perform different activities of daily living such as talking, chewing, swallowing, breathing, brushing the teeth/combing the hair, or arising from the chair and it also assesses double vision and eyelid droop. It is a discrete quantitative variable in which the 8 items are rated from 0 to 3 and the total score can point from 0 to 24; with higher scores indicating more impairment. The 8 items of the MG-ADL were derived from symptom-based components of the original 13-item QMG to assess disability secondary to ocular (2 items), bulbar (3 items), respiratory (1 item), and gross motor or limb (2 items) impairment related to effects from MG. In this functional status instrument, each response is graded 0 (normal) to 3 (most severe). The range of total MG-ADL score is 0- 24, where higher scores indicate more severe impairments. In certain embodiments, a clinically meaningful improvement in a patient's MG-ADL is a 2 point or greater reduction in score (e.g., after 6 months of treatment). In certain embodiments, a clinically meaningful improvement in a patient's MG-ADL is a 3 point or greater reduction in score (e.g., after 6 months of treatment). Assessments performed using MG-ADL does not require any equipment or training, and the scoring scheme is shown in FIG. 3.

Quantitative Myasthenia Gravis (QMG)

The QMG quantifies disease severity based on impairments of body functions and structures as defined by the International Classification of Disability and Health. World Health Organization, International Classification of Functioning, Disability, and Health (ICF), 1st edition, World Health Organization (2001), available online at who.int/classifications/icf/en/. It consists of 13 items that assess ocular, bulbar, and limb function. Out of the 13 items, 6 are timed tests of endurance measured in seconds. Each item has a possible score from 0-3. The total possible score is 39, where higher scores indicate more severe impairments. It is based on quantitative testing of sentinel muscle groups to assess limb function. It requires minimal equipment such as spirometer, mouthpieces that fit the spirometer, nose clips, stopwatch, cups and water for swallowing tests, goniometer, dynamometer, and is based on physician's examination. FIG. 4 shows a typical QMG testing form. In certain embodiments, a clinically meaningful improvement in a patient's QMG score would be a 5 point or greater reduction in score (e.g., after 6 months of treatment).

Myasthenia Gravis Composite (MGC)

The MGC has 10 items combining physician examination and patient reported outcomes. The 2 ocular items are derived from QMG. It has 3 items on muscle strength (deltoids, hip flexors, and neck flexors or extensors) and 4 items on bulbar function (swallowing, chewing, breathing, and speech functions), based on the clinical history. Each item is scored on an ordinal scale with 4 possible categories, but the items are weighted, whereby bulbar impairments weigh more than ocular ones. The impairments measured by the examining physician include ptosis or upward gaze, double vision, eye closure, neck flexion, shoulder abduction, and hip flexion. The patient-reported outcomes under MGC are talking, chewing, swallowing, and breathing. The maximum possible score is 50, with higher scores reflecting more severe impairments. The items that are tested are shown in FIG. 5. In certain embodiments, a clinically meaningful improvement in a patient's MGC would be a 3 point or greater reduction in score (e.g., after 6 months of treatment).

15-Item Quality of Life Scale for Myasthenia Gravis (MGQoL15r)

The 15-item Quality of Life scale for Myasthenia Gravis [revised] (MGQoL15r) is a quality of life scale or survey of a patient's responses and addresses MG-specific psychological well-being and social functioning. It is a brief questionnaire that is to be completed by the patient that uses 3 response options. The MGQoL15r is helpful in informing the clinician about the patient's perception of the extent of and dissatisfaction with MG-related dysfunction. Each item is scored from 0 to 2 according to its frequency, with a maximum score of 30. The questions that patients should provide a response to assess their quality of life are shown in FIG. 6. In certain embodiments, a clinically meaningful improvement in a patient's MG-QOL 15 would be a decrease in score (e.g., after 6 months of treatment).

EuroQol 5 Dimension (EQ-5D)

The EQ-5D questionnaire is a very simple general health assessment instrument and is made up for two components; health state description and evaluation. In the description part, health status is measured in terms of five dimensions (5D): mobility, self-care, usual activities, pain/discomfort, and anxiety/depression. The mobility dimension asks about the person's walking ability. The self-care dimension asks about the ability to wash or dress by oneself, and the usual activities dimension measures performance in "work, study, housework, family or leisure activities." In the pain/discomfort dimension, the questionnaire asks how much pain or discomfort the person has, and in the anxiety/depression dimension, it asks how anxious or depressed the person is. Respondents self-rate their level of severity for each dimension using a three-level (EQ-5D-3L) or five-level (EQ-5D-5L) scale. As a result, using the original three-level instrument, a person's health status can be defined by a 5-digit number, ranging from 11111 (having no problems in all dimensions) to 33333 (having extreme problems in all dimensions). 12321 indicates having no problems in mobility and anxiety/depression, having slight problems in self-care and pain/discomfort, and having extreme problems in usual activities. There are potentially 243 ($=3^5$) different health states. In the evaluation part, respondents evaluate their overall health status using the visual analogue scale (EQ-VAS), indicating a position along a continuous line between two end-points. In certain embodiments, clinically meaningful improvement in a patient's EQ-5D would be reflected as an increase in score (e.g., after 1 month of treatment).

Current mainstays of MG treatment are AChE inhibitors, immunosuppressants and immunomodulating therapies. In the mild form of the disease, AChE inhibitors are used initially. These agents include pyridostigmine, neostigmine, and edrophonium and their effectiveness varies widely. Patients with generalized MG are treated with corticosteroids. Unfortunately, corticosteroids are typically characterized by delayed onset of effects. Because of their multiple side effects, the lowest effective dose of corticosteroids is recommended for long-term treatment that is often indicated for chronic conditions such as MG. Other non-steroidal immunosuppressive (NSIDs) agents are commonly used and include azathioprine (AZA), mycophenolate mofetil, cyclosporine, cyclophosphamide, and rituximab. However, the effectiveness of many of these medications varies widely among patients, take a long time to take effect and have numerous adverse consequences. Gilhus N E et al., Autoimmune Dis. 2011: 847393 (2011).

Plasma exchange (PE), immunoadsorption and IVIg are used for short-term treatment of MG exacerbations and when it is desirable to achieve a rapid clinical response. Plasma exchange temporarily reduces the concentrations of circulating anti-AChR antibodies and in most patients produces improvement in a matter of days. Typically, one exchange removing one to two plasma volumes is done every other day up to a total of four to six times, to improve muscle strength or ameliorate a myasthenic crisis. Unfortunately, this treatment is invasive and has common side-effects such as hypotension, paresthesia, infections, and thrombotic complications. IVIg is widely used for patients with exacerbating MG and data from randomized controlled studies show efficacy similar to PE. The mechanisms by which IVIg produce improvement are not clear, but two important possibilities are competition with autoantibodies (i.e., FcRn binding) and Fc receptor binding. It is important to note that a higher degree of auto-antibody reduction, faster onset and better clinical efficacy has been observed for PE and immunoadsorption when compared with IVIg. A fast onset is important for treatment of patients experiencing exacerbations. Liu J et al., Ther. Apher. Dial. 14(2): 153-160 (2009); Meriggioli M N et al., Lancet Neurol. 8(5): 475-490 (2009).

In certain embodiments, successful treatment of an exacerbation of myasthenia gravis or generalized myasthenia gravis results in at least a 1-point improvement in the MG-ADL score. In certain embodiments, successful treatment of an exacerbation of myasthenia gravis or generalized myasthenia gravis results in at least a 2-point improvement in the MG-ADL score. In certain embodiments, successful treatment of an exacerbation of myasthenia gravis or generalized myasthenia gravis results in at least a 3-point improvement in the MG-ADL score. In certain embodiments, successful treatment of an exacerbation of myasthenia gravis or generalized myasthenia gravis results in at least a 4-point improvement in the MG-ADL score. In certain embodiments, successful treatment of an exacerbation of myasthenia gravis or generalized myasthenia gravis results in at least a 5-point improvement in the MG-ADL score. In certain embodiments, successful treatment of an exacerbation of myasthenia gravis or generalized myasthenia gravis results in at least a 6-point improvement in the MG-ADL score. In certain embodiments, successful treatment of an exacerbation of myasthenia gravis or generalized myasthenia gravis results in at least a 7-point improvement in the MG-ADL score. In certain embodiments, successful treatment of an exacerbation of myasthenia gravis or generalized myasthenia gravis results in at least an 8-point improvement in the MG-ADL score. In certain embodiments, successful treatment of an exacerbation of myasthenia gravis or generalized myasthenia gravis results in at least a 9-point improvement in the MG-ADL score. In certain embodiments, successful treatment of an exacerbation of myasthenia gravis or generalized myasthenia gravis results in at least a 10-point improvement in the MG-ADL score.

In certain embodiments, successful treatment of an exacerbation of myasthenia gravis or generalized myasthenia gravis results in at least a 1-point improvement in the QMG score. In certain embodiments, successful treatment of an exacerbation of myasthenia gravis or generalized myasthenia gravis results in at least a 2-point improvement in the QMG score. In certain embodiments, successful treatment of an exacerbation of myasthenia gravis or generalized myasthenia gravis results in at least a 3-point improvement in the QMG score. In certain embodiments, successful treatment of an exacerbation of myasthenia gravis or generalized myasthenia gravis results in at least a 4-point improvement in the QMG score. In certain embodiments, successful treatment of an exacerbation of myasthenia gravis or generalized myasthenia gravis results in at least a 5-point improvement in the QMG score. In certain embodiments, successful treatment of an exacerbation of myasthenia gravis or generalized myasthenia gravis results in at least a 6-point improvement in the QMG score. In certain embodiments, successful treatment of an exacerbation of myasthenia gravis or generalized myasthenia gravis results in at least a 7-point improvement in the QMG score. In certain embodiments, successful treatment of an exacerbation of myasthenia gravis or generalized myasthenia gravis results in at least an 8-point improvement in the QMG score. In certain embodiments, successful treatment of an exacerbation of myasthenia gravis or generalized myasthenia gravis results in at least a 9-point improvement in the QMG score. In certain embodiments, successful treatment of an exacerbation of myasthenia gravis or generalized myasthenia gravis results in at least a 10-point improvement in the QMG score.

In certain embodiments, successful treatment of an exacerbation of myasthenia gravis or generalized myasthenia gravis results in at least a 1-point improvement in the MGC score. In certain embodiments, successful treatment of an exacerbation of myasthenia gravis or generalized myasthenia gravis results in at least a 2-point improvement in the MGC score. In certain embodiments, successful treatment of an exacerbation of myasthenia gravis or generalized myasthenia gravis results in at least a 3-point improvement in the MGC score. In certain embodiments, successful treatment of an exacerbation of myasthenia gravis or generalized myasthenia gravis results in at least a 4-point improvement in the MGC score. In certain embodiments, successful treatment of an exacerbation of myasthenia gravis or generalized myasthenia gravis results in at least a 5-point improvement in the MGC score. In certain embodiments, successful treatment of an exacerbation of myasthenia gravis or generalized myasthenia gravis results in at least a 6-point improvement in the MGC score. In certain embodiments, successful treatment of an exacerbation of myasthenia gravis or generalized myasthenia gravis results in at least a 7-point improvement in the MGC score. In certain embodiments, successful treatment of an exacerbation of myasthenia gravis or generalized myasthenia gravis results in at least an 8-point improvement in the MGC score. In certain embodiments, successful treatment of an exacerbation of myasthenia gravis or generalized myasthenia gravis results in at least a 9-point improvement in the MGC score. In certain embodiments, successful treatment of an exacerbation of myasthenia gravis or generalized myasthenia gravis results in at least a 10-point improvement in the MG-ADL score.

In certain embodiments, successful treatment of an exacerbation of myasthenia gravis or generalized myasthenia gravis results in at least a 1-point improvement in the MGQoL15r score. In certain embodiments, successful treatment of an exacerbation of myasthenia gravis or generalized myasthenia gravis results in at least a 2-point improvement in the MGQoL15r score. In certain embodiments, successful treatment of an exacerbation of myasthenia gravis or generalized myasthenia gravis results in at least a 3-point improvement in the MGQoL15r score. In certain embodiments, successful treatment of an exacerbation of myasthenia gravis or generalized myasthenia gravis results in at least a 4-point improvement in the MGQoL15r score. In certain embodiments, successful treatment of an exacerbation of myasthenia gravis or generalized myasthenia gravis results in at least a 5-point improvement in the MGQoL15r score. In certain embodiments, successful treatment of an exacerbation of myasthenia gravis or generalized myasthenia gravis results in at least a 6-point improvement in the MGQoL15r score.

In certain embodiments, successful treatment of an exacerbation of myasthenia gravis or generalized myasthenia gravis results in at least a 7-point improvement in the MGQoL15r score. In certain embodiments, successful treatment of an exacerbation of myasthenia gravis or generalized myasthenia gravis results in at least an 8-point improvement in the MGQoL15r score. In certain embodiments, successful treatment of an exacerbation of myasthenia gravis or generalized myasthenia gravis results in at least a 9-point improvement in the MGQoL15r score. In certain embodiments, successful treatment of an exacerbation of myasthenia gravis or generalized myasthenia gravis results in at least a 10-point improvement in the MGQoL15r score.

In certain embodiments, administration of the isolated FcRn antagonist improves one or more myasthenia gravis therapeutic evaluation scores in the subject selected from the group consisting of Quantitative Myasthenia Gravis (QMG) score, Myasthenia Gravis activities of daily living (MG-ADL) score, Myasthenia Gravis composite (MGC) score, 15-item Quality of life scale for Myasthenia Gravis (MGQoL15r), and EuroQol 5 Dimension (EQ-5D) score.

In certain embodiments, the QMG score is improved at day 8, 15, 22, 29, or 36 compared to a baseline QMG score as measured prior to administration of the isolated FcRn antagonist at day 1. In certain embodiments, the QMG score is decreased by at least 3 points at day 8, 15, 22, 29, or 36 compared to a baseline QMG score as measured prior to administration of the isolated FcRn antagonist at day 1. In certain embodiments, the QMG score is decreased by at least 4 points at day 8, 15, 22, 29, or 36 compared to a baseline QMG score as measured prior to administration of the isolated FcRn antagonist at day 1.

In certain embodiments, the MG-ADL score is improved at day 8, 15, 22, 29, or 36 compared to a baseline MG-ADL score as measured prior to administration of the isolated FcRn antagonist at day 1. In certain embodiments, the MG-ADL score is decreased by at least 2 points at day 8, 15, 22, 29, or 36 compared to a baseline MG-ADL score as measured prior to administration of the isolated FcRn antagonist at day 1. In certain embodiments, the MG-ADL score is decreased by at least 3 points at day 8, 15, 22, 29, or 36 compared to a baseline MG-ADL score as measured prior to administration of the isolated FcRn antagonist at day 1.

In certain embodiments, the MGC score is improved at day 8, 15, 22, 29, or 36 compared to a baseline MGC score as measured prior to administration of the isolated FcRn antagonist at day 1. In certain embodiments, the MGC score is decreased by at least 4 points at day 8, 15, 22, 29, or 36 compared to a baseline MGC score as measured prior to administration of the isolated FcRn antagonist at day 1. In certain embodiments, the MGC score is decreased by at least 5 points at day 8, 15, 22, 29, or 36 compared to a baseline MGC score as measured prior to administration of the isolated FcRn antagonist at day 1.

In certain embodiments, the MGQoL15r score is improved at day 8, 15, 22, 29, or 36 compared to a baseline MGQoL 15r score as measured prior to administration of the isolated FcRn antagonist at day 1. In certain embodiments, the MGQoL 15r score is decreased by at least 3 points at day 8, 15, 22, 29, or 36 compared to a baseline MGQoL 15r score as measured prior to administration of the isolated FcRn antagonist at day 1. In certain embodiments, the MGQoL15r score is decreased by at least 4 points at day 8, 15, 22, 29, or 36 compared to a baseline MGQoL 15r score as measured prior to administration of the isolated FcRn antagonist at day 1.

In certain embodiments, administration of the isolated FcRn antagonist improves one or more clinical symptoms of the generalized myasthenia gravis selected from the group consisting of ocular muscle fatigue or weakness, skeletal muscle fatigue or weakness, respiratory muscle fatigue or weakness, disabling fatigue, slurred speech, choking, impaired swallowing, double or blurred vision, immobility requiring assistance, shortness of breath, and respiratory failure.

III. FcRn Antagonists

The methods disclosed herein generally comprise administering to a subject an effective amount of an isolated FcRn antagonist. The FcRn antagonist inhibits the binding of Fc-containing agents (e.g., antibodies and immunoadhesins) to FcRn in vivo, which results in an increased rate of degradation of the Fc-containing agents and, concomitantly, a reduced serum level of these agents.

In certain embodiments, the FcRn antagonist binds specifically to FcRn with increased affinity and reduced pH dependence relative to native Fc region (e.g., FcRn antagonists disclosed herein). In general, these FcRn antagonists comprise a variant Fc region, or FcRn-binding fragment thereof, that binds specifically to FcRn with increased affinity and reduced pH dependence relative to a native Fc region. In certain embodiments, the FcRn antagonist binds specifically to FcRn with increased affinity and reduced pH dependence relative to a wild-type IgG Fc region, for example a wild-type IgG1 Fc region. In certain embodiments, the FcRn antagonist binds specifically to FcRn with increased affinity and reduced pH dependence relative to a wild-type human IgG Fc region, for example a wild-type human IgG1 Fc region.

i. Variant Fc Regions with FcRn Binding Activity

In certain embodiments, the isolated FcRn antagonist is an antibody or Fc fragment comprising or consisting of a variant Fc region, or FcRn-binding fragment thereof.

In certain embodiments, the Fc domains of the variant Fc region, or FcRn-binding fragment thereof, comprise the amino acids Y, T, E, K, F, and Y at EU positions 252, 254, 256, 433, 434, and 436, respectively.

In certain embodiments, the variant Fc region is a variant IgG Fc region. In certain embodiments, the variant Fc region is a variant IgG1 Fc region.

In certain embodiments, the variant Fc region is a variant human IgG Fc region. In certain embodiments, the variant Fc region is a variant human IgG1 Fc region.

In certain embodiments, an isolated variant Fc region (e.g., a variant Fc region comprising the amino acids Y, T, E, K, F, and Y at EU positions 252, 254, 256, 433, 434, and 436 respectively) is a more efficacious FcRn antagonist in vivo than a full-length antibody comprising the same variant Fc region. Accordingly, in certain embodiments, the FcRn antagonist compositions are not full-length antibodies. In certain embodiments, the FcRn antagonist compositions do not comprise an antibody variable domain. In certain embodiments, the FcRn antagonist compositions do not comprise an antibody variable domain or a CH1 domain. However, in certain embodiments, the FcRn antagonist compositions may comprise a variant Fc region linked to one or more additional binding domains or moieties, including antibody variable domains.

Any Fc region can be altered to produce a variant Fc region for use in the FcRn antagonist compositions disclosed herein. In general, an Fc region, or FcRn-binding fragment thereof, is from a human immunoglobulin. It is understood, however, that the Fc region may be derived from an immunoglobulin of any other mammalian species, including for example, a Camelid species, a rodent (e.g. a mouse, rat, rabbit, guinea pig) or non-human primate (e.g. chimpanzee, macaque) species. Moreover, the Fc region or portion thereof may be derived from any immunoglobulin class, including IgM, IgG, IgD, IgA and IgE, and any immunoglobulin isotype, including IgG1, IgG2, IgG3 and IgG4. In certain embodiments, the Fc region is an IgG Fc region (e.g., a human IgG region). In certain embodiments, the Fc region is an IgG1 Fc region (e.g., a human IgG1 region). In certain embodiments, the Fc region is a chimeric Fc region comprising portions of several different Fc regions. Suitable examples of chimeric Fc regions are set forth in US Pat. Appl. Pub. 2011/0243966A1, which is incorporated herein by reference in its entirety. A variety of Fc region gene sequences (e.g. human constant region gene sequences) are available in the form of publicly accessible deposits. It will be appreciated that the scope of this invention encompasses alleles, variants and mutations of Fc regions.

An Fc region can be further truncated or internally deleted to produce a minimal FcRn-binding fragment thereof. The ability of an Fc-region fragment to bind to FcRn can be determined using any art recognized binding assay e.g., ELISA.

To enhance the manufacturability of the FcRn antagonists disclosed herein, it is preferable that the constituent Fc regions do not do comprise any non-disulphide bonded cysteine residues. Accordingly, in certain embodiments the Fc regions do not comprise a free cysteine residue.

Any Fc variant, or FcRn-binding fragment thereof, that binds specifically to FcRn with increased affinity and reduced pH dependence relative to the native Fc region can be used in the FcRn antagonist compositions disclosed herein. In certain embodiments, the variant Fc region comprises amino acid alterations, substitutions, insertions and/or deletions that confer the desired characteristics. In certain embodiments, the variant Fc region or fragment comprises the amino acids Y, T, E, K, F, and Y at EU positions 252, 254, 256, 433, 434, and 436 respectively. Non-limiting examples of amino acid sequences that can be used in variant Fc regions are set forth in Table 2, herein. In certain embodiments, the amino acid sequence of the Fc domains of the variant Fc region comprises an amino acid sequence selected from the group consisting of SEQ ID NOs: 1, 2, and 3. In certain embodiments, the amino acid sequence of the Fc domains of the variant Fc region consists of an amino acid sequence selected from the group consisting of SEQ ID NOs: 1, 2, and 3.

SEQ ID NO: 2 represents the amino acid sequence of the Fc domains of the FcRn antagonist ARGX-113. See US Pat. Appl. Pub. 2015/0218239 and WO 2015/100299 which are incorporated herein by reference. SEQ ID NOs: 1 and 3 represent certain variants of the amino acid sequence of the Fc domains of the FcRn antagonist ARGX-113.

In certain embodiments, the amino acid sequence of the Fc domains of the variant Fc region comprises the amino acid sequence of SEQ ID NO: 1. In certain embodiments, the amino acid sequence of the Fc domains of the variant Fc region consists of the amino acid sequence of SEQ ID NO: 1.

In certain embodiments, the amino acid sequence of the Fc domains of the variant Fc region comprises the amino acid sequence of SEQ ID NO: 2. In certain embodiments, the amino acid sequence of the Fc domains of the variant Fc region consists of the amino acid sequence of SEQ ID NO: 2.

In certain embodiments, the amino acid sequence of the Fc domains of the variant Fc region comprises the amino acid sequence of SEQ ID NO: 3. In certain embodiments, the amino acid sequence of the Fc domains of the variant Fc region consists of the amino acid sequence of SEQ ID NO: 3.

In certain embodiments, the isolated FcRn antagonist consists of a variant Fc region, wherein said variant Fc region consists of two Fc domains which form a homodimer, wherein the amino acid sequence of each of the Fc domains consists of SEQ ID NO: 1.

In certain embodiments, the isolated FcRn antagonist consists of a variant Fc region, wherein said variant Fc region consists of two Fc domains which form a homodimer, wherein the amino acid sequence of each of the Fc domains consists of SEQ ID NO: 2.

In certain embodiments, the isolated FcRn antagonist consists of a variant Fc region, wherein said variant Fc region consists of two Fc domains which form a homodimer, wherein the amino acid sequence of each of the Fc domains consists of SEQ ID NO: 3.

TABLE 2

Amino acid sequences of non-limiting examples of variant Fc regions

| SEQ ID NO: | Amino Acid Sequence |
|---|---|
| 1 | CPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALKFHYTQKSLSLSPG |
| 2 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALKFHYTQKSLSLSPGK |
| 3 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALKFHYTQKSLSLSPG |

Amino acids at EU positions 252, 254, 256, 433, and 434 are shown in bold ii. Anti-FcRN Antibodies In certain embodiments, the FcRn antagonist is a monoclonal or engineered antibody specific for the FcRn. In certain embodiments, the FcRn antagonist is a monoclonal or engineered antibody specific for human FcRn. In certain embodiments, the FcRn antagonist is an antigen-binding fragment of a monoclonal or engineered antibody specific for the FcRn. In certain embodiments, the FcRn antagonist is an antigen-binding fragment of a monoclonal or engineered antibody specific for human FcRn.

In certain embodiments, the FcRn antagonist comprises a heavy chain (HC) immunoglobulin variable domain sequence and a light chain (LC) immunoglobulin variable domain sequence, wherein the HC comprises: a HC CDR1 comprising or consisting of an amino acid sequence selected from the group consisting of EYAMG (SEQ ID NO: 4) and VYAMG (SEQ ID NO: 5), a HC CDR2 comprising or consisting of an amino acid sequence selected from the group consisting of SIGSSGGQTKYADSVKG (SEQ ID NO: 6) and SIGSSGGPTKYADSVKG (SEQ ID NO: 7), and a HC CDR3 comprising or consisting of an amino acid sequence selected from the group consisting of LSTGELY (SEQ ID NO: 8), LSIRELV (SEQ ID NO: 9), LSIVDSY (SEQ ID NO: 10), LSLGDSY (SEQ ID NO: 11), and LAIGDSY (SEQ ID NO: 12); and the LC comprises: a LC CDR1 comprising or consisting of the amino acid sequence TGTGSDVGSYNLVS (SEQ ID NO: 13), a LC CDR2 comprising or consisting of the amino acid sequence GDSQRPS (SEQ ID NO: 14), and a LC CDR3 comprising or consisting of the amino acid sequence CSYAGSGIYV (SEQ ID NO: 15).

In certain embodiments, the FcRn antagonist comprises (1) a light chain variable region comprising a CDR L1, a CDR L2, and a CDR L3 and (2) a heavy chain variable region comprising a CDR H1, a CDR H2, and a CDR H3, wherein said CDR L1 has an amino acid sequence having no more than two amino acid substitutions relative to the sequence of TGTGSDVGSYNLVS (SEQ ID NO: 13), said CDR L2 has an amino acid sequence having no more than one amino acid substitution relative to the sequence of GDSERPS (SEQ ID NO: 16), said CDR L3 has an amino acid sequence having no more than one amino acid substitution relative to the sequence of SSYAGSGIYV (SEQ ID NO: 17), said CDR H1 has an amino acid sequence having no more than one amino acid substitution relative to a sequence selected from the group consisting of TYAMG (SEQ ID NO: 18), DYAMG (SEQ ID NO: 19), and NYAMG (SEQ ID NO: 20), said CDR H2 has an amino acid sequence having no more than two amino acid substitutions relative to a sequence selected from the group consisting of SIGSSGAQTRYADS (SEQ ID NO: 21), SIGASGSQTRYADS (SEQ ID NO: 22), SIGASGAQTRYADS (SEQ ID NO: 23), and SIGASGGQTRYADS (SEQ ID NO: 24), and said CDR H3 has an amino acid sequence having no more than one amino acid substitution relative to the sequence of LAIGDSY (SEQ ID NO:25).

In certain embodiments, the FcRn antagonist comprises a heavy chain (HC) immunoglobulin variable domain sequence and a light chain (LC) immunoglobulin variable domain sequence, wherein: the HC comprises: a HC CDR1 comprising or consisting of the amino acid sequence GFTFSNYGMV (SEQ ID NO: 26), a HC CDR2 comprising or consisting of the amino acid sequence YIDSDGDNTYYRDSVKG (SEQ ID NO: 27), and a HC CDR3 comprising or consisting of the amino acid sequence GIVRPFLY (SEQ ID NO: 28); and the LC comprises: a LC CDR1 comprising or consisting of the amino acid sequence KSSQSLVGASGKTYLY (SEQ ID NO: 29), a LC CDR2 comprising or consisting of the amino acid sequence LVSTLDS (SEQ ID NO: 30), and a LC CDR3 comprising or consisting of the amino acid sequence LQGTHFPHT (SEQ ID NO: 31).

In certain embodiments, the FcRn antagonist comprises a heavy chain (HC) immunoglobulin variable domain sequence and a light chain (LC) immunoglobulin variable domain sequence, wherein: the HC comprises: a HC CDR1 comprising or consisting of the amino acid sequence SYGIS (SEQ ID NO: 32), a HC CDR2 comprising or consisting of the amino acid sequence EIYPRSGNTYYNEKFKG (SEQ ID NO: 33), a HC CDR3 comprising or consisting of an amino acid sequence selected from the group consisting of SEQ ID NOs: 34-50; and the LC comprises: a LC CDR1 comprising or consisting of the amino acid sequence KAS-DHINNWLA (SEQ ID NO: 51), a LC CDR2 comprising or consisting of the amino acid sequence GATSLET (SEQ ID NO: 52), and a LC CDR3 comprising or consisting of an amino acid sequence selected from the group consisting of SEQ ID NOs: 53-57.

TABLE 3

FcRn antagonist CDR amino acid sequences

| SEQ ID NO: | Amino Acid Sequence | CDR |
|---|---|---|
| 4 | EYAMG | HC CDR1 |
| 5 | VYAMG | HC CDR1 |
| 6 | SIGSSGGQTKYADSVKG | HC CDR2 |
| 7 | SIGSSGGPTKYADSVKG | HC CDR2 |
| 8 | LSTGELY | HC CDR3 |
| 9 | LSIRELV | HC CDR3 |
| 10 | LSIVDSY | HC CDR3 |
| 11 | LSLGDSY | HC CDR3 |
| 12 | LAIGDSY | HC CDR3 |
| 13 | TGTGSDVGSYNLVS | LC CDR1 |
| 14 | GDSQRPS | LC CDR2 |
| 15 | CSYAGSGIYV | LC CDR3 |
| 16 | GDSERPS | LC CDR2 |
| 17 | SSYAGSGIYV | LC CDR3 |
| 18 | TYAMG | HC CDR1 |
| 19 | DYAMG | HC CDR1 |
| 20 | NYAMG | HC CDR1 |
| 21 | SIGSSGAQTRYADS | HC CDR2 |
| 22 | SIGASGSQTRYADS | HC CDR2 |
| 23 | SIGASGAQTRYADS | HC CDR2 |
| 24 | SIGASGGQTRYADS | HC CDR2 |
| 25 | LAIGDSY | HC CDR3 |
| 26 | GFTFSNYGMV | HC CDR1 |
| 27 | YIDSDGDNTYYRDSVKG | HC CDR2 |
| 28 | GIVRPFLY | HC CDR3 |
| 29 | KSSQSLVGASGKTYLY | LC CDR1 |
| 30 | LVSTLDS | LC CDR2 |
| 31 | LQGTHFPHT | LC CDR3 |
| 32 | SYGIS | HC CDR1 |
| 33 | EIYPRSGNTYYNEKFKG | HC CDR2 |
| 34 | STTVSPADF | HC CDR3 |
| 35 | STTVSPPPI | HC CDR3 |
| 36 | STTVSPPAH | HC CDR3 |
| 37 | STTVAPPRL | HC CDR3 |
| 38 | STTVHPDRN | HC CDR3 |
| 39 | STTVSPPAL | HC CDR3 |
| 40 | STTVHPDHN | HC CDR3 |
| 41 | STTVSPPHL | HC CDR3 |
| 42 | STTVAPPPL | HC CDR3 |
| 43 | STTVAPPGH | HC CDR3 |
| 44 | STTVSPPRV | HC CDR3 |
| 45 | STTVSPPPL | HC CDR3 |
| 46 | STTVAPPAH | HC CDR3 |
| 47 | STTVRPPGI | HC CDR3 |
| 48 | STTVSAPGV | HC CDR3 |
| 49 | STTVXPPXX | HC CDR3 |
| 50 | STTVXXXXX | HC CDR3 |
| 51 | KASDHINNWLA | LC CDR1 |
| 52 | GATSLET | LC CDR2 |
| 53 | QQYWSTPYT | LC CDR3 |
| 54 | NTYGNNPHT | LC CDR3 |
| 55 | HQYYNTPYT | LC CDR3 |
| 56 | QYYSTPYT | LC CDR3 |
| 57 | QQYYSTPYT | LC CDR3 | iii. Other Fc Modifications

In certain embodiments, FcRn antagonists of the invention may comprise additional Fc modification. For example, the FcRn antagonist may comprise a variant Fc region that has altered (e.g., increased or decreased) binding affinity for an additional Fc receptor. The variant Fc region can have altered (e.g., increased or decreased) binding affinity for one or more of Fcγ receptors e.g., FcγRI (CD64), FcγRIIA (CD32), FcγRIIB (CD32), FcγRIIIA (CD16a), and FcγRIIIB (CD16b). Any art recognized means of altering the affinity for an additional Fc receptor can be employed. In certain embodiments, the amino acid sequence of the variant Fc region is altered.

In certain embodiments, the variant Fc region comprises a non-naturally occurring amino acid residue at one or more positions selected from the group consisting of 234, 235, 236, 239, 240, 241, 243, 244, 245, 247, 252, 254, 256, 262, 263, 264, 265, 266, 267, 269, 296, 297, 298, 299, 313, 325, 326, 327, 328, 329, 330, 332, 333, and 334 as numbered by the EU index as set forth in Kabat. Optionally, the Fc region may comprise a non-naturally occurring amino acid residue at additional and/or alternative positions known to one skilled in the art (see, e.g., U.S. Pat. Nos. 5,624,821;

6,277,375; and 6,737,056; and PCT Patent Publications WO 01/58957; WO 02/06919; WO 04/016750; WO 04/029207; WO 04/035752 and WO 05/040217, the contents of which are incorporated by reference herein in their entirety).

In certain embodiments, the variant Fc region comprises at least one non-naturally occurring amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241L, 241Y, 241E, 241R. 243W, 243L 243Y, 243R, 243Q, 244H, 245A, 247V, 247G, 252Y, 254T, 256E, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 269H, 269Y, 269F, 269R, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 313F, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 332D, 332S, 332W, 332F, 332E, 332N, 332Q, 332T, 332H, 332Y, and 332A as numbered by the EU index as set forth in Kabat. Optionally, the Fc region may comprise additional and/or alternative non-naturally occurring amino acid residues known to one skilled in the art (see, e.g., U.S. Pat. Nos. 5,624,821; 6,277,375; and 6,737,056; and PCT Patent Publications WO 01/58957; WO 02/06919; WO 04/016750; WO 04/029207; WO 04/035752 and WO 05/040217, the contents of which are incorporated by reference herein in their entirety).

Other known Fc variants that may be used in the FcRn antagonists disclosed herein include without limitations those disclosed in Ghetie et al., 1997, Nat. Biotech. 15: 637-40; Duncan et al., 1988, Nature 332: 563-564; Lund et al., 1991, J. Immunol. 147: 2657-2662; Lund et al., 1992, Mol. Immunol. 29: 53-59; Alegre et al., 1994, Transplantation 57: 1537-1543; Hutchins et al., 1995, Proc. Natl. Acad. Sci. USA 92: 11980-11984; Jefferis et al., 1995, Immunol. Lett. 44: 111-117; Lund et al., 1995, FASEB J. 9: 115-119; Jefferis et al., 1996, Immunol. Lett. 54: 101-104; Lund et al., 1996, J. Immunol. 157: 4963-4969; Armour et al., 1999, Eur. J. Immunol. 29: 2613-2624; Idusogie et al., 2000, J. Immunol. 164: 4178-4184; Reddy et al., 2000, J. Immunol. 164: 1925-1933; Xu et al., 2000, Cell. Immunol. 2000: 16-26; Idusogie et al., 2001, J. Immunol. 166: 2571-2575; Shields et al., 2001, J Biol. Chem. 276: 6591-6604; Jefferis et al., 2002, Immunol. Lett. 82: 57-65; Presta et al., 2002, Biochem. Soc. Trans. 30: 487-490); U.S. Pat. Nos. 5,624, 821; 5,885,573; 5,677,425; 6,165,745; 6,277,375; 5,869, 046; 6,121,022; 5,624,821; 5,648,260; 6,528,624; 6,194, 551; 6,737,056; 6,821,505; 6,277,375; U.S. Patent Publication No. 2004/0002587; and PCT Publications WO 94/29351; WO 99/58572; WO 00/42072; WO 02/060919; WO 04/029207; WO 04/099249; and WO 04/063351, the contents of which are incorporated by reference herein in their entirety.

In certain embodiments, the variant Fc region is a heterodimer, where the constituent Fc domains are different from each other. Methods of producing Fc heterodimers are known in the art (see e.g., U.S. Pat. No. 8,216,805, which is incorporated by reference herein in its entirety). In certain embodiments, the variant Fc region is a single chain Fc region, where the constituent Fc domains are linked together by a linker moiety. Methods of producing single chain Fc regions are known in the art (see e.g., US20090252729A1 and US20110081345A1, which are each incorporated by reference herein in their entirety).

In certain embodiments, the FcRn antagonist comprises a variant Fc-region comprising an N-linked glycan (e.g., at EU position 297). In this case it is possible to increase the binding affinity of the FcRn antagonist for CD16a by altering the glycan structure. Alterations of the N-linked glycan of Fc regions are well known in the art. For example, afucosylated N-linked glycans or N-glycans having a bisecting GlcNAc structure have been shown to exhibit increased affinity for CD16a. Accordingly, in certain embodiments, the N-linked glycan is afucosylated. Afucosylation can be achieved using any art-recognized means. For example, an FcRn antagonist can be expressed in cells lacking fucosyl transferase, such that fucose is not added to the N-linked glycan at EU position 297 of the variant Fc region (see e.g., U.S. Pat. No. 8,067,232, the contents of which is incorporated by reference herein in its entirety). In certain embodiments, the N-linked glycan has a bisecting GlcNAc structure. The bisecting GlcNAc structure can be achieved using any art recognized means. For example, an FcRn antagonist can be expressed in cells expressing beta1-4-N-acetylglucosaminyltransferase III (GnTIII), such that bisecting GlcNAc is added to the N-linked glycan at EU position 297 of the variant Fc region (see e.g., U.S. Pat. No. 8,021,856, the contents of which is incorporated by reference herein in its entirety). Additionally or alternatively, alterations of the N-linked glycan structure can also be achieved by enzymatic means in vitro.

In certain embodiments, the FcRn antagonist comprises a plurality of FcRn antagonist molecules, wherein at least 50% (optionally, at least 60, 70, 80, 90, 95, or 99%) of the plurality of FcRn antagonist molecules comprise a variant Fc region, or FcRn-binding fragment thereof, comprising a fucosylated N-linked glycan at EU position 297.

In certain embodiments, the FcRn antagonist comprises a plurality of FcRn antagonist molecules, wherein at least 50% (optionally, at least 60, 70, 80, 90, 95, or 99%) of the plurality of FcRn antagonist molecules comprise a variant Fc region or FcRn-binding fragment thereof, comprising an N-linked glycan having a bisecting GlcNAc at EU position 297.

In certain embodiments, the variant Fc region does not comprise an N-linked glycan. This can be achieved using any art recognized methods. For example, the Fc variant can be expressed in a cell that is incapable of N-linked glycosylation. Additionally or alternatively, the amino acid sequence of the Fc variant can be altered to prevent or inhibit N-linked glycosylation (e.g., by mutation of the NXT sequon). Alternatively, the Fc variant can be synthesized in an acellular system (e.g., chemically synthesized).

In certain embodiments, FcRn antagonist molecules may be modified, e.g., by the covalent attachment of a molecule (e.g., a binding or imaging moiety) to the FcRn antagonist such that covalent attachment does not prevent the FcRn antagonist from specifically binding to FcRn. For example, but not by way of limitation, the FcRn antagonist may be modified by glycosylation, acetylation, pegylation, phosphorylation, amidation, derivatization by known protecting blocking groups, proteolytic cleavage, linkage to a cellular ligand or other protein, etc.

In certain embodiments, the FcRn antagonist comprises a variant Fc region linked to a half-life extender. As used herein, the term "half-life extender" refers to any molecule that, when linked to an FcRn antagonist disclosed herein, increases the half-life of an FcRn antagonist. Any half-life extender may be linked (either covalently or non-covalently) to the FcRn antagonist. In certain embodiments, the half-life extender is polyethylene glycol or human serum albumin. In certain embodiments, the FcRn antagonist is linked to a binding molecule that specifically binds to a half-life extender present in a subject, such as a blood-carried molecule or cell, such as serum albumin (e.g., human serum albumin), IgG, erythrocytes, etc.

IV. Methods of Treating Generalized Myasthenia Gravis

In one aspect, the instant disclosure provides methods of treating generalized myasthenia gravis in a subject. These methods generally comprise administering to the subject an effective amount of an isolated FcRn antagonist. The instant disclosure also provides an isolated FcRn antagonist for use in treating generalized myasthenia gravis in a subject. The instant disclosure further provides use of an isolated FcRn antagonist in the manufacture of a medicament for use in treating generalized myasthenia gravis in a subject.

Dosing and Route of Administration

As shown herein, a multiple, repeated dosing regime is unexpectedly superior to a single dose. Accordingly, in certain embodiments, the FcRn antagonist is administered to the subject at least twice in 22 days. In certain embodiments, the FcRn antagonist is administered to the subject at a frequency of once every 1, 2, 3, 4, 5, 6, 7, 8, 9, 10, or 11 days. In certain embodiments, the FcRn antagonist is administered to the subject 1, 2, 3, 4, 5, 6, 7, 8, 9, 10, 11, 12, 13, 14, 15, 16, 17, 18, 19, 20, 21, or 22 times in 22 days. In certain embodiments, the FcRn antagonist is administered to the subject at a frequency of once every 3 days. In certain embodiments, the FcRn antagonist is administered to the subject at a frequency of once every 7 days. In certain embodiments, the FcRn antagonist is administered to the subject every 7 days for 22 days (i.e., on days 1, 8, 15, and 22).

As shown herein, administration of an FcRn antagonist to the subject in a dose of between about 1 and about 200 mg/kg is unexpectedly efficacious. Accordingly, in certain embodiments, the FcRn antagonist is administered to the subject in a dose of between about 1 and about 200 mg/kg (e.g., between 1 and 200 mg/kg). In certain embodiments, the FcRn antagonist is administered to the subject in a dose of about 1, 2, 10, 20, 25, 70, or 200 mg/kg (e.g., 1, 2, 10, 20, 25, 70, or 200 mg/kg). In certain embodiments, the FcRn antagonist is administered to the subject in a dose of about 5 mg/kg (e.g., 5 mg/kg). In certain embodiments, the FcRn antagonist is administered to the subject in a dose of about 10 mg/kg (e.g., 10 mg/kg). In certain embodiments, the FcRn antagonist is administered to the subject in a dose of about 20 mg/kg (e.g., 20 mg/kg). In certain embodiments, the FcRn antagonist is administered to the subject in a dose of about 25 mg/kg (e.g., 25 mg/kg).

In certain embodiments, the FcRn antagonist is administered to the subject in a dose selected from the group consisting of about 150, 300, 450, 600, 750, 900, 1050, and 1200 mg per dose.

In certain embodiments, the FcRn antagonist is administered to the subject in a dose of about 150 mg per dose.

In certain embodiments, the FcRn antagonist is administered to the subject in a dose of about 300 mg per dose.

In certain embodiments, the FcRn antagonist is administered to the subject in a dose of about 450 mg per dose.

In certain embodiments, 10 mg/kg of the FcRn antagonist is administered to the subject every 7 days for 22 days (i.e., on days 1, 8, 15, and 22).

As myasthenia gravis is a chronic disease, in certain embodiments at least one additional dose of the FcRn antagonist is administered to the subject. For example, one or more additional doses of the FcRn antagonist can be administered to the subject weekly, biweekly, every three weeks, every four weeks, every 6 weeks, every 8 weeks, every 12 weeks, or on a schedule intermediate to any of the foregoing. Dose scheduling can be adjusted based on clinical symptoms.

As myasthenia gravis is a chronic disease, in certain embodiments at least one additional dose of the FcRn antagonist is administered to the subject. For example, one or more additional doses of the FcRn antagonist can be administered to the subject on an as-needed basis depending on clinical symptoms. In this manner, the clinician or subject can tailor dosing to the individual subject's requirements.

The FcRn antagonist can be administered by any means to the subject. Methods of administration include, but are not limited to, intravenous, subcutaneous, intradermal, intramuscular, intraperitoneal, intranasal, epidural, and oral routes. The composition may be administered, for example by infusion or bolus injection. In certain embodiments, the FcRn antagonist is administered by intravenous infusion. In certain embodiments, the FcRn antagonist is administered by subcutaneous injection. In certain embodiments, the first dose is administered to the subject intravenously, and one or more subsequent doses are administered subcutaneously.

In various embodiments, the FcRn antagonist is administered in a multiphase dosing regimen. For example, the multiphase dosing regimen comprises a first phase and a second phase in various embodiments. In certain embodiments, the first phase is an induction phase and comprises administering 1-5 doses of FcRn antagonist to the subject for between 1-10 weeks, e.g., 1 month. In certain embodiments, the induction phase doses are administered at about 5 mg/kg, about 10 mg/kg, about 15 mg/kg or about 20 mg/kg. In certain embodiments, the induction phase doses are administered intravenously. The induction phase is concluded by administering the first maintenance phase dose of FcRn antagonist.

In certain embodiments, the induction phase lasts for 2, 3, 4, 5, 6, 7, 8, 9, or 10 weeks. In certain embodiments, this phase lasts between 2 and 6 weeks. In certain embodiments, the induction phase lasts for 5 weeks. According to certain embodiments, the dose given any week is higher than the previous week. In other embodiments, the dose remains the same for a number of weeks and is then increased. In some embodiments, the dose remains the same for the first 1, 2, 3, 4, 5, 6, 7, 8, or 9 weeks and is then increased. In certain embodiments, the dose remains the same for the first 4 weeks.

In certain embodiments, the second phase is a maintenance phase and comprises administering between 50 mg and 500 mg (e.g., 150 mg or 300 mg) once every one or two weeks to the subject for 2 weeks, 4 weeks, 6 weeks, 8 weeks, 12 weeks, 26 weeks, or as long as myasthenia gravis persists. In other embodiments, the maintenance phase comprises administration of an FcRn antagonist at between 50 mg and 500 mg (e.g., 150 mg or 300 mg) once every two weeks to the subject for 2 months, 4 months, 6 months, 8 months, 12 months, 2 years, three years, 4 years, 5 years, or for the remaining lifetime of the subject. In other embodiments, the maintenance phase comprises subcutaneous (s.c.) administration of FcRn antagonist at about 50-500 mg (e.g., 150 mg or 300 mg) twice a month (biweekly) once the induction phase is complete. In some embodiments, the maintenance phase comprises administering an FcRn antagonist to the subject on an as-needed basis depending on clinical symptoms. In this manner, the clinician or subject can tailor dosing to the individual subject's requirements.

In certain embodiments, the maintenance phase can last for between 6 weeks and the life of the subject. According to other embodiments, the maintenance phase lasts for 26-52, 26-78, 26-104, 26-130, 26-156, 26-182, 26-208 weeks, or more. In other embodiments, the maintenance phase lasts for greater than 26, 27, 28, 29, 30, 31, 32, 33, 34, 35, 36, 37, 38, 39, 40, 41, 42, 43, 44, 45, 46, 47, 48, 49, 50, 51, 52, 78, 104, 130, 156, or 182 weeks. According to other embodiments, the maintenance phase lasts for greater than 1, 2, 3, 4, 5, 10, 15, 20, 25, 30, 35, 40, 45, 50, 55, 60, 65, 70, 75, 80 years, or more years. In certain embodiments, the maintenance phase lasts for the remainder of the subject's life.

In certain embodiments, the multiphase dosing regimen includes a "tapering" phase in which the dose of FcRn antagonist is decreased with each succeeding dose. The tapering phase may occur after the subject has exhibited an improvement in one or more symptoms of MG. In certain embodiments, this tapering phase may include a replacement therapy other than an FcRn antagonist (e.g., a steroid therapy, IVIg or plasma exchange).

In certain embodiments, the multiphase dosing regimen includes a "retreatment" phase. The retreatment phase may occur after the subject has ceased treatment with an FcRn antagonist for an extended period of time (e.g., 3 months, 6 months, 1 year or more) or after the subject has begun (but not fully completed) the tapering phase. In certain embodiments, this retreatment phase is used when an MG patient must undergo a rescue procedure to maintain clinical stability and includes administering plasma exchange and/or dosing with IVIg. In this phase after plasma is exchanged a dose of FcRn antagonist is administered to replace the drug lost in plasma exchange. According to certain embodiments, this post-rescue dose is between 50 and 500 mg of FcRn antagonist (e.g., 150 mg or 300 mg). According to certain embodiments, this post-rescue dose is about 150 mg. In another embodiment, in this post-rescue or third phase a 300 mg dose of is administered after completion of plasmapheresis (e.g., within 6 hours, 5 hours, 4 hours, 3 hours, 2 hours or 1 hour of plasmapheresis).

In certain embodiments, a first one or more induction doses are administered to the subject intravenously, and one or more subsequent maintenance doses are administered subcutaneously.

In certain embodiments, the first 1, 2, 3, or 4 induction doses are administered to the subject intravenously, and 1, 2, 3, or 4 subsequent maintenance doses are administered to the subject subcutaneously.

In certain embodiments, the first 4 induction doses are administered to the subject intravenously, and 1, 2, 3, or 4 subsequent maintenance doses are administered to the subject subcutaneously.

In certain embodiments, 1 dose is administered to the subject intravenously, and 4 subsequent doses are administered to the subject subcutaneously.

In certain embodiments, 2 doses are administered to the subject intravenously, and 4 subsequent doses are administered to the subject subcutaneously.

In one aspect, the instant disclosure provides a method of treating generalized myasthenia gravis in a subject, the method comprising administering to the subject a plurality of doses of an isolated FcRn antagonist, wherein one or more doses of the FcRn antagonist are administered intravenously to the subject in a dose of about 10 mg/kg per dose, and one or more subsequent doses of the FcRn antagonist are administered subcutaneously to the subject in a dose of about 10 mg/kg per dose, thereby treating the generalized myasthenia gravis in the subject. The instant disclosure also provides an isolated FcRn antagonist for use in a method of treating generalized myasthenia gravis in a subject, the method comprising administering to the subject a plurality of doses of the isolated FcRn antagonist, wherein one or more doses of the FcRn antagonist are administered intravenously to the subject in a dose of about 10 mg/kg per dose, and one or more subsequent doses of the FcRn antagonist are administered subcutaneously to the subject in a dose of about 10 mg/kg per dose.

In one aspect, the instant disclosure provides a method of treating generalized myasthenia gravis in a subject, the method comprising administering to the subject a plurality of doses of an isolated FcRn antagonist, wherein one or more doses of the FcRn antagonist are administered intravenously to the subject in a dose of about 10 mg/kg per dose, and one or more subsequent doses of the FcRn antagonist are administered subcutaneously to the subject in a dose of about 20 mg/kg per dose, thereby treating the generalized myasthenia gravis in the subject. The instant disclosure also provides an isolated FcRn antagonist for use in a method of treating generalized myasthenia gravis in a subject, the method comprising administering to the subject a plurality of doses of the isolated FcRn antagonist, wherein one or more doses of the FcRn antagonist are administered intravenously to the subject in a dose of about 10 mg/kg per dose, and one or more subsequent doses of the FcRn antagonist are administered subcutaneously to the subject in a dose of about 20 mg/kg per dose.

In one aspect, the instant disclosure provides a method of treating generalized myasthenia gravis in a subject, the method comprising administering to the subject a plurality of doses of an isolated FcRn antagonist, wherein one or more doses of the FcRn antagonist are administered intravenously to the subject in a dose of about 10 mg/kg per dose, and one or more subsequent doses of the FcRn antagonist are administered subcutaneously to the subject in a dose of about 150 mg per dose, thereby treating the generalized myasthenia gravis in the subject. The instant disclosure also provides an isolated FcRn antagonist for use in a method of treating generalized myasthenia gravis in a subject, the method comprising administering to the subject a plurality of doses of the isolated FcRn antagonist, wherein one or more doses of the FcRn antagonist are administered intravenously to the subject in a dose of about 10 mg/kg per dose, and one or more subsequent doses of the FcRn antagonist are administered subcutaneously to the subject in a dose of about 150 mg per dose.

In one aspect, the instant disclosure provides a method of treating generalized myasthenia gravis in a subject, the method comprising administering to the subject more than one dose of an isolated FcRn antagonist, wherein one or more doses of the FcRn antagonist are administered intravenously to the subject in a dose of about 10 mg/kg per dose, and one or more subsequent doses of the FcRn antagonist are administered subcutaneously to the subject in a dose of about 300 mg per dose, thereby treating the generalized myasthenia gravis in the subject. The instant disclosure also provides an isolated FcRn antagonist for use in a method of treating generalized myasthenia gravis in a subject, the method comprising administering to the subject more than one dose of the isolated FcRn antagonist, wherein one or more doses of the FcRn antagonist are administered intravenously to the subject in a dose of about 10 mg/kg per dose, and one or more subsequent doses of the FcRn antagonist are administered subcutaneously to the subject in a dose of about 300 mg per dose.

In certain embodiments, 1, 2, 3, or 4 doses are administered to the subject intravenously, and wherein 1, 2, 3, or 4 subsequent doses are administered to the subject subcutaneously.

In certain embodiments, 1 dose is administered to the subject intravenously and 1 subsequent dose is administered to the subject subcutaneously.

In certain embodiments, 1 dose is administered to the subject intravenously and 2 subsequent doses are administered to the subject subcutaneously.

In certain embodiments, 1 dose is administered to the subject intravenously and 3 subsequent doses are administered to the subject subcutaneously.

In certain embodiments, 1 dose is administered to the subject intravenously and 4 subsequent doses are administered to the subject subcutaneously.

In certain embodiments, 2 doses are administered to the subject intravenously and 1 subsequent dose is administered to the subject subcutaneously.

In certain embodiments, 2 doses are administered to the subject intravenously and 2 subsequent doses are administered to the subject subcutaneously.

In certain embodiments, 2 doses are administered to the subject intravenously and 3 subsequent doses are administered to the subject subcutaneously.

In certain embodiments, 2 doses are administered to the subject intravenously and 4 subsequent doses are administered to the subject subcutaneously.

In certain embodiments, 3 doses are administered to the subject intravenously and 1 subsequent dose is administered to the subject subcutaneously.

In certain embodiments, 3 doses are administered to the subject intravenously and 2 subsequent doses are administered to the subject subcutaneously.

In certain embodiments, 3 doses are administered to the subject intravenously and 3 subsequent doses are administered to the subject subcutaneously.

In certain embodiments, 3 doses are administered to the subject intravenously and 4 subsequent doses are administered to the subject subcutaneously.

In certain embodiments, 4 doses are administered to the subject intravenously and 1 subsequent dose is administered to the subject subcutaneously.

In certain embodiments, 4 doses are administered to the subject intravenously and 2 subsequent doses are administered to the subject subcutaneously.

In certain embodiments, 4 doses are administered to the subject intravenously and 3 subsequent doses are administered to the subject subcutaneously.

In certain embodiments, 4 doses are administered to the subject intravenously and 4 subsequent doses are administered to the subject subcutaneously.

In certain embodiments, the one or more subcutaneous doses are administered at a frequency selected from the group consisting of about daily, about weekly, about biweekly, and about monthly.

In certain embodiments, one or more doses of the FcRn antagonist are administered as a retreatment, a maintenance dose, or a tapering dose.

The methods disclosed herein can reduce the serum levels of a naturally occurring autoantibody such as anti-AChR. Accordingly, in one aspect the instant disclosure provides methods of treating a subject having an antibody-mediated disorder (e.g. an autoimmune disease, such as generalized myasthenia gravis), the method comprising administering to the subject an effective amount of an FcRn antagonist composition disclosed herein. In certain embodiments, administration of the isolated FcRn antagonist reduces the serum level of an anti-acetylcholine receptor (AChR) antibody. In certain embodiments, administration of the isolated FcRn antagonist reduces the serum level of an anti-MuSK antibody. In certain embodiments, administration of the isolated FcRn antagonist reduces the serum level of an anti-LRP4 antibody. In certain embodiments, the serum level of the antibody is reduced at day 8, 15, 22, 29, or 36 compared to a baseline serum level of the at least antibody as measured prior to administration of the isolated FcRn antagonist at day 1. In certain embodiments, the serum level of the at least one IgG is reduced by at least about 25% to at least about 95% at day 8, 15, 22, 29, or 36. In certain embodiments, the serum level of the at least one IgG is reduced by at least about 50% to at least about 95% at day 8, 15, 22, 29, or 36. In certain embodiments, the serum level of the at least one anti-AchR antibody is reduced by at least about 50% to at least about 85% at day 8, 15, 22, 29, or 36. In certain embodiments, the serum level of anti-MuSK antibody is reduced by at least about 50% to at least about 85% at day 8, 15, 22, 29, or 36. In certain embodiments, the serum level of anti-LRP4 antibody is reduced by at least about 50% to at least about 85% at day 8, 15, 22, 29, or 36.

In certain embodiments, the FcRn antagonist is administered to the subject simultaneously with an additional therapeutic agent. In certain embodiments, the FcRn antagonist is administered to the subject sequentially with an additional therapeutic agent.

In certain embodiments, the dosage of the additional therapeutic agent is tapered in conjunction with treatment with the FcRn antagonist. This is especially useful where the additional therapeutic agent to be tapered is a corticosteroid.

Patient Selection

The methods of the instant disclosure are particularly suited to treating generalized myasthenia gravis in a subject. Accordingly, in certain embodiments, the methods of the invention comprise the selection of a patient for treatment that has been diagnosed as having generalized myasthenia gravis and/or exhibits one or more symptoms associated with generalized myasthenia gravis. In certain aspects of the disclosure, a subset of the generalized MG patient population may be selected for treatment. For example, a patient may be selected for the presence of one of more additional characteristics. In certain embodiments, these patients may exhibit one or more characteristics which render them more difficult to treat than the general MG patient population.

(a) Evaluation Scores

In certain embodiments, the MG patients may exhibit a high degree of impairment as reflected by one or more myasthenia gravis evaluation scores selected from the group consisting of Quantitative Myasthenia Gravis (QMG) score, Myasthenia Gravis activities of daily living (MG-ADL) score, Myasthenia Gravis composite (MGC) score, 15-item Quality of life scale for Myasthenia Gravis (MGQoL15r), and EuroQol 5 Dimension (EQ-5D) score. In certain embodiments, the MG patient may exhibit an MG-ADL score of at least 5. In certain embodiments, the total MG-ADL score is at least 5, at least 6, at least 7, at least 8, at least 9, at least 10, at least 15, or at least 20. In certain embodiments, the MG patient may exhibit a QMG score of at least 10. In certain embodiments, the total QMG score is at least 11, at least 12, at least 13, at least 14, at least 15, at least 20, at least 25, or at least 30. In certain embodiments, the MG patient may exhibit an MGC score of at least 10. In certain embodiments, the MGC score, is at least 15, at least 20, at least 25, at least 30, at least 35, or at least 40. In certain embodiments, the MG patient may exhibit an MGQol 15r score of at least 10. In certain embodiments, the MGQol 15r score, is at least 11, at least 12, at least 13, at least 14, at least 15, at least 20, or at least 25.

In certain embodiments, the MG patient selected for treatment may exhibit an exacerbation of one or more MG symptoms over a period of time. In certain embodiments, the MG patient may exhibit an exacerbation of one or more MG symptoms despite treatment with standard of care therapy.

In certain embodiments, an exacerbation of myasthenia gravis or generalized myasthenia gravis is present when there is at least a 1-point worsening in the MG-ADL score. In certain embodiments, an exacerbation of myasthenia gravis or generalized myasthenia gravis is present when there is at least a 2-point worsening in the MG-ADL score. In certain embodiments, an exacerbation of myasthenia gravis or generalized myasthenia gravis is present when there is at least a 3-point worsening in the MG-ADL score. In certain embodiments, an exacerbation of myasthenia gravis or generalized myasthenia gravis is present when there is at least a 4-point worsening in the MG-ADL score. In certain embodiments, an exacerbation of myasthenia gravis or generalized myasthenia gravis is present when there is at least a 5-point worsening in the MG-ADL score. In certain embodiments, an exacerbation of myasthenia gravis or generalized myasthenia gravis is present when there is at least a 6-point worsening in the MG-ADL score. In certain embodiments, an exacerbation of myasthenia gravis or generalized myasthenia gravis is present when there is at least a 7-point worsening in the MG-ADL score. In certain embodiments, an exacerbation of myasthenia gravis or generalized myasthenia gravis is present when there is at least an 8-point worsening in the MG-ADL score. In certain embodiments, an exacerbation of myasthenia gravis or generalized myasthenia gravis is present when there is at least a 9-point worsening in the MG-ADL score. In certain embodiments, an exacerbation of myasthenia gravis or generalized myasthenia gravis is present when there is at least a 10-point worsening in the MG-ADL score.

In certain embodiments, an exacerbation of myasthenia gravis or generalized myasthenia gravis is present when there is at least a 1-point worsening in the QMG score. In certain embodiments, an exacerbation of myasthenia gravis or generalized myasthenia gravis is present when there is at least a 2-point worsening in the QMG score. In certain embodiments, an exacerbation of myasthenia gravis or generalized myasthenia gravis is present when there is at least a 3-point worsening in the QMG score. In certain embodiments, an exacerbation of myasthenia gravis or generalized myasthenia gravis is present when there is at least a 4-point worsening in the QMG score. In certain embodiments, an exacerbation of myasthenia gravis or generalized myasthenia gravis is present when there is at least a 5-point worsening in the QMG score. In certain embodiments, an exacerbation of myasthenia gravis or generalized myasthenia gravis is present when there is at least a 6-point worsening in the QMG score. In certain embodiments, an exacerbation of myasthenia gravis or generalized myasthenia gravis is present when there is at least a 7-point worsening in the QMG score. In certain embodiments, an exacerbation of myasthenia gravis or generalized myasthenia gravis is present when there is at least an 8-point worsening in the QMG score. In certain embodiments, an exacerbation of myasthenia gravis or generalized myasthenia gravis is present when there is at least a 9-point worsening in the QMG score. In certain embodiments, an exacerbation of myasthenia gravis or generalized myasthenia gravis is present when there is at least a 10-point worsening in the QMG score.

In certain embodiments, an exacerbation of myasthenia gravis or generalized myasthenia gravis is present when there is at least a 1-point worsening in the MGC score. In certain embodiments, an exacerbation of myasthenia gravis or generalized myasthenia gravis is present when there is at least a 2-point worsening in the MGC score. In certain embodiments, an exacerbation of myasthenia gravis or generalized myasthenia gravis is present when there is at least a 3-point worsening in the MGC score. In certain embodiments, an exacerbation of myasthenia gravis or generalized myasthenia gravis is present when there is at least a 4-point worsening in the MGC score. In certain embodiments, an exacerbation of myasthenia gravis or generalized myasthenia gravis is present when there is at least a 5-point worsening in the MGC score. In certain embodiments, an exacerbation of myasthenia gravis or generalized myasthenia gravis is present when there is at least a 6-point worsening in the MGC score. In certain embodiments, an exacerbation of myasthenia gravis or generalized myasthenia gravis is present when there is at least a 7-point worsening in the MGC score. In certain embodiments, an exacerbation of myasthenia gravis or generalized myasthenia gravis is present when there is at least an 8-point worsening in the MGC score. In certain embodiments, an exacerbation of myasthenia gravis or generalized myasthenia gravis is present when there is at least a 9-point worsening in the MGC score. In certain embodiments, an exacerbation of myasthenia gravis or generalized myasthenia gravis is present when there is at least a 10-point worsening in the MGC score.

In certain embodiments, an exacerbation of myasthenia gravis or generalized myasthenia gravis is present when there is at least a 1-point worsening in the MGQoL 15r score. In certain embodiments, an exacerbation of myasthenia gravis or generalized myasthenia gravis is present when there is at least a 2-point worsening in the MGQoL 15r score. In certain embodiments, an exacerbation of myasthenia gravis or generalized myasthenia gravis is present when there is at least a 3-point worsening in the MGQoL 15r score. In certain embodiments, an exacerbation of myasthenia gravis or generalized myasthenia gravis is present when there is at least a 4-point worsening in the MGQoL 15r score. In certain embodiments, an exacerbation of myasthenia gravis or generalized myasthenia gravis is present when there is at least a 5-point worsening in the MGQoL 15r score. In certain embodiments, an exacerbation of myasthenia gravis or generalized myasthenia gravis is present when there is at least a 6-point worsening in the MGQoL 15r score. In certain embodiments, an exacerbation of myasthenia gravis or generalized myasthenia gravis is present when there is at least a 7-point worsening in the MGQoL15r score. In certain embodiments, an exacerbation of myasthenia gravis or generalized myasthenia gravis is present when there is at least an 8-point worsening in the MGQoL15r score. In certain embodiments, an exacerbation of myasthenia gravis or generalized myasthenia gravis is present when there is at least a 9-point worsening in the MGQoL15r score. In certain embodiments, an exacerbation of myasthenia gravis or generalized myasthenia gravis is present when there is at least a 10-point worsening in the MGQoL15r score.

(b) Autoantibodies

In yet other embodiments, the MG patient may be selected as having the presence or absence of one or more autoantibodies. Indeed, generalized MG may be categorized into various subtypes based on the presence of particular autoantibodies.

In one embodiment, the MG patient is selected as being positive for the presence of autoantibodies to the acetylcholine receptor (AChR) antibody ("AChR seropositive" or "AChR-associated MG"). In certain embodiments, the AChR-associated MG patient is selected as being "double seropositive" for both acetylcholine receptor (AChR) antibodies and antibodies against muscle-specific tyrosine kinase (MuSK). In certain embodiments, the AChR-associated MG patient is selected as being seropositive for AChR and seronegative for MuSK. AChR-associated MG has a bimodal age pattern of incidence, with a peak in young adults aged about 30 years and then a steady increase in incidence with increasing age older than 50 years (Heldal et al., "Seropositive myasthenia gravis: a nationwide epidemiologic study. Neurology. 2009; 73: 150-151).

In other embodiments, the MG patient is selected as being positive for the presence of autoantibodies to the MuSK receptor ("MuSK seropositive" or "MuSK-associated MG"). In certain embodiments, the MuSK-associated MG patient is selected as being seronegative for AChR. MuSK antibodies have been detected in approximately one third of AChR-associated MG patients (see Niks et al., J. Neurol. Neurosurg Psychiatry, 2007; 78: 417-18). In other embodiments, the MG patient is selected as being seropositive for AChR, seropositive for MuSK, and seropositive for LRP4. MuSK-associated MG incidence is estimated at 0.3 patient per million per year, with a prevalence of 2.9 per million people (Guptill et al., Muscle Nerve 2011, 44: 36-40).

In other embodiments, the MG patient selected for treatment is a "double seronegative" patient which is seronegative for the presence of both AChR antibodies and MuSK antibodies.

In certain embodiments, the double seronegative patient is positive for the presence of autoantibodies to low-density lipoprotein receptor-related protein 4 (LRP4) ("LRP4 seropositive" or "LRP4-associated MG"). LRP4 antibodies have been recorded in 19% of AChR seronegative patients. Moreover, epidemiological data suggest that LRP4-associated MG is half as frequent as the MUSK form of the disease (Zisimopoulou et al., Autoimmun Rev 2013, 12: 924-30).

In certain embodiments, the MG patient selected for treatment is seropositive for the presence of autoantibodies to agrin. In certain embodiments, the patient is also seropositive for AChR. In another embodiment, the patient is also seropositive for MuSK. In another embodiment, the patient is also seropositive for LRP4.

In certain embodiments, the MG patient selected for treatment is seropositive for the presence of autoantibodies to cortactin, a protein that acts downstream from agrin/MuSK promoting AChR clustering. In certain embodiments, the patient is also seropositive for AChR. In another embodiment, the patient is also seropositive for MuSK. In another embodiment, the patient is also seropositive for LRP4.

In certain embodiments, the MG patient selected from treatment is seropositive for the presence of autoantibodies to titin, a protein which maintains the flexibility of cell structure. The presence of titin autoantibodies may serve as a useful marker for severe MG patients who require long-term immunosuppression and are not responsive to thymectomy.

In certain embodiments, the MG patient selected from treatment is seropositive for the presence of autoantibodies to the ryanodine receptor, which is a sarcoplasmic reticulum calcium channel protein that mediates contraction of the muscle cell. The presence of ryanodine receptor autoantibodies may also serve as a useful marker for severe MG.

In certain embodiments, the MG patient selected for treatment is seropositive for AChR. In certain embodiments, the MG patient selected for treatment is seropositive for AChR and ryanodine receptor. In certain embodiments, the MG patient selected for treatment is seropositive for AChR and titin. In certain embodiments, the MG patient selected for treatment is seropositive for AChR, titin, and ryanodine receptor. In certain embodiments, the MG patient selected for treatment is seropositive for AChR and cortactin. In certain embodiments, the MG patient selected for treatment is seropositive for AChR, cortactin, and ryanodine receptor. In certain embodiments, the MG patient selected for treatment is seropositive for AChR, cortactin, and titin. In certain embodiments, the MG patient selected for treatment is seropositive for AChR, cortactin, titin, and ryanodine receptor. In certain embodiments, the MG patient selected for treatment is seropositive for AChR and agrin. In certain embodiments, the MG patient selected for treatment is seropositive for AChR, agrin, and ryanodine receptor. In certain embodiments, the MG patient selected for treatment is seropositive for AChR, agrin, and titin. In certain embodiments, the MG patient selected for treatment is seropositive for AChR, agrin, titin, and ryanodine receptor. In certain embodiments, the MG patient selected for treatment is seropositive for AChR, agrin, and cortactin. In certain embodiments, the MG patient selected for treatment is seropositive for AChR, agrin, cortactin, and ryanodine receptor.

In certain embodiments, the MG patient selected for treatment is seropositive for AChR, agrin, cortactin, and titin. In certain embodiments, the MG patient selected for treatment is seropositive for AChR, agrin, cortactin, titin, and ryanodine receptor. In certain embodiments, the MG patient selected for treatment is seropositive for AChR and LRP4. In certain embodiments, the MG patient selected for treatment is seropositive for AChR, LRP4, and ryanodine receptor. In certain embodiments, the MG patient selected for treatment is seropositive for AChR, LRP4, and titin. In certain embodiments, the MG patient selected for treatment is seropositive for AChR, LRP4, titin, and ryanodine receptor. In certain embodiments, the MG patient selected for treatment is seropositive for AChR, LRP4, and cortactin. In certain embodiments, the MG patient selected for treatment is seropositive for AChR, LRP4, cortactin, and ryanodine receptor. In certain embodiments, the MG patient selected for treatment is seropositive for AChR, LRP4, cortactin, and titin. In certain embodiments, the MG patient selected for treatment is seropositive for AChR, LRP4, cortactin, titin, and ryanodine receptor.

In certain embodiments, the MG patient selected for treatment is seropositive for AChR, LRP4, and agrin. In certain embodiments, the MG patient selected for treatment is seropositive for AChR, LRP4, agrin, and ryanodine receptor. In certain embodiments, the MG patient selected for treatment is seropositive for AChR, LRP4, agrin, and titin. In certain embodiments, the MG patient selected for treatment is seropositive for AChR, LRP4, agrin, titin, and ryanodine receptor. In certain embodiments, the MG patient selected for treatment is seropositive for AChR, LRP4, agrin, and cortactin. In certain embodiments, the MG patient selected for treatment is seropositive for AChR, LRP4, agrin, cortactin, and ryanodine receptor. In certain embodiments, the MG patient selected for treatment is seropositive for AChR, LRP4, agrin, cortactin, and titin. In certain embodiments, the MG patient selected for treatment is seropositive for AChR, LRP4, agrin, cortactin, titin, and ryanodine receptor.

In certain embodiments, the MG patient selected for treatment is seropositive for AChR and MuSK. In certain embodiments, the MG patient selected for treatment is seropositive for AChR, MuSK, and ryanodine receptor. In certain embodiments, the MG patient selected for treatment is seropositive for AChR, MuSK, and titin. In certain embodiments, the MG patient selected for treatment is seropositive for AChR, MuSK, titin, and ryanodine receptor. In certain embodiments, the MG patient selected for treatment is seropositive for AChR, MuSK, and cortactin. In certain embodiments, the MG patient selected for treatment is seropositive for AChR, MuSK, cortactin, and ryanodine receptor. In certain embodiments, the MG patient selected for treatment is seropositive for AChR, MuSK, cortactin, and titin. In certain embodiments, the MG patient selected for treatment is seropositive for AChR, MuSK, cortactin, titin, and ryanodine receptor. In certain embodiments, the MG patient selected for treatment is seropositive for AChR, MuSK, and agrin. In certain embodiments, the MG patient selected for treatment is seropositive for AChR, MuSK, agrin, and ryanodine receptor. In certain embodiments, the MG patient selected for treatment is seropositive for AChR, MuSK, agrin, and titin. In certain embodiments, the MG patient selected for treatment is seropositive for AChR, MuSK, agrin, titin, and ryanodine receptor. In certain embodiments, the MG patient selected for treatment is seropositive for AChR, MuSK, agrin, and cortactin. In certain embodiments, the MG patient selected for treatment is seropositive for AChR, MuSK, agrin, cortactin, and ryanodine receptor. In certain embodiments, the MG patient selected for treatment is seropositive for AChR, MuSK, agrin, cortactin, and titin. In certain embodiments, the MG patient selected for treatment is seropositive for AChR, MuSK, agrin, cortactin, titin, and ryanodine receptor. In certain embodiments, the MG patient selected for treatment is seropositive for AChR, MuSK, and LRP4. In certain embodiments, the MG patient selected for treatment is seropositive for AChR, MuSK, LRP4, and ryanodine receptor. In certain embodiments, the MG patient selected for treatment is seropositive for AChR, MuSK, LRP4, and titin. In certain embodiments, the MG patient selected for treatment is seropositive for AChR, MuSK, LRP4, titin, and ryanodine receptor. In certain embodiments, the MG patient selected for treatment is seropositive for AChR, MuSK, LRP4, and cortactin. In certain embodiments, the MG patient selected for treatment is seropositive for AChR, MuSK, LRP4, cortactin, and ryanodine receptor.

In certain embodiments, the MG patient selected for treatment is seropositive for AChR, MuSK, LRP4, cortactin, and titin. In certain embodiments, the MG patient selected for treatment is seropositive for AChR, MuSK, LRP4, cortactin, titin, and ryanodine receptor. In certain embodiments, the MG patient selected for treatment is seropositive for AChR, MuSK, LRP4, and agrin. In certain embodiments, the MG patient selected for treatment is seropositive for AChR, MuSK, LRP4, agrin, and ryanodine receptor. In certain embodiments, the MG patient selected for treatment is seropositive for AChR, MuSK, LRP4, agrin, and titin.

In certain embodiments, the MG patient selected for treatment is seropositive for AChR, MuSK, LRP4, agrin, titin, and ryanodine receptor. In certain embodiments, the MG patient selected for treatment is seropositive for AChR, MuSK, LRP4, agrin, and cortactin. In certain embodiments, the MG patient selected for treatment is seropositive for AChR, MuSK, LRP4, agrin, cortactin, and ryanodine receptor. In certain embodiments, the MG patient selected for treatment is seropositive for AChR, MuSK, LRP4, agrin, cortactin, and titin. In certain embodiments, the MG patient selected for treatment is seropositive for AChR, MuSK, LRP4, agrin, cortactin, titin, and ryanodine receptor. In certain embodiments, the MG patient selected for treatment is seropositive for MuSK. In certain embodiments, the MG patient selected for treatment is seropositive for MuSK and ryanodine receptor. In certain embodiments, the MG patient selected for treatment is seropositive for MuSK and titin. In certain embodiments, the MG patient selected for treatment is seropositive for MuSK, titin, and ryanodine receptor. In certain embodiments, the MG patient selected for treatment is seropositive for MuSK and cortactin. In certain embodiments, the MG patient selected for treatment is seropositive for MuSK, cortactin, and ryanodine receptor. In certain embodiments, the MG patient selected for treatment is seropositive for MuSK, cortactin, and titin. In certain embodiments, the MG patient selected for treatment is seropositive for MuSK, cortactin, titin, and ryanodine receptor. In certain embodiments, the MG patient selected for treatment is seropositive for MuSK and agrin. In certain embodiments, the MG patient selected for treatment is seropositive for MuSK, agrin, and ryanodine receptor. In certain embodiments, the MG patient selected for treatment is seropositive for MuSK, agrin, and titin. In certain embodiments, the MG patient selected for treatment is seropositive for MuSK, agrin, titin, and ryanodine receptor. In certain embodiments, the MG patient selected for treatment is seropositive for MuSK, agrin, and cortactin. In certain embodiments, the MG patient selected for treatment is seropositive for MuSK, agrin, cortactin, and ryanodine receptor. In certain embodiments, the MG patient selected for treatment is seropositive for MuSK, agrin, cortactin, and titin. In certain embodiments, the MG patient selected for treatment is seropositive for MuSK, agrin, cortactin, titin, and ryanodine receptor. In certain embodiments, the MG patient selected for treatment is seropositive for MuSK and LRP4. In certain embodiments, the MG patient selected for treatment is seropositive for MuSK, LRP4, and ryanodine receptor. In certain embodiments, the MG patient selected for treatment is seropositive for MuSK, LRP4, and titin. In certain embodiments, the MG patient selected for treatment is seropositive for MuSK, LRP4, titin, and ryanodine receptor. In certain embodiments, the MG patient selected for treatment is seropositive for MuSK, LRP4, and cortactin. In certain embodiments, the MG patient selected for treatment is seropositive for MuSK, LRP4, cortactin, and ryanodine receptor. In certain embodiments, the MG patient selected for treatment is seropositive for MuSK, LRP4, cortactin, and titin. In certain embodiments, the MG patient selected for treatment is seropositive for MuSK, LRP4, cortactin, titin, and ryanodine receptor. In certain embodiments, the MG patient selected for treatment is seropositive for MuSK, LRP4, and agrin. In certain embodiments, the MG patient selected for treatment is seropositive for MuSK, LRP4, agrin, and ryanodine receptor. n certain embodiments, the MG patient selected for treatment is seropositive for MuSK, LRP4, agrin, and titin. In certain embodiments, the MG patient selected for treatment is seropositive for MuSK, LRP4, agrin, titin, and ryanodine receptor. In certain embodiments, the MG patient selected for treatment is seropositive for MuSK, LRP4, agrin, and cortactin. In certain embodiments, the MG patient selected for treatment is seropositive for MuSK, LRP4, agrin, cortactin, and ryanodine receptor. In certain embodiments, the MG patient selected for treatment is seropositive for MuSK, LRP4, agrin, cortactin, and titin. In certain embodiments, the MG patient selected for treatment is seropositive for MuSK, LRP4, agrin, cortactin, titin, and ryanodine receptor. In certain embodiments, the MG patient selected for treatment is seropositive for LRP4.

In certain embodiments, the MG patient selected for treatment is seropositive for LRP4 and ryanodine receptor. In certain embodiments, the MG patient selected for treatment is seropositive for LRP4 and titin. In certain embodiments, the MG patient selected for treatment is seropositive for LRP4, titin, and ryanodine receptor. In certain embodiments, the MG patient selected for treatment is seropositive for LRP4 and cortactin. In certain embodiments, the MG patient selected for treatment is seropositive for LRP4, cortactin, and ryanodine receptor. In certain embodiments, the MG patient selected for treatment is seropositive for LRP4, cortactin, and titin. In certain embodiments, the MG patient selected for treatment is seropositive for LRP4, cortactin, titin, and ryanodine receptor. In certain embodiments, the MG patient selected for treatment is seropositive for LRP4 and agrin. In certain embodiments, the MG patient selected for treatment is seropositive for LRP4, agrin, and ryanodine receptor. In certain embodiments, the MG patient selected for treatment is seropositive for LRP4, agrin, and titin. In certain embodiments, the MG patient selected for treatment is seropositive for LRP4, agrin, titin, and ryanodine receptor. In certain embodiments, the MG patient selected for treatment is seropositive for LRP4, agrin, and cortactin. In certain embodiments, the MG patient selected for treatment is seropositive for LRP4, agrin, cortactin, and ryanodine receptor. In certain embodiments, the MG patient selected for treatment is seropositive for LRP4, agrin, cortactin, and titin. In certain embodiments, the MG patient selected for treatment is seropositive for LRP4, agrin, cortactin, titin, and ryanodine receptor. In certain embodiments, the MG patient selected for treatment is seropositive for agrin. In certain embodiments, the MG patient selected for treatment is seropositive for agrin and ryanodine receptor. In certain embodiments, the MG patient selected for treatment is seropositive for agrin and titin. In certain embodiments, the MG patient selected for treatment is seropositive for agrin, titin, and ryanodine receptor. In certain embodiments, the MG patient selected for treatment is seropositive for agrin and cortactin. In certain embodiments, the MG patient selected for treatment is seropositive for agrin, cortactin, and ryanodine receptor. In certain embodiments, the MG patient selected for treatment is seropositive for agrin, cortactin, and titin. In certain embodiments, the MG patient selected for treatment is seropositive for agrin, cortactin, titin, and ryanodine receptor. In certain embodiments, the MG patient selected for treatment is seropositive for cortactin. In certain embodiments, the MG patient selected for treatment is seropositive for cortactin and ryanodine receptor. In certain embodiments, the MG patient selected for treatment is seropositive for cortactin and titin. In certain embodiments, the MG patient selected for treatment is seropositive for cortactin, titin, and ryanodine receptor. In certain embodiments, the MG patient selected for treatment is seropositive for titin. In certain embodiments, the MG patient selected for treatment is seropositive for titin and ryanodine receptor. In certain embodiments, the MG patient selected for treatment is seropositive for ryanodine receptor. In certain embodiments, the MG patient selected for treatment is seropositive for AChR and is seronegative for MuSK, LRP4, agrin, cortactin, titin, and ryanodine receptor. In certain embodiments, the MG patient selected for treatment is seropositive for AChR and ryanodine receptor and is seronegative for MuSK, LRP4, agrin, cortactin, and titin. In certain embodiments, the MG patient selected for treatment is seropositive for AChR and titin and is seronegative for MuSK, LRP4, agrin, cortactin, and ryanodine receptor. In certain embodiments, the MG patient selected for treatment is seropositive for AChR, titin, and ryanodine receptor and is seronegative for MuSK, LRP4, agrin, and cortactin. In certain embodiments, the MG patient selected for treatment is seropositive for AChR and cortactin and is seronegative for MuSK, LRP4, agrin, titin, and ryanodine receptor.

In certain embodiments, the MG patient selected for treatment is seropositive for AChR, cortactin, and ryanodine receptor and is seronegative for MuSK, LRP4, agrin, and titin. In certain embodiments, the MG patient selected for treatment is seropositive for AChR, cortactin, and titin and is seronegative for MuSK, LRP4, agrin, and ryanodine receptor. In certain embodiments, the MG patient selected for treatment is seropositive for AChR, cortactin, titin, and ryanodine receptor and is seronegative for MuSK, LRP4, and agrin. In certain embodiments, the MG patient selected for treatment is seropositive for AChR and agrin and is seronegative for MuSK, LRP4, cortactin, titin, and ryanodine receptor. In certain embodiments, the MG patient selected for treatment is seropositive for AChR, agrin, and ryanodine receptor and is seronegative for MuSK, LRP4, cortactin, and titin. In certain embodiments, the MG patient selected for treatment is seropositive for AChR, agrin, and titin and is seronegative for MuSK, LRP4, cortactin, and ryanodine receptor. In certain embodiments, the MG patient selected for treatment is seropositive for AChR, agrin, titin, and ryanodine receptor and is seronegative for MuSK, LRP4, and cortactin. In certain embodiments, the MG patient selected for treatment is seropositive for AChR, agrin, and cortactin and is seronegative for MuSK, LRP4, titin, and ryanodine receptor. In certain embodiments, the MG patient selected for treatment is seropositive for AChR, agrin, cortactin, and ryanodine receptor and is seronegative for MuSK, LRP4, and titin. In certain embodiments, the MG patient selected for treatment is seropositive for AChR, agrin, cortactin, and titin and is seronegative for MuSK, LRP4, and ryanodine receptor. In certain embodiments, the MG patient selected for treatment is seropositive for AChR, agrin, cortactin, titin, and ryanodine receptor and is seronegative for MuSK and LRP4.

In certain embodiments, the MG patient selected for treatment is seropositive for AChR and LRP4 and is seronegative for MuSK, agrin, cortactin, titin, and ryanodine receptor.

In certain embodiments, the MG patient selected for treatment is seropositive for AChR, LRP4, and ryanodine receptor and is seronegative for MuSK, agrin, cortactin, and titin.

In certain embodiments, the MG patient selected for treatment is seropositive for AChR, LRP4, and titin and is seronegative for MuSK, agrin, cortactin, and ryanodine receptor.

In certain embodiments, the MG patient selected for treatment is seropositive for AChR, LRP4, titin, and ryanodine receptor and is seronegative for MuSK, agrin, and cortactin.

In certain embodiments, the MG patient selected for treatment is seropositive for AChR, LRP4, and cortactin and is seronegative for MuSK, agrin, titin, and ryanodine receptor.

In certain embodiments, the MG patient selected for treatment is seropositive for AChR, LRP4, cortactin, and ryanodine receptor and is seronegative for MuSK, agrin, and titin.

In certain embodiments, the MG patient selected for treatment is seropositive for AChR, LRP4, cortactin, and titin and is seronegative for MuSK, agrin, and ryanodine receptor.

In certain embodiments, the MG patient selected for treatment is seropositive for AChR, LRP4, cortactin, titin, and ryanodine receptor and is seronegative for MuSK and agrin.

In certain embodiments, the MG patient selected for treatment is seropositive for AChR, LRP4, and agrin and is seronegative for MuSK, cortactin, titin, and ryanodine receptor.

In certain embodiments, the MG patient selected for treatment is seropositive for AChR, LRP4, agrin, and ryanodine receptor and is seronegative for MuSK, cortactin, and titin.

In certain embodiments, the MG patient selected for treatment is seropositive for AChR, LRP4, agrin, and titin and is seronegative for MuSK, cortactin, and ryanodine receptor.

In certain embodiments, the MG patient selected for treatment is seropositive for AChR, LRP4, agrin, titin, and ryanodine receptor and is seronegative for MuSK and cortactin.

In certain embodiments, the MG patient selected for treatment is seropositive for AChR, LRP4, agrin, and cortactin and is seronegative for MuSK, titin, and ryanodine receptor.

In certain embodiments, the MG patient selected for treatment is seropositive for AChR, LRP4, agrin, cortactin, and ryanodine receptor and is seronegative for MuSK and titin.

In certain embodiments, the MG patient selected for treatment is seropositive for AChR, LRP4, agrin, cortactin, and titin and is seronegative for MuSK and ryanodine receptor.

In certain embodiments, the MG patient selected for treatment is seropositive for AChR, LRP4, agrin, cortactin, titin, and ryanodine receptor and is seronegative for MuSK.

In certain embodiments, the MG patient selected for treatment is seropositive for AChR and MuSK and is seronegative for LRP4, agrin, cortactin, titin, and ryanodine receptor.

In certain embodiments, the MG patient selected for treatment is seropositive for AChR, MuSK, and ryanodine receptor and is seronegative for LRP4, agrin, cortactin, and titin.

In certain embodiments, the MG patient selected for treatment is seropositive for AChR, MuSK, and titin and is seronegative for LRP4, agrin, cortactin, and ryanodine receptor.

In certain embodiments, the MG patient selected for treatment is seropositive for AChR, MuSK, titin, and ryanodine receptor and is seronegative for LRP4, agrin, and cortactin.

In certain embodiments, the MG patient selected for treatment is seropositive for AChR, MuSK, and cortactin and is seronegative for LRP4, agrin, titin, and ryanodine receptor.

In certain embodiments, the MG patient selected for treatment is seropositive for AChR, MuSK, cortactin, and ryanodine receptor and is seronegative for LRP4, agrin, and titin.

In certain embodiments, the MG patient selected for treatment is seropositive for AChR, MuSK, cortactin, and titin and is seronegative for LRP4, agrin, and ryanodine receptor.

In certain embodiments, the MG patient selected for treatment is seropositive for AChR, MuSK, cortactin, titin, and ryanodine receptor and is seronegative for LRP4 and agrin.

In certain embodiments, the MG patient selected for treatment is seropositive for AChR, MuSK, and agrin and is seronegative for LRP4, cortactin, titin, and ryanodine receptor.

In certain embodiments, the MG patient selected for treatment is seropositive for AChR, MuSK, agrin, and ryanodine receptor and is seronegative for LRP4, cortactin, and titin.

In certain embodiments, the MG patient selected for treatment is seropositive for AChR, MuSK, agrin, and titin and is seronegative for LRP4, cortactin, and ryanodine receptor.

In certain embodiments, the MG patient selected for treatment is seropositive for AChR, MuSK, agrin, titin, and ryanodine receptor and is seronegative for LRP4 and cortactin.

In certain embodiments, the MG patient selected for treatment is seropositive for AChR, MuSK, agrin, and cortactin and is seronegative for LRP4, titin, and ryanodine receptor.

In certain embodiments, the MG patient selected for treatment is seropositive for AChR, MuSK, agrin, cortactin, and ryanodine receptor and is seronegative for LRP4 and titin.

In certain embodiments, the MG patient selected for treatment is seropositive for AChR, MuSK, agrin, cortactin, and titin and is seronegative for LRP4 and ryanodine receptor.

In certain embodiments, the MG patient selected for treatment is seropositive for AChR, MuSK, agrin, cortactin, titin, and ryanodine receptor and is seronegative for LRP4.

In certain embodiments, the MG patient selected for treatment is seropositive for AChR, MuSK, and LRP4 and is seronegative for agrin, cortactin, titin, and ryanodine receptor.

In certain embodiments, the MG patient selected for treatment is seropositive for AChR, MuSK, LRP4, and ryanodine receptor and is seronegative for agrin, cortactin, and titin.

In certain embodiments, the MG patient selected for treatment is seropositive for AChR, MuSK, LRP4, and titin and is seronegative for agrin, cortactin, and ryanodine receptor.

In certain embodiments, the MG patient selected for treatment is seropositive for AChR, MuSK, LRP4, titin, and ryanodine receptor and is seronegative for agrin and cortactin.

In certain embodiments, the MG patient selected for treatment is seropositive for AChR, MuSK, LRP4, and cortactin and is seronegative for agrin, titin, and ryanodine receptor.

In certain embodiments, the MG patient selected for treatment is seropositive for AChR, MuSK, LRP4, cortactin, and ryanodine receptor and is seronegative for agrin and titin.

In certain embodiments, the MG patient selected for treatment is seropositive for AChR, MuSK, LRP4, cortactin, and titin and is seronegative for agrin and ryanodine receptor.

In certain embodiments, the MG patient selected for treatment is seropositive for AChR, MuSK, LRP4, cortactin, titin, and ryanodine receptor and is seronegative for agrin.

In certain embodiments, the MG patient selected for treatment is seropositive for AChR, MuSK, LRP4, and agrin and is seronegative for cortactin, titin, and ryanodine receptor.

In certain embodiments, the MG patient selected for treatment is seropositive for AChR, MuSK, LRP4, agrin, and ryanodine receptor and is seronegative for cortactin and titin.

In certain embodiments, the MG patient selected for treatment is seropositive for AChR, MuSK, LRP4, agrin, and titin and is seronegative for cortactin and ryanodine receptor.

In certain embodiments, the MG patient selected for treatment is seropositive for AChR, MuSK, LRP4, agrin, titin, and ryanodine receptor and is seronegative for cortactin.

In certain embodiments, the MG patient selected for treatment is seropositive for AChR, MuSK, LRP4, agrin, and cortactin and is seronegative for titin and ryanodine receptor.

In certain embodiments, the MG patient selected for treatment is seropositive for AChR, MuSK, LRP4, agrin, cortactin, and ryanodine receptor and is seronegative for titin.

In certain embodiments, the MG patient selected for treatment is seropositive for AChR, MuSK, LRP4, agrin, cortactin, and titin and is seronegative for ryanodine receptor.

In certain embodiments, the MG patient selected for treatment is seropositive for MuSK and is seronegative for AChR, LRP4, agrin, cortactin, titin, and ryanodine receptor.

In certain embodiments, the MG patient selected for treatment is seropositive for MuSK and ryanodine receptor and is seronegative for AChR, LRP4, agrin, cortactin, and titin.

In certain embodiments, the MG patient selected for treatment is seropositive for MuSK and titin and is seronegative for AChR, LRP4, agrin, cortactin, and ryanodine receptor.

In certain embodiments, the MG patient selected for treatment is seropositive for MuSK, titin, and ryanodine receptor and is seronegative for AChR, LRP4, agrin, and cortactin.

In certain embodiments, the MG patient selected for treatment is seropositive for MuSK and cortactin and is seronegative for AChR, LRP4, agrin, titin, and ryanodine receptor.

In certain embodiments, the MG patient selected for treatment is seropositive for MuSK, cortactin, and ryanodine receptor and is seronegative for AChR, LRP4, agrin, and titin.

In certain embodiments, the MG patient selected for treatment is seropositive for MuSK, cortactin, and titin and is seronegative for AChR, LRP4, agrin, and ryanodine receptor.

In certain embodiments, the MG patient selected for treatment is seropositive for MuSK, cortactin, titin, and ryanodine receptor and is seronegative for AChR, LRP4, and agrin.

In certain embodiments, the MG patient selected for treatment is seropositive for MuSK and agrin and is seronegative for AChR, LRP4, cortactin, titin, and ryanodine receptor.

In certain embodiments, the MG patient selected for treatment is seropositive for MuSK, agrin, and ryanodine receptor and is seronegative for AChR, LRP4, cortactin, and titin.

In certain embodiments, the MG patient selected for treatment is seropositive for MuSK, agrin, and titin and is seronegative for AChR, LRP4, cortactin, and ryanodine receptor.

In certain embodiments, the MG patient selected for treatment is seropositive for MuSK, agrin, titin, and ryanodine receptor and is seronegative for AChR, LRP4, and cortactin.

In certain embodiments, the MG patient selected for treatment is seropositive for MuSK, agrin, and cortactin and is seronegative for AChR, LRP4, titin, and ryanodine receptor.

In certain embodiments, the MG patient selected for treatment is seropositive for MuSK, agrin, cortactin, and ryanodine receptor and is seronegative for AChR, LRP4, and titin.

In certain embodiments, the MG patient selected for treatment is seropositive for MuSK, agrin, cortactin, and titin and is seronegative for AChR, LRP4, and ryanodine receptor.

In certain embodiments, the MG patient selected for treatment is seropositive for MuSK, agrin, cortactin, titin, and ryanodine receptor and is seronegative for AChR and LRP4.

In certain embodiments, the MG patient selected for treatment is seropositive for MuSK and LRP4 and is seronegative for AChR, agrin, cortactin, titin, and ryanodine receptor.

In certain embodiments, the MG patient selected for treatment is seropositive for MuSK, LRP4, and ryanodine receptor and is seronegative for AChR, agrin, cortactin, and titin.

In certain embodiments, the MG patient selected for treatment is seropositive for MuSK, LRP4, and titin and is seronegative for AChR, agrin, cortactin, and ryanodine receptor.

In certain embodiments, the MG patient selected for treatment is seropositive for MuSK, LRP4, titin, and ryanodine receptor and is seronegative for AChR, agrin, and cortactin.

In certain embodiments, the MG patient selected for treatment is seropositive for MuSK, LRP4, and cortactin and is seronegative for AChR, agrin, titin, and ryanodine receptor.

In certain embodiments, the MG patient selected for treatment is seropositive for MuSK, LRP4, cortactin, and ryanodine receptor and is seronegative for AChR, agrin, and titin.

In certain embodiments, the MG patient selected for treatment is seropositive for MuSK, LRP4, cortactin, and titin and is seronegative for AChR, agrin, and ryanodine receptor.

In certain embodiments, the MG patient selected for treatment is seropositive for MuSK, LRP4, cortactin, titin, and ryanodine receptor and is seronegative for AChR and agrin.

In certain embodiments, the MG patient selected for treatment is seropositive for MuSK, LRP4, and agrin and is seronegative for AChR, cortactin, titin, and ryanodine receptor.

In certain embodiments, the MG patient selected for treatment is seropositive for MuSK, LRP4, agrin, and ryanodine receptor and is seronegative for AChR, cortactin, and titin.

In certain embodiments, the MG patient selected for treatment is seropositive for MuSK, LRP4, agrin, and titin and is seronegative for AChR, cortactin, and ryanodine receptor.

In certain embodiments, the MG patient selected for treatment is seropositive for MuSK, LRP4, agrin, titin, and ryanodine receptor and is seronegative for AChR and cortactin.

In certain embodiments, the MG patient selected for treatment is seropositive for MuSK, LRP4, agrin, and cortactin and is seronegative for AChR, titin, and ryanodine receptor.

In certain embodiments, the MG patient selected for treatment is seropositive for MuSK, LRP4, agrin, cortactin, and ryanodine receptor and is seronegative for AChR and titin.

In certain embodiments, the MG patient selected for treatment is seropositive for MuSK, LRP4, agrin, cortactin, and titin and is seronegative for AChR and ryanodine receptor.

In certain embodiments, the MG patient selected for treatment is seropositive for MuSK, LRP4, agrin, cortactin, titin, and ryanodine receptor and is seronegative for AChR.

In certain embodiments, the MG patient selected for treatment is seropositive for LRP4 and is seronegative for AChR, MuSK, agrin, cortactin, titin, and ryanodine receptor.

In certain embodiments, the MG patient selected for treatment is seropositive for LRP4 and ryanodine receptor and is seronegative for AChR, MuSK, agrin, cortactin, and titin.

In certain embodiments, the MG patient selected for treatment is seropositive for LRP4 and titin and is seronegative for AChR, MuSK, agrin, cortactin, and ryanodine receptor.

In certain embodiments, the MG patient selected for treatment is seropositive for LRP4, titin, and ryanodine receptor and is seronegative for AChR, MuSK, agrin, and cortactin.

In certain embodiments, the MG patient selected for treatment is seropositive for LRP4 and cortactin and is seronegative for AChR, MuSK, agrin, titin, and ryanodine receptor.

In certain embodiments, the MG patient selected for treatment is seropositive for LRP4, cortactin, and ryanodine receptor and is seronegative for AChR, MuSK, agrin, and titin.

In certain embodiments, the MG patient selected for treatment is seropositive for LRP4, cortactin, and titin and is seronegative for AChR, MuSK, agrin, and ryanodine receptor.

In certain embodiments, the MG patient selected for treatment is seropositive for LRP4, cortactin, titin, and ryanodine receptor and is seronegative for AChR, MuSK, and agrin.

In certain embodiments, the MG patient selected for treatment is seropositive for LRP4 and agrin and is seronegative for AChR, MuSK, cortactin, titin, and ryanodine receptor.

In certain embodiments, the MG patient selected for treatment is seropositive for LRP4, agrin, and ryanodine receptor and is seronegative for AChR, MuSK, cortactin, and titin.

In certain embodiments, the MG patient selected for treatment is seropositive for LRP4, agrin, and titin and is seronegative for AChR, MuSK, cortactin, and ryanodine receptor.

In certain embodiments, the MG patient selected for treatment is seropositive for LRP4, agrin, titin, and ryanodine receptor and is seronegative for AChR, MuSK, and cortactin.

In certain embodiments, the MG patient selected for treatment is seropositive for LRP4, agrin, and cortactin and is seronegative for AChR, MuSK, titin, and ryanodine receptor.

In certain embodiments, the MG patient selected for treatment is seropositive for LRP4, agrin, cortactin, and ryanodine receptor and is seronegative for AChR, MuSK, and titin.

In certain embodiments, the MG patient selected for treatment is seropositive for LRP4, agrin, cortactin, and titin and is seronegative for AChR, MuSK, and ryanodine receptor.

In certain embodiments, the MG patient selected for treatment is seropositive for LRP4, agrin, cortactin, titin, and ryanodine receptor and is seronegative for AChR and MuSK.

In certain embodiments, the MG patient selected for treatment is seropositive for agrin and is seronegative for AChR, MuSK, LRP4, cortactin, titin, and ryanodine receptor.

In certain embodiments, the MG patient selected for treatment is seropositive for agrin and ryanodine receptor and is seronegative for AChR, MuSK, LRP4, cortactin, and titin.

In certain embodiments, the MG patient selected for treatment is seropositive for agrin and titin and is seronegative for AChR, MuSK, LRP4, cortactin, and ryanodine receptor.

In certain embodiments, the MG patient selected for treatment is seropositive for agrin, titin, and ryanodine receptor and is seronegative for AChR, MuSK, LRP4, and cortactin.

In certain embodiments, the MG patient selected for treatment is seropositive for agrin and cortactin and is seronegative for AChR, MuSK, LRP4, titin, and ryanodine receptor.

In certain embodiments, the MG patient selected for treatment is seropositive for agrin, cortactin, and ryanodine receptor and is seronegative for AChR, MuSK, LRP4, and titin.

In certain embodiments, the MG patient selected for treatment is seropositive for agrin, cortactin, and titin and is seronegative for AChR, MuSK, LRP4, and ryanodine receptor.

In certain embodiments, the MG patient selected for treatment is seropositive for agrin, cortactin, titin, and ryanodine receptor and is seronegative for AChR, MuSK, and LRP4.

In certain embodiments, the MG patient selected for treatment is seropositive for cortactin and is seronegative for AChR, MuSK, LRP4, agrin, titin, and ryanodine receptor.

In certain embodiments, the MG patient selected for treatment is seropositive for cortactin and ryanodine receptor and is seronegative for AChR, MuSK, LRP4, agrin, and titin.

In certain embodiments, the MG patient selected for treatment is seropositive for cortactin and titin and is seronegative for AChR, MuSK, LRP4, agrin, and ryanodine receptor.

In certain embodiments, the MG patient selected for treatment is seropositive for cortactin, titin, and ryanodine receptor and is seronegative for AChR, MuSK, LRP4, and agrin.

In certain embodiments, the MG patient selected for treatment is seropositive for titin and is seronegative for AChR, MuSK, LRP4, agrin, cortactin, and ryanodine receptor.

In certain embodiments, the MG patient selected for treatment is seropositive for titin and ryanodine receptor and is seronegative for AChR, MuSK, LRP4, agrin, and cortactin.

In certain embodiments, the MG patient selected for treatment is seropositive for ryanodine receptor and is seronegative for AChR, MuSK, LRP4, agrin, cortactin, and titin.

In certain embodiments, the MG patient selected for treatment is seropositive for AChR and seronegative for ryanodine receptor.

In certain embodiments, the MG patient selected for treatment is seropositive for AChR and seronegative for titin.

In certain embodiments, the MG patient selected for treatment is seropositive for AChR and seronegative for titin and ryanodine receptor.

In certain embodiments, the MG patient selected for treatment is seropositive for AChR and seronegative for cortactin.

In certain embodiments, the MG patient selected for treatment is seropositive for AChR and seronegative for cortactin and ryanodine receptor.

In certain embodiments, the MG patient selected for treatment is seropositive for AChR and seronegative for cortactin and titin.

In certain embodiments, the MG patient selected for treatment is seropositive for AChR and seronegative for cortactin, titin, and ryanodine receptor.

In certain embodiments, the MG patient selected for treatment is seropositive for AChR and seronegative for agrin.

In certain embodiments, the MG patient selected for treatment is seropositive for AChR and seronegative for agrin and ryanodine receptor.

In certain embodiments, the MG patient selected for treatment is seropositive for AChR and seronegative for agrin and titin.

In certain embodiments, the MG patient selected for treatment is seropositive for AChR and seronegative for agrin, titin, and ryanodine receptor.

In certain embodiments, the MG patient selected for treatment is seropositive for AChR and seronegative for agrin and cortactin.

In certain embodiments, the MG patient selected for treatment is seropositive for AChR and seronegative for agrin, cortactin, and ryanodine receptor.

In certain embodiments, the MG patient selected for treatment is seropositive for AChR and seronegative for agrin, cortactin, and titin.

In certain embodiments, the MG patient selected for treatment is seropositive for AChR and seronegative for agrin, cortactin, titin, and ryanodine receptor.

In certain embodiments, the MG patient selected for treatment is seropositive for AChR and seronegative for LRP4.

In certain embodiments, the MG patient selected for treatment is seropositive for AChR and seronegative for LRP4 and ryanodine receptor.

In certain embodiments, the MG patient selected for treatment is seropositive for AChR and seronegative for LRP4 and titin.

In certain embodiments, the MG patient selected for treatment is seropositive for AChR and seronegative for LRP4, titin, and ryanodine receptor.

In certain embodiments, the MG patient selected for treatment is seropositive for AChR and seronegative for LRP4 and cortactin.

In certain embodiments, the MG patient selected for treatment is seropositive for AChR and seronegative for LRP4, cortactin, and ryanodine receptor.

In certain embodiments, the MG patient selected for treatment is seropositive for AChR and seronegative for LRP4, cortactin, and titin.

In certain embodiments, the MG patient selected for treatment is seropositive for AChR and seronegative for LRP4, cortactin, titin, and ryanodine receptor.

In certain embodiments, the MG patient selected for treatment is seropositive for AChR and seronegative for LRP4 and agrin.

In certain embodiments, the MG patient selected for treatment is seropositive for AChR and seronegative for LRP4, agrin, and ryanodine receptor.

In certain embodiments, the MG patient selected for treatment is seropositive for AChR and seronegative for LRP4, agrin, and titin.

In certain embodiments, the MG patient selected for treatment is seropositive for AChR and seronegative for LRP4, agrin, titin, and ryanodine receptor.

In certain embodiments, the MG patient selected for treatment is seropositive for AChR and seronegative for LRP4, agrin, and cortactin.

In certain embodiments, the MG patient selected for treatment is seropositive for AChR and seronegative for LRP4, agrin, cortactin, and ryanodine receptor.

In certain embodiments, the MG patient selected for treatment is seropositive for AChR and seronegative for LRP4, agrin, cortactin, and titin.

In certain embodiments, the MG patient selected for treatment is seropositive for AChR and seronegative for LRP4, agrin, cortactin, titin, and ryanodine receptor.

In certain embodiments, the MG patient selected for treatment is seropositive for AChR and seronegative for MuSK.

In certain embodiments, the MG patient selected for treatment is seropositive for AChR and seronegative for MuSK and ryanodine receptor.

In certain embodiments, the MG patient selected for treatment is seropositive for AChR and seronegative for MuSK and titin.

In certain embodiments, the MG patient selected for treatment is seropositive for AChR and seronegative for MuSK, titin, and ryanodine receptor.

In certain embodiments, the MG patient selected for treatment is seropositive for AChR and seronegative for MuSK and cortactin.

In certain embodiments, the MG patient selected for treatment is seropositive for AChR and seronegative for MuSK, cortactin, and ryanodine receptor.

In certain embodiments, the MG patient selected for treatment is seropositive for AChR and seronegative for MuSK, cortactin, and titin.

In certain embodiments, the MG patient selected for treatment is seropositive for AChR and seronegative for MuSK, cortactin, titin, and ryanodine receptor.

In certain embodiments, the MG patient selected for treatment is seropositive for AChR and seronegative for MuSK and agrin.

In certain embodiments, the MG patient selected for treatment is seropositive for AChR and seronegative for MuSK, agrin, and ryanodine receptor.

In certain embodiments, the MG patient selected for treatment is seropositive for AChR and seronegative for MuSK, agrin, and titin.

In certain embodiments, the MG patient selected for treatment is seropositive for AChR and seronegative for MuSK, agrin, titin, and ryanodine receptor.

In certain embodiments, the MG patient selected for treatment is seropositive for AChR and seronegative for MuSK, agrin, and cortactin.

In certain embodiments, the MG patient selected for treatment is seropositive for AChR and seronegative for MuSK, agrin, cortactin, and ryanodine receptor.

In certain embodiments, the MG patient selected for treatment is seropositive for AChR and seronegative for MuSK, agrin, cortactin, and titin.

In certain embodiments, the MG patient selected for treatment is seropositive for AChR and seronegative for MuSK, agrin, cortactin, titin, and ryanodine receptor.

In certain embodiments, the MG patient selected for treatment is seropositive for AChR and seronegative for MuSK and LRP4.

In certain embodiments, the MG patient selected for treatment is seropositive for AChR and seronegative for MuSK, LRP4, and ryanodine receptor.

In certain embodiments, the MG patient selected for treatment is seropositive for AChR and seronegative for MuSK, LRP4, and titin.

In certain embodiments, the MG patient selected for treatment is seropositive for AChR and seronegative for MuSK, LRP4, titin, and ryanodine receptor.

In certain embodiments, the MG patient selected for treatment is seropositive for AChR and seronegative for MuSK, LRP4, and cortactin.

In certain embodiments, the MG patient selected for treatment is seropositive for AChR and seronegative for MuSK, LRP4, cortactin, and ryanodine receptor.

In certain embodiments, the MG patient selected for treatment is seropositive for AChR and seronegative for MuSK, LRP4, cortactin, and titin.

In certain embodiments, the MG patient selected for treatment is seropositive for AChR and seronegative for MuSK, LRP4, cortactin, titin, and ryanodine receptor.

In certain embodiments, the MG patient selected for treatment is seropositive for AChR and seronegative for MuSK, LRP4, and agrin.

In certain embodiments, the MG patient selected for treatment is seropositive for AChR and seronegative for MuSK, LRP4, agrin, and ryanodine receptor.

In certain embodiments, the MG patient selected for treatment is seropositive for AChR and seronegative for MuSK, LRP4, agrin, and titin.

In certain embodiments, the MG patient selected for treatment is seropositive for AChR and seronegative for MuSK, LRP4, agrin, titin, and ryanodine receptor.

In certain embodiments, the MG patient selected for treatment is seropositive for AChR and seronegative for MuSK, LRP4, agrin, and cortactin.

In certain embodiments, the MG patient selected for treatment is seropositive for AChR and seronegative for MuSK, LRP4, agrin, cortactin, and ryanodine receptor.

In certain embodiments, the MG patient selected for treatment is seropositive for AChR and seronegative for MuSK, LRP4, agrin, cortactin, and titin.

In certain embodiments, the MG patient selected for treatment is seronegative for AChR, MuSK, LRP4, agrin, cortactin, titin, and ryanodine receptor.

(c) Refractory MG

In certain embodiments, the methods of the invention are useful for treatment of subjects who fail to respond adequately to or cannot tolerate multiple therapies for myasthenia gravis or continue to suffer profound muscle weakness and severe disease symptoms that limit function after treatment with existing therapies, such as intravenous immunoglobulin (IVIg), plasmapheresis, azathioprine, non-steroidal immunosuppressant drugs, steroids, cholinesterase inhibitors, immunoadsorption, and eculizumab.

In certain embodiments, the patient selected for treatment exhibits "refractory generalized myasthenia gravis". In some embodiments, refractory generalized myasthenia gravis is characterized as including subjects or patients who continue to show marked generalized weakness or bulbar signs and symptoms of myasthenia gravis while receiving current standard of care for myasthenia gravis such as cholinesterase inhibitor therapy and immunosuppressant therapy (IST) or who require chronic plasma exchange or chronic IVIg to maintain clinical stability. In other embodiments, refractory generalized myasthenia gravis is characterized as including subjects or patients who continue to show marked generalized weakness or bulbar signs and symptoms of myasthenia gravis while receiving current standard of care for myasthenia gravis such as cholinesterase inhibitor therapy and immunosuppressant therapy (IST) or who require chronic plasma exchange or chronic IVIg to maintain clinical stability. As used herein, the phrase "requires chronic plasma exchange" to maintain clinical stability refers to the use of plasma exchange therapy on a patient on a regular basis for the management of muscle weakness at least every 3 months over the last 12 months.

As used herein, the phrase "requires chronic IVIg" to maintain clinical stability refers to the use of IVIg therapy on a patient on a regular basis for the management of muscle weakness at least every 3 months over the last 12 months.

In certain embodiments, the generalized myasthenia gravis is not responsive to a standard myasthenia gravis therapy selected from the group consisting of intravenous immunoglobulin (IVIg), plasmapheresis, azathioprine, non-steroidal immunosuppressant drugs, steroids, cholinesterase inhibitors, immunoadsorption, and eculizumab.

In certain embodiments, the subject is intolerant to a standard myasthenia gravis therapy selected from the group consisting of intravenous immunoglobulin (IVIg), plasmapheresis, azathioprine, non-steroidal immunosuppressant drugs, steroids, cholinesterase inhibitors, immunoadsorption, and eculizumab.

In certain embodiments, the subject has a QMG score of at least 11 points with no more than 25% of the total points due to ocular symptoms as measured prior to administration of the isolated FcRn antagonist at day 1.

In certain embodiments, the subject has a MG-ADL score of at least 5 points with no more than 25% of the total points due to ocular symptoms as measured prior to administration of the isolated FcRn antagonist at day 1.

In certain embodiments, the subject selected for treatment (e.g., prior to first administration of the isolated FcRn antagonist) has a confirmed diagnosis of generalized MG.

In a particular embodiment, the subject has Class II-IVa disease according to the Myasthenia Gravis Foundation of America (MGFA) classification system, and has an MG-ADL score of at least 5 points with more than 50% of the score attributable to non-ocular items. In a particular embodiment, the subject has Class II-IVa disease according to the MGFA classification system, and has a QMG score of at least 11 points with no more than 25% of the total points due to ocular symptoms. In a particular embodiment, the subject has Class II-IVa disease according to the MGFA classification system, and has an MGC score of at least 10 points.

In some embodiments, the subject is an adult human with generalized myasthenia gravis whose symptoms are inadequately controlled with acetylcholinesterase inhibitors, steroids, or immunosuppressive therapies. In certain embodiments, the subject is an adult human with generalized myasthenia gravis who is anti-acetylcholinesterase receptor (AChR) antibody positive. In certain embodiments, the subject is an adult human with generalized myasthenia gravis who is anti-acetylcholinesterase receptor (AChR) antibody positive and whose symptoms are inadequately controlled with acetylcholinesterase inhibitors, steroids, or immunosuppressive therapies. In certain embodiments, the subject is an adult human with generalized myasthenia gravis who is anti-acetylcholinesterase receptor (AChR) antibody negative. In certain embodiments, the subject is an adult human with generalized myasthenia gravis who is anti-acetylcholinesterase receptor (AChR) antibody negative and whose symptoms are inadequately controlled with acetylcholinesterase inhibitors, steroids, or immunosuppressive therapies.

In certain embodiments, the subject shows marked generalized weakness or bulbar signs and symptoms of myasthenia gravis while receiving therapy for myasthenia gravis including anticholinesterase inhibitor therapy and immunosuppressant therapy (IST). In other embodiments, the subject requires chronic plasma exchange or chronic IVIg to maintain clinical stability. In certain embodiments, the subject had previously failed treatment with at least two immunosuppressive agents or failed treatment with at least one immunosuppressive agent and required chronic plasma exchange or IVIg.

In certain embodiments, the subject is positive for auto-antibodies binding to nicotinic acetylcholine receptor (anti-AChR) and shows marked generalized weakness or bulbar signs and symptoms of myasthenia gravis while receiving therapy for myasthenia gravis including anticholinesterase inhibitor therapy and immunosuppressant therapy (IST). In certain embodiments, the subject requires chronic plasma exchange or chronic IVIg to maintain clinical stability. In certain embodiments, the subject had previously failed treatment with at least two immunosuppressive agents or failed treatment with at least one immunosuppressive agent and required chronic plasma exchange or IVIg.

In certain embodiments, the subject is negative for auto-antibodies binding to nicotinic acetylcholine receptor (anti-AChR) and shows marked generalized weakness or bulbar signs and symptoms of myasthenia gravis while receiving therapy for myasthenia gravis including immunosuppressant therapy (IST). In certain embodiments, the subject is negative for auto-antibodies binding to nicotinic acetylcholine receptor (anti-AChR) and shows marked generalized weakness or bulbar signs and symptoms of myasthenia gravis while receiving therapy for myasthenia gravis including anticholinesterase inhibitor therapy and immunosuppressant therapy (IST). In certain embodiments, the subject requires chronic plasma exchange or chronic IVIg to maintain clinical stability. In certain embodiments, the subject had previously failed treatment with at least two immunosuppressive agents or failed treatment with at least one immunosuppressive agent and required chronic plasma exchange or IVIg.

(d) Comorbidities

In certain aspects, a selected MG patient may exhibit one or more symptoms of disease or disorder other than MG. In exemplary embodiments, the selected MG patient may have organ-specific or general autoimmune disorders including but not limited to thymoma, Hashimoto's disease, lupus erythematosus, and thyroiditis. Other potential comorbidities include thyroiditis, respiratory infection, osteoporosis, amyotrophic lateral sclerosis (ALS) and certain cancers such as thymomas.

V. Exemplary Embodiments

An aspect of the invention is a method of treating generalized myasthenia gravis (MG) in a subject, the method comprising administering to the subject an effective amount of an isolated FcRn antagonist, thereby treating MG in the subject, wherein:

the subject, prior to first administration of the isolated FcRn antagonist, has confirmed diagnosis generalized MG, has Class II-IVa disease according to the Myasthenia Gravis Foundation of America (MGFA) classification system, and has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

In accordance with this aspect, also provided is an isolated FcRn antagonist for use in a method of treating generalized myasthenia gravis (MG) in a subject, the method comprising administering to the subject an effective amount of the isolated FcRn antagonist, thereby treating MG in the subject, wherein:

the subject, prior to first administration of the isolated FcRn antagonist, has confirmed diagnosis generalized MG, has Class II-IVa disease according to the Myasthenia Gravis Foundation of America (MGFA) classification system, and has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

An aspect of the invention is a method of treating generalized myasthenia gravis in a subject, the method comprising administering to the subject an isolated FcRn antagonist using a phased dosing schedule with an induction phase comprising about 1-5 doses of the isolated FcRn antagonist within 1 month, followed by a maintenance phase comprising a dose of FcRn antagonist every week (q1w), every two weeks (q2w), every three weeks (q3w), or every 4 weeks (q4w) thereafter, thereby treating the generalized myasthenia gravis in the subject, wherein:

the subject, prior to first administration of the isolated FcRn antagonist, has confirmed diagnosis generalized MG, has Class II-IVa disease according to the Myasthenia Gravis Foundation of America (MGFA) classification system, and has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

In accordance with this aspect, also provided is an isolated FcRn antagonist for use in a method of treating generalized myasthenia gravis (MG) in a subject, the method comprising administering to the subject the isolated FcRn antagonist using a phased dosing schedule with an induction phase comprising about 1-5 doses of the isolated FcRn antagonist within 1 month, followed by a maintenance phase comprising a dose of FcRn antagonist every week (q1w), every two weeks (q2w), every three weeks (q3w), or every 4 weeks (q4w) thereafter, thereby treating the generalized myasthenia gravis in the subject, wherein:

the subject, prior to first administration of the isolated FcRn antagonist, has confirmed diagnosis generalized MG, has Class II-IVa disease according to the Myasthenia Gravis Foundation of America (MGFA) classification system, and has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

An aspect of the invention is a method of treating generalized myasthenia gravis in a subject, the method comprising administering to the subject an isolated FcRn antagonist using a phased dosing schedule with an induction phase comprising about 1-5 doses of the isolated FcRn antagonist within 1 month, followed by a maintenance phase comprising one or more cycles as needed based on clinical need thereafter, each cycle comprising administering to the subject about 1-5 doses of the isolated FcRn antagonist within 1 month, thereby treating the generalized myasthenia gravis in the subject, wherein:

the subject, prior to first administration of the isolated FcRn antagonist in the induction phase, has confirmed diagnosis generalized MG, has Class II-IVa disease according to the Myasthenia Gravis Foundation of America (MGFA) classification system, and has an MG-ADL score of at least 5 with more than 50% of the score attributable to non-ocular items, the subject, prior to first administration of the isolated FcRn antagonist in any cycle of the maintenance phase, has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

In accordance with this aspect, also provided is an isolated FcRn antagonist for use in a method of treating generalized myasthenia gravis (MG) in a subject, the method comprising administering to the subject the isolated FcRn antagonist using a phased dosing schedule with an induction phase comprising about 1-5 doses of the isolated FcRn antagonist within 1 month, followed by a maintenance phase comprising one or more cycles as needed based on clinical need thereafter, each cycle comprising administering to the subject about 1-5 doses of the isolated FcRn antagonist within 1 month, thereby treating the generalized myasthenia gravis in the subject, wherein:

the subject, prior to first administration of the isolated FcRn antagonist in the induction phase, has confirmed diagnosis generalized MG, has Class II-IVa disease according to the Myasthenia Gravis Foundation of America (MGFA) classification system, and has an MG-ADL score of at least 5 with more than 50% of the score attributable to non-ocular items, the subject, prior to first administration of the isolated FcRn antagonist in any cycle of the maintenance phase, has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

In certain embodiments in accordance with each of the foregoing aspects and embodiments, the subject is an adult human with generalized myasthenia gravis.

In certain embodiments in accordance with each of the foregoing aspects and embodiments, the subject is an adult human with generalized myasthenia gravis whose symptoms are inadequately controlled with acetylcholinesterase inhibitors, steroids, or immunosuppressive therapies.

In certain embodiments in accordance with each of the foregoing aspects and embodiments, the subject is an adult human with generalized myasthenia gravis who is anti-acetylcholinesterase receptor (AChR) antibody positive.

In certain embodiments in accordance with each of the foregoing aspects and embodiments, the subject is an adult human with generalized myasthenia gravis who is anti-acetylcholinesterase receptor (AChR) antibody positive and whose symptoms are inadequately controlled with acetylcholinesterase inhibitors, steroids, or immunosuppressive therapies.

For example, in certain embodiments, the invention provides a method of treating generalized myasthenia gravis (MG) in a subject, the method comprising administering to the subject an effective amount of an isolated FcRn antagonist, thereby treating MG in the subject, wherein:

the subject, prior to first administration of the isolated FcRn antagonist, has confirmed diagnosis generalized MG, has anti-AChR antibodies, has Class I I-IVa disease according to the Myasthenia Gravis Foundation of America (MGFA) classification system, and has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

As another example, in certain embodiments, the invention provides a method of treating generalized myasthenia gravis in a subject, the method comprising administering to the subject an isolated FcRn antagonist using a phased dosing schedule with an induction phase comprising about 1-5 doses of the isolated FcRn antagonist within 1 month, followed by a maintenance phase comprising a dose of FcRn antagonist every week (q1w), every two weeks (q2w), every three weeks (q3w), or every 4 weeks (q4w) thereafter, thereby treating the generalized myasthenia gravis in the subject, wherein:

the subject, prior to first administration of the isolated FcRn antagonist, has confirmed diagnosis generalized MG, has anti-AChR antibodies, has Class II-IVa disease according to the Myasthenia Gravis Foundation of America (MGFA) classification system, and has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

As yet another example, in certain embodiments, the invention provides a method of treating generalized myasthenia gravis in a subject, the method comprising administering to the subject an isolated FcRn antagonist using a phased dosing schedule with an induction phase comprising about 1-5 doses of the isolated FcRn antagonist within 1 month, followed by a maintenance phase comprising one or more cycles as needed based on clinical need thereafter, each cycle comprising administering to the subject about 1-5 doses of the isolated FcRn antagonist within 1 month, thereby treating the generalized myasthenia gravis in the subject, wherein:

the subject, prior to first administration of the isolated FcRn antagonist in the induction phase, has confirmed diagnosis generalized MG, has anti-AChR antibodies, has Class II-IVa disease according to the Myasthenia Gravis Foundation of America (MGFA) classification system, and has an MG-ADL score of at least 5 with more than 50% of the score attributable to non-ocular items, the subject, prior to first administration of the isolated FcRn antagonist in any cycle of the maintenance phase, has an MG-ADL score of at least 5 with more than 50% of the score attributable to non-ocular items, the isolated FcRn antagonist consists of a variant Fc region, wherein said variant Fc region consists of two Fc domains which form a homodimer, wherein the amino acid sequence of each of the Fc domains of the variant Fc region consists of SEQ ID NO: 2, and the isolated FcRn antagonist is administered to the subject in a dose of about 10 mg/kg.

Alternatively, in certain embodiments in accordance with each of the foregoing aspects and embodiments, the subject is an adult human with generalized myasthenia gravis who is anti-acetylcholinesterase receptor (AChR) antibody negative.

Likewise, in certain embodiments in accordance with each of the foregoing aspects and embodiments, the subject is an adult human with generalized myasthenia gravis who is anti-acetylcholinesterase receptor (AChR) antibody negative and whose symptoms are inadequately controlled with acetylcholinesterase inhibitors, steroids, or immunosuppressive therapies.

EXAMPLES

The present invention is further illustrated by the following examples, which should not be construed as further limiting. The contents of Sequence Listing, figures and all references, patents, and published patent applications cited throughout this application are expressly incorporated herein by reference.

Example 1: ARGX-113 (efgartigimod)

ARGX-113 (efgartigimod) is a human IgG1-derived Fc fragment of the za allotype (a variant Fc region) that binds with nanomolar affinity to human FcRn. The amino acid sequence of the Fc domains of ARGX-113 is SEQ ID NO: 2 (see Table 2). ARGX-113 encompasses IgG1 residues D220-K447 (EU numbering scheme) and has been modified with the so-called ABDEG™ technology (ABDEG™=antibody that enhances IgG degradation) (Vaccaro C et al., Nat. Biotechnol. 23(10): 1283-8 (2005)) to increase its affinity for FcRn at both physiological and acidic pH. The increased affinity for FcRn of ARGX-113 at both acidic and physiological pH results in a constitutive blockage of FcRn-mediated recycling of IgGs.

Given the essential role of the FcRn receptor in IgG homeostasis, inhibiting this FcRn function, as achieved by ARGX-113, leads to rapid degradation of endogenous IgGs, including autoantibodies in IgG-driven autoimmune diseases such as myasthenia gravis.

This concept has been validated in various murine disease models together with pharmacokinetic/pharmacodynamic (PK/PD) studies in cynomolgus monkeys, either by using ARGX-113 or a full-length mAb analogue (HEL-ABDEG™). Challa D K et al., MAbs 5(5): 655-9(2013); Patel D A et al., J. Immunol. 187(2): 1015-22 (2011).

In murine in vivo disease models for rheumatoid arthritis and multiple sclerosis a clear improvement in disease score was observed after treatment with an ABDEG™-equipped molecule. This improvement was accompanied with systemic lowering of autoantibody levels.

Pharmacokinetic and PD studies in cynomolgus monkey confirmed the antibody-clearing properties of ARGX-113 in a relevant animal model. A single infusion of ARGX-113 resulted in a decrease of endogenous IgG up to 55% without altering serum albumin concentrations as well as IgM or IgA levels. This PD effect was proven to be more potent than IVIg, which is considered a standard of care therapy in MG, both in rapidity of onset and in depth of the PD effect. Repeated dosing could improve the PD effect up to a maximum IgG reduction of 75%.

These pre-clinical data validated the further development of ARGX-113 for assessing its therapeutic potential in IgG-driven autoimmune indications, including myasthenia gravis.

Example 2: Phase II Study of ARGX-113 in Patients with Generalized Myasthenia Gravis A randomized, double-blind, placebo-controlled multicenter Phase II study was undertaken to evaluate the safety, efficacy, and pharmacokinetics of ARGX-113 (efgartigimod) for the treatment of autoimmune MG with generalized muscle weakness. The study design is depicted in FIG. 1.

Objectives of the study included evaluation of the safety and tolerability of ARGX-113; evaluation of the clinical efficacy of ARGX-113 using MG-ADL, QMG, MGC, and MGQoL15r scores; evaluation of the PK of ARGX-113; assessment of the PD markers (e.g., total IgG, IgG subtypes, and anti-AChR antibodies); and evaluation of immunogenicity of ARGX-113. Study-eligible patients had a confirmed diagnosis of autoimmune MG with generalized muscle weakness meeting the clinical criteria for diagnosis of MG as defined by the Myasthenia Gravis Foundation of America (MGFA) Clinical Classification Class II, III, or IVa. Confirmation of the diagnosis was supported by a positive serologic test for anti-AChR antibodies before screening and at least 1 of the following 3 tests:
  (i) History of abnormal neuromuscular transmission test demonstrated by single-fiber electromyography or repetitive nerve stimulation;
  (ii) History of positive edrophonium chloride test; or
  (iii) Demonstrated improvement in MG signs on oral cholinesterase inhibitors as assessed by the treating physician.

Study eligibility also required a total score of 5 on the MG-ADL at screening and baseline with more than 50% of this score attributed to non-ocular items.

Twenty-four study-eligible patients were randomized at a 1:1 ratio to receive ARGX-113 (10 mg/kg) or placebo in 4 infusions administered one week apart over three weeks, in addition to Standard of Care (SoC). The total dose per ARGX-113 infusion was capped at 1200 mg for patients with body weight 120 kg. SoC for a patient was the stable dose and administration of their MG treatment prior to enrollment. Permitted SoC for MG treatment under this study included azathioprine (AZA), other non-steroidal immunosuppressant drugs (NSIDs: e.g., methotrexate, cyclosporine, tacrolimus, mycophenolate mofetil, and cyclophosphamide), steroids, as well as cholinesterase inhibitors. Patients were required to be on a stable dose of their MG treatment prior to randomization.

ARGX-113 (provided as a sterile, colorless, clear concentrate solution for intravenous administration in a formulation of 25 mM sodium phosphate, 100 mM sodium chloride, and 150 mM L-arginine hydrochloride, (pH 6.7) with 0.02% (w/v) polysorbate 80) or matching placebo was administered via intravenous (IV) infusion (250 mL total volume) over a period of 2 hours on Days 1 (Visit 1), 8±1 (Visit 3), 15±1 (Visit 5), and 22±1 (Visit 7). At the end of the 3-week treatment period, the patients entered an 8-week follow-up period.

Treatment Period

On all dosing days (Visits 1, 3, 5 and 7), the following assessments and steps were made:
  MGQoL15r, MG-ADL, QMG, and MGC prior to administration of ARGX-113;
  Blood sampling for assessment of PD markers (total IgG, IgG subtypes, and anti-AChR antibodies);
  Blood sampling pre-dose for PK assessments;
  Administration of ARGX-113 (10 mg/kg) or placebo; and
  Blood sampling post-dose for PK assessments.

Follow-Up Period

The follow-up period included assessments at Visit 8 to Visit 16.

The following assessments were made at Visits 9, 10, 11, 12, 14, and 16:
  MGQoL15r, MG-ADL, QMG, and MGC; and
  Blood sampling for PK (not on Visits 14 and 16) and PD (total IgG, IgG subtypes, and anti-AChR antibodies).

In addition, the following assessments were made at Visits 13 and 15:
  Blood sampling for PD assessments (total IgG, IgG subtypes, and anti-AChR antibodies).

Data Analysis

Statistical analyses were performed using statistical analysis system (SAS®), (SAS Institute, Cary, NC, USA) version 9.2 or higher.

Analysis of Clinical Parameters

Summaries and listings of data for vital signs, hematology, clinical chemistry and urinalysis laboratory tests, ECGs, and physical examination findings were collected. Appropriate data was summarized for the observed value at each scheduled assessment and for the corresponding change from baseline.

Analyses of data derived from scales (MG-ADL, QMG, MGC, and MGQoL15r) were based on full analysis set. Actual score, change from baseline, and maximum reduction from baseline were evaluated.

Analyses of the change from baseline in efficacy rating scales was performed using a mixed-model repeated measures (MMRM) analysis from Visit 1 to Visit 16. The models included the fixed treatment, baseline score and patient as a random effect. Appropriate covariance structure was used. For each visit day, ARGX-113 was compared with placebo and model-based Least Squares Means for the treatment effects, 95% CIs and p-values were calculated for within and between treatment comparisons.

Analysis of Pharmacokinetic Parameters

Pharmacokinetic analyses were performed based on the PK population (randomized patients who had at least one plasma concentration value available for ARGX-113). Plasma concentrations of ARGX-113 at each sampling time point were analyzed by the following summary statistics: arithmetic mean calculated using untransformed data, SD calculated using untransformed data, minimum, median, maximum, number of observations, and number of observations lower limit of quantification (LLOQ).

Geometric mean plasma concentrations against protocol time were shown by patient in both linear and log scales, respectively.

The following summary statistics were assessed for all the PK parameters except for tmax: Gmean, GCV, arithmetic mean calculated using untransformed data, SD calculated using untransformed data, minimum, median, maximum, and number of observations.

The following summary statistics were assessed for the PK parameters tmax: number of observations, median, minimum, and maximum.

Analysis of Pharmacodynamic Parameters

Continuous PD parameters were summarized with descriptive statistics including geometric mean. Pharmacodynamic parameters included total IgG, IgG subtypes, and anti-AChR antibodies.

Anti-Drug Antibodies (ADA) Analyses

Frequency and percentage of ADA response were assessed. ADA response data was summarized as proportions along with their 95% CIs using exact test separately for each treatment.

Results

Results from this study were highly favorable and demonstrated the utility of ARGX-113 in the treatment of generalized myasthenia gravis.

Patients in the ARGX-113 treatment group and the placebo group had baseline disease characteristics shown in Table 4.

TABLE 4

Phase II study patient baseline characteristics

|  | Placebo (N = 12) | ARGX-113 (N = 12) |
|---|---|---|
| Baseline QMG score (mean ± SD) | 11.8 ± 5.4 | 14.5 ± 6.3 |
| Baseline MG-ADL score (mean ± SD) | 8.0 ± 2.2 | 8.0 ± 3.0 |

TABLE 4-continued

Phase II study patient baseline characteristics

|  | Placebo (N = 12) | ARGX-113 (N = 12) |
|---|---|---|
| Baseline MGC score (mean ± SD) | 14.5 ± 4.5 | 16.7 ± 8.7 |
| Baseline MGQoL score (mean ± SD) | 14.5 ± 6.1 | 19.7 ± 5.7 |
| Acetylcholinesterase Inhibitor N (%) | 11 (91.7%) | 12 (100.0%) |
| Corticosteroids N (%) | 5 (41.7%) | 8 (66.7%) |
| Immunosuppressants N (%) | 2 (16.7%) | 9 (75.0%) |

Figure 7A:
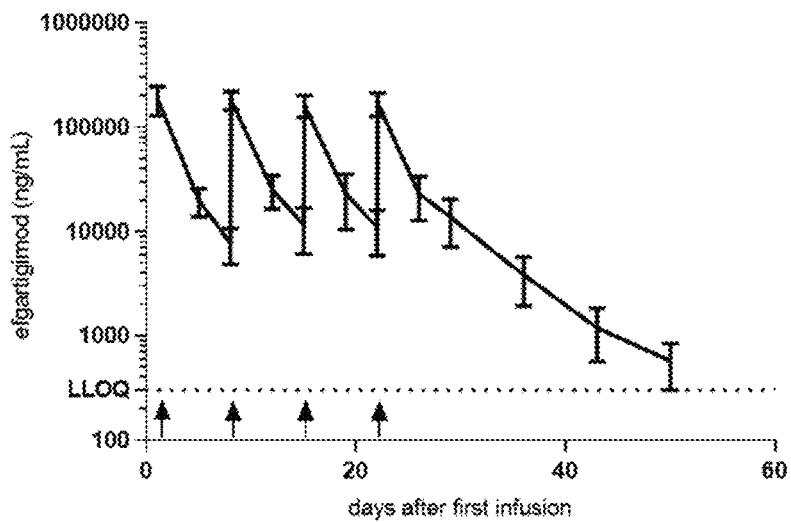
FIG. 7A is a graph depicting serum levels of ARGX-113 in humans.

The PK parameters were very similar in all efgartigimod-treated patients, without accumulation (geometric mean $R_{ac}$=0.9360) following each infusion, and with PK parameters after the last infusion similar to the one after the first (FIG. 7A). Serum concentrations of efgartigimod were still quantifiable in all patients at 21 to 28 days after the last infusion. The $C_{max}$ at Visit 1 was 187±58 pg/mL at a $t_{max}$ of 2.37±0.165 hours, and the $t_{1/2,\lambda z}$ was 117.4 hours (i.e., 4.89 days)±18.84 hours (all values are mean±SD).

Figure 7B:
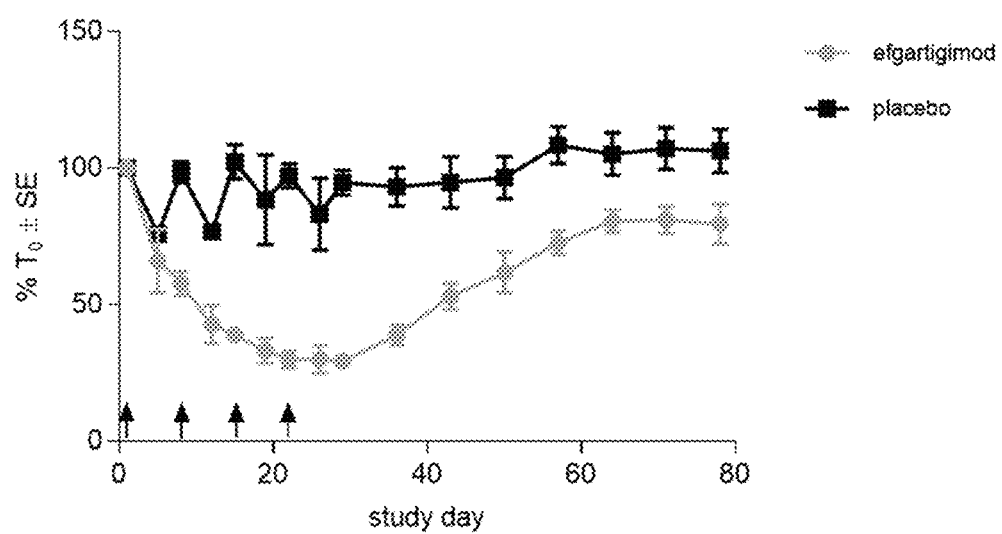
FIG. 7B is a graph depicting total IgG serum levels after ARGX-113 and placebo treatment over 11 weeks.
Figure 8:
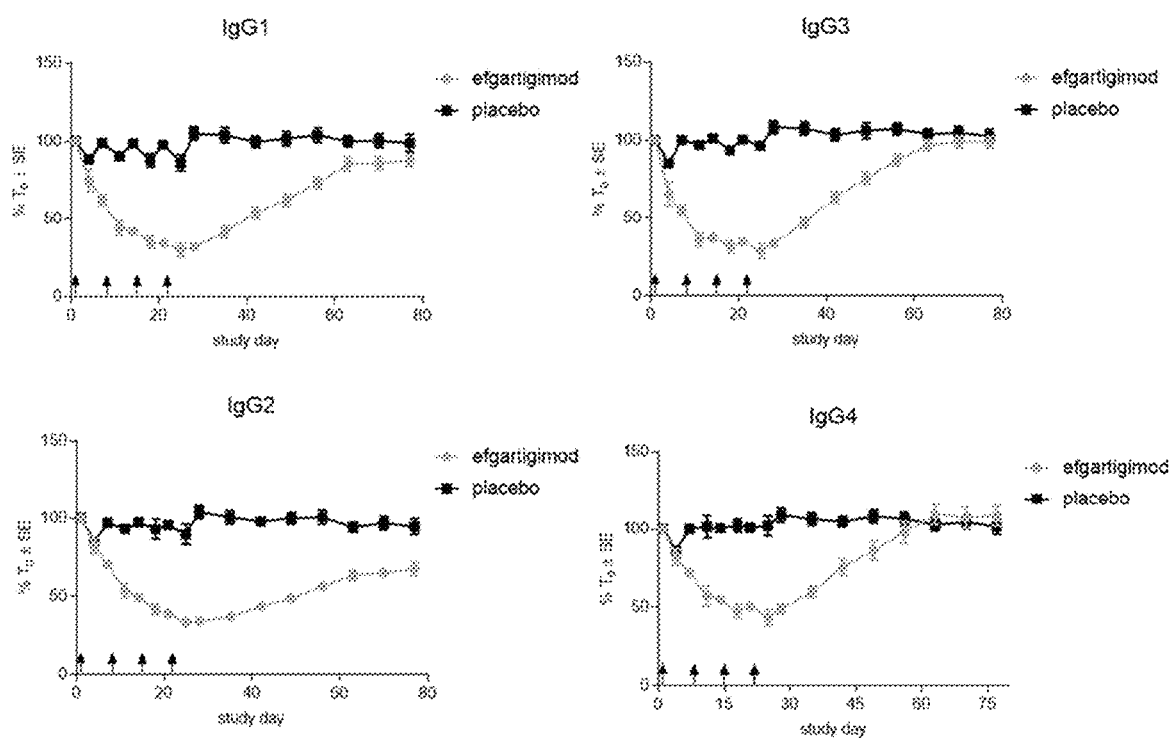
FIG. 8 is four graphs depicting IgG subtype serum levels after ARGX-113 and placebo treatment over 11 weeks.

A total serum IgG reduction of approximately 40% compared to baseline was achieved in the first week (following the first dose) (FIG. 7B). This reduction further increased to a mean maximum of 70.7% after subsequent doses. IgG levels remained reduced by 50% or more for approximately 3 weeks. At 8 weeks following the last infusion, we observed a 20% reduction of total IgG levels. This rapid, substantial, and sustained reduction was seen across all IgG subtypes (FIG. 8).

Figure 7C:
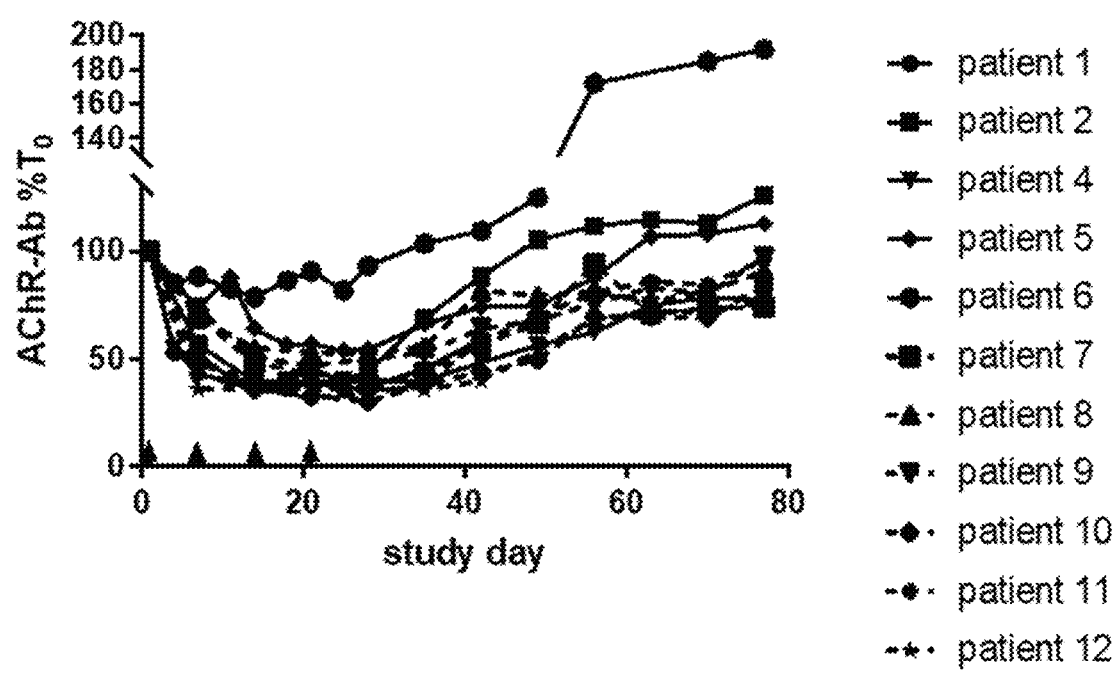
FIG. 7C is a graph depicting individual serum anti-AChR autoantibody profiles relative to baseline levels.

The reductions of serum IgG levels mirrored the observed potent reduction of anti-AChR autoantibodies, which are typically of the IgG1 and IgG3 subclasses (FIG. 7C). As early as 15 days after the first infusion, an approximately maximal reduction of 40% to 70% of anti-AChR autoantibody level was reached in all patients except one, and this reduced level was sustained until Day 29 after the first infusion after which after which autoantibody levels gradually increased to approach baseline levels approximately 8 weeks after the last dose.

Positive post-dosing anti-drug antibody (ADA) titers were detected in four out of 12 patients receiving ARGX-113 and in three out of 12 patients receiving placebo. In line with the results obtained in the Phase 1 healthy volunteer trial, the majority of ADA signals in active-treated patients were just above the detection limit of the assay and were typically only found once or twice during the course of the trial. In one active-treated patient, positive post-dose ADA titers were detected as of two weeks after the last infusion, and these titers may have the tendency to slightly increase over the course of the trial. Positive post-dose ADA titers had no apparent effect on efgartigimod pharmacokinetics or pharmacodynamics.

Primary endpoint analysis demonstrated ARGX-113 to be safe and well tolerated in all patients, with most adverse events (AEs) characterized as mild and deemed unrelated to the study drug. No serious or severe AEs were reported. The observed safety and tolerability profile is consistent with the Phase 1 healthy volunteer study.

Figure 9:
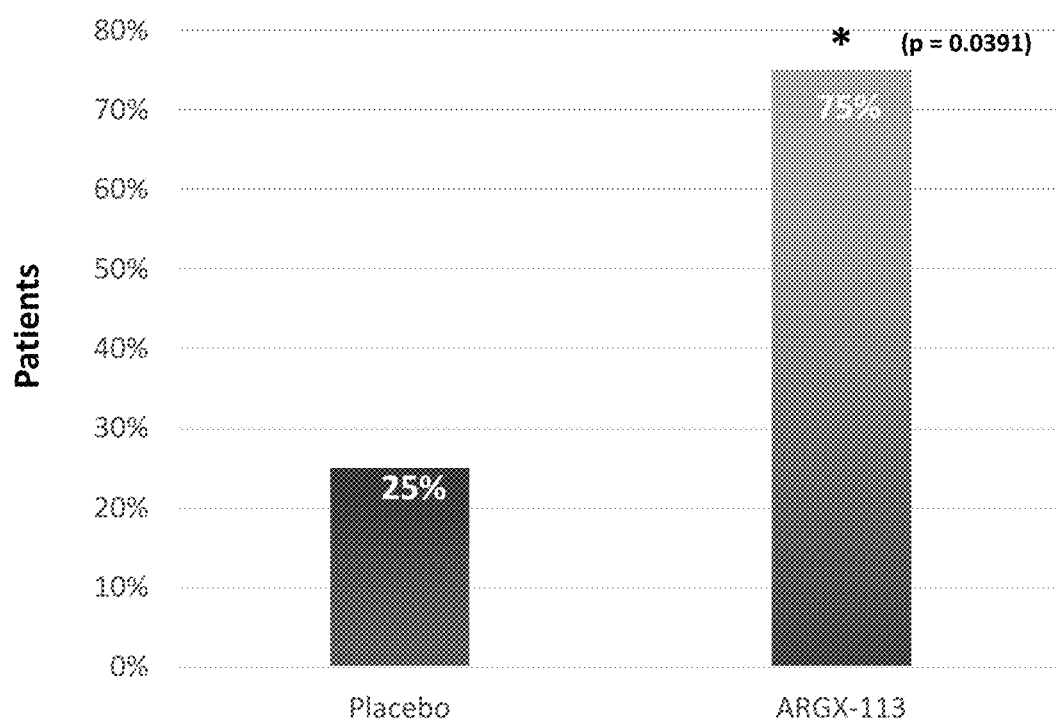
FIG. 9 is a bar graph depicting improvement of at least 2 points in MG-ADL for a period of at least 6 weeks in patients treated with placebo or ARGX-113 as described herein.

The secondary endpoint measures relating to efficacy showed ARGX-113 treatment resulted in a strong clinical improvement over placebo during the entire duration of the study as measured by all four predefined clinical efficacy scales. Specifically:

As shown in FIG. 9, 75% of patients treated with ARGX-113 had a clinically meaningful and statistically significant improvement in MG-ADL scores (at least a 2-point reduction from baseline) for a period of at least 6 consecutive weeks versus 25% of patients on placebo (p=0.0391).

Figure 10:
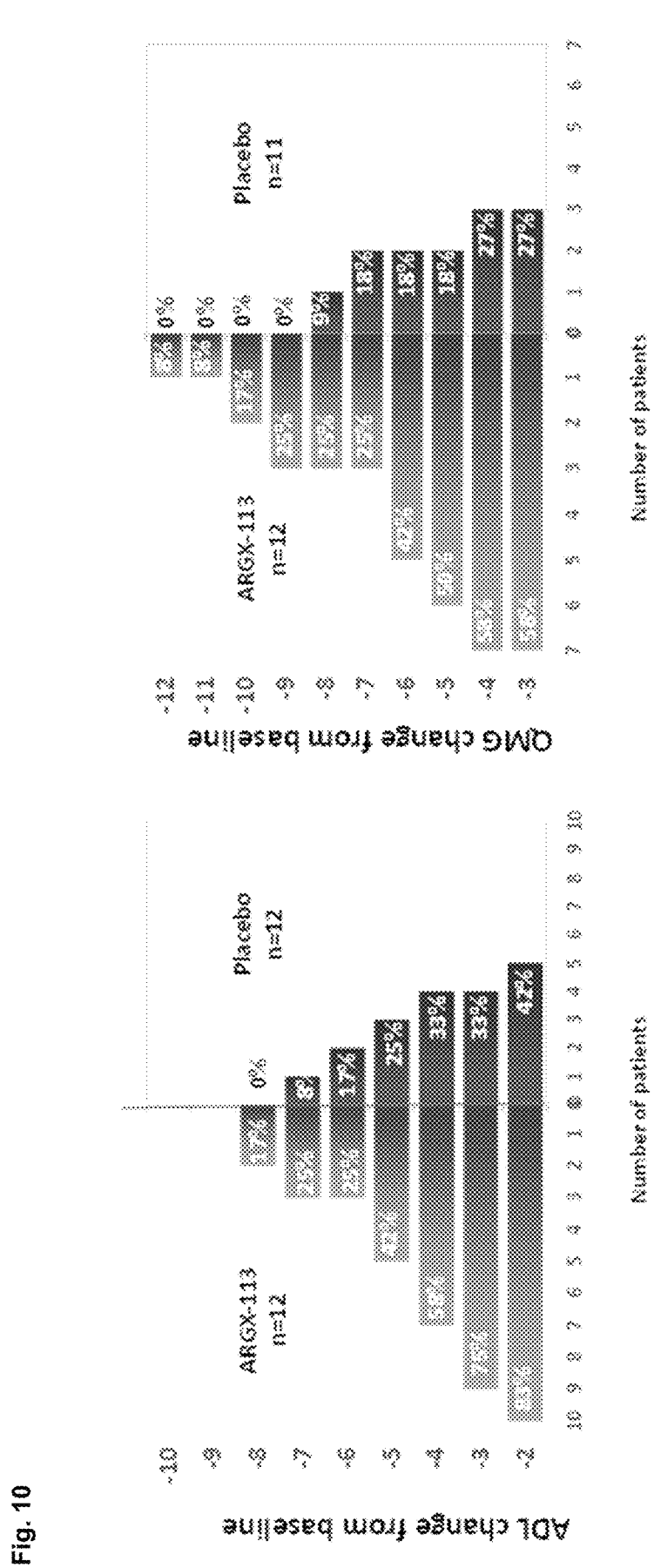
FIG. 10 is a pair of graphs depicting changes from baseline in MG-ADL (ADL) and QMG scores at day 29 in patients treated with placebo or ARGX-113 as described herein.

Clinical benefit in the ARGX-113 treatment group maximized as of 1 week after the administration of the last dose, achieving statistical significance over the placebo group (p=0.0356) on the MG-ADL score. As shown in FIG. 10, increasing differentiation was observed between the ARGX-113 treatment group versus placebo with increasing MG-ADL thresholds.

Patients in the treatment arm showed rapid onset of disease improvement, with clear separation from placebo 1 week after the first infusion.

All patients in the treatment arm showed a rapid and deep reduction of their total IgG levels and disease improvement was found to correlate with reduction in pathogenic IgG (anti-AChR) levels.

Figure 11A:
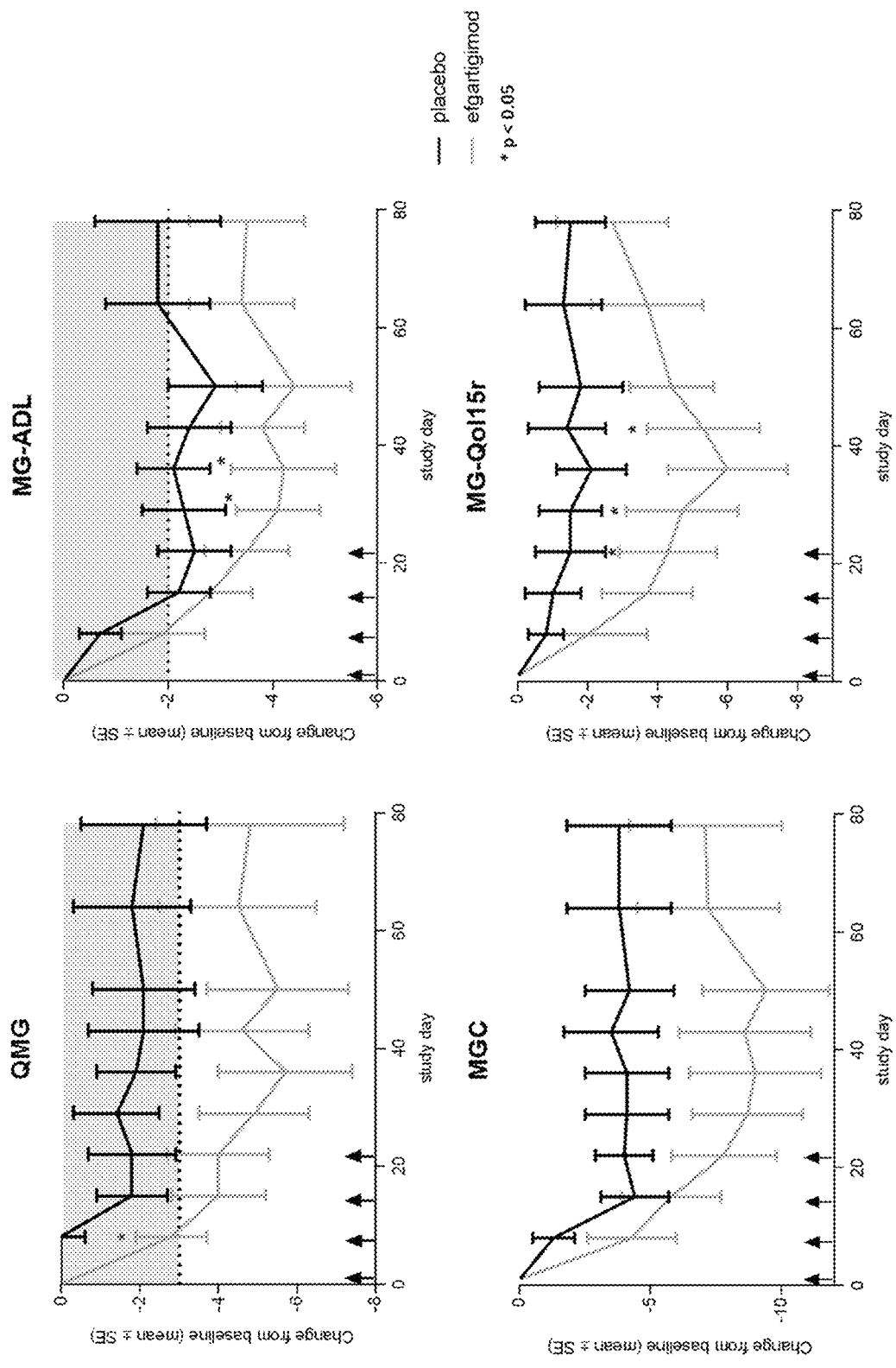
FIG. 11A is four graphs depicting changes from baseline in QMG, MG-ADL, MGC, and MG-QoL15r over 11 weeks. Values are mean±standard error. Negative score is indicative of clinical improvement. Dotted line delineates clinical significance zone. Arrows on the X-axis indicate time points of treatment administration; *stars indicate statistically significant change from baseline ($p \leq 1.05$).

The clinical improvement as assessed by different efficacy scales (MG-ADL, QMG, and MGC) and a quality of life scale (MG-QoL15r) showed an evolution in time which was consistent with the observed total serum levels of IgG and of anti-AChR autoantibody (FIG. 11A). For all four scales, initial effects were noted as early as 7 days after the first infusion. Maximal reduction in scores occurred as of 1 to 2 weeks after the last administration, which coincides with the maximal PD effect. This reduction reached a maximum mean of 5.7 points (39% reduction from baseline) on the QMG scale, 4.4 points (55% reduction) on the MG-ADL scale, 9.4 points (56% reduction) on the MGC scale, and 6 points (31% reduction) on the MG-QoL15r; the respective placebo values were −2.1 points (18%; QMG), −2.9 points (36%; MG-ADL), −4.4 points (30%; MGC), and −2.1 points (14%; MG-QoL15r). Despite the small size of the patient cohort treated with efgartigimod, statistical significance was reached for a 3-point change in QMG score after the first infusion (difference estimated with MMRM=−2.38; 95%Cl [−4.63, −0.13] and p=0.0394), and statistical significance was reached at 29 and 36 days for MG-ADL coinciding with maximal IgG reduction (differences and p-values respectively −2.05 [−3.95, −0.15], p=0.0356; and −2.08 [−4.12, −0.04], p=0.0459). The MG-QoL15r score changed in a similar way (statistical significance at Day 22, 29, and 43; differences and p-values respectively −3.72 [−7.41, −0.02], p=0.0489; −3.87 [−7.69, −0.05], p=0.0475; and −4.38 [−8.56, −0.20], p=0.0407).

In contrast to the IgG and autoantibody levels that returned to or close to baseline by the end of the study, the clinical scores gave a sustainable improvement throughout the entire study. At 78 days after first infusion, the QMG, MG-ADL, and MGC scores still were reduced by 4.8, 3.5, 7.1 points, respectively. The MG-QoL15r score almost returned to baseline at this time point.

Compared to the rather short efgartigimod terminal half-life (4.89 days), the clinical effects were long lasting (throughout the follow-up period, i.e., 8 weeks after the last efgartigimod administration). The clinical benefit of efgartigimod initially correlated with the IgG reduction but extended even after the IgG level had returned close to baseline. The duration of clinical improvement in the efgartigimod treatment group compared favorably to the relatively short-lived effect of plasmapheresis (2-4 weeks). In both approaches IgG and autoantibody return to basal levels in a comparable way, but the duration of the clinical effect is clearly different. Plasmapheresis removes the bulk of serum antibodies at one timepoint. In between sessions of plasmapheresis IgG from the tissue redistributes and serum IgG increases again, resulting in a zig-zag pattern of autoantibody and serum IgG levels. Efgartigimod showed continuous lowering of IgG levels consistent with a prolonged action after administration. Of course, efgartigimod is an antibody-like drug that has a prolonged mode of action, explaining the difference with plasmapheresis.

Figure 11B:
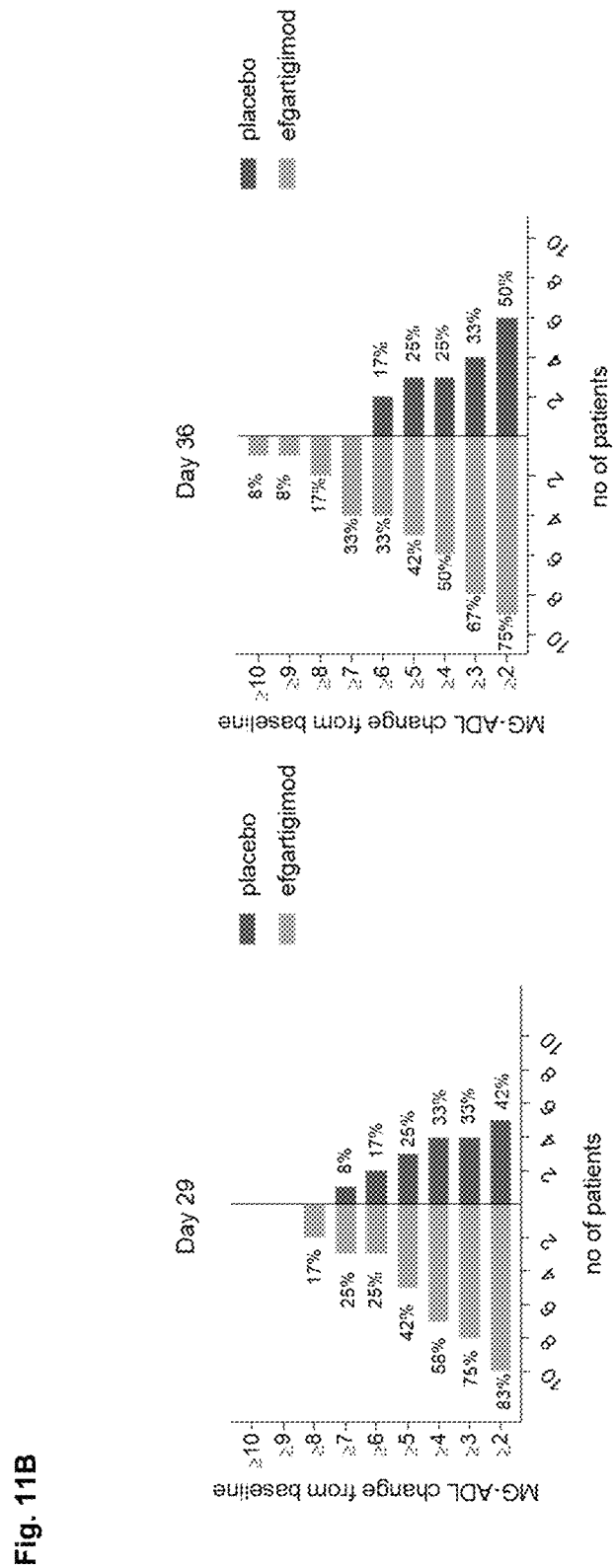
FIG. 11B is a pair of bar graphs depicting minimum point improvements on the outcome measures of the MG-ADL scale on day 29 and 36, i.e. the study days where the pharmacodynamic effect was maximal; percentages of patients showing a clinical improvement of at least the specified value are indicated next to the bars. SE=standard error.

Responder analyses were performed at Day 29 and 36 when IgG reduction was maximal (FIG. 11B). At any point-reduction level, a greater percentage of efgartigimod-treated patients had a clinical improvement compared to placebo. Some patients treated with efgartigimod experienced a point improvement of and as high as 11 on the MG-ADL scale and of ≥9 and as high as 18 in QMG score, while none of the placebo-treated patients reached these levels.

In summary, these results demonstrate a rapid and sustained benefit in disease score after treatment with ARGX-113, supporting further development of ARGX-113 as a potential new option to fill the current treatment gap for MG patients.

Example 3: Phase III Study of ARGX-113 in Patients with Exacerbation of Generalized Myasthenia Gravis A randomized, double blind, placebo controlled, multi-center Phase III study is undertaken to evaluate the efficacy, safety, quality of life and impact on normal daily activities of ARGX-113 in patients with exacerbation of generalized myasthenia gravis.

Objectives of the study include evaluation of the efficacy of ARGX-113 on disease severity as assessed by change in QMG score from baseline to day 29; evaluation of the efficacy of ARGX-113 on disease severity as assessed by change in QMG score from baseline at day 8, 15 and 22; evaluation of the efficacy of ARGX-113 on disease severity as assessed by change in MG-ADL and MGC from baseline at day 8, 15, 22 and 29; evaluation of the efficacy of ARGX-113 on disease severity as assessed by the percent change from baseline in QMG, MG-ADL and MGC at day 8, 15, 22 and 29; evaluation of the effect of ARGX-113 on total IgG level; evaluation of the effect of ARGX-113 on AChR autoantibodies in AChR-positive patients; evaluation of the safety of AGRX-113; and evaluation of the effect of ARGX-113 on quality of life as assessed by specific and generic quality of life instrument.

Study-eligible patients have a confirmed diagnosis of MG with generalized muscle weakness meeting the clinical criteria for diagnosis of MG as defined by the Myasthenia Gravis Foundation of America (MGFA) Clinical Classification Class II, III, IVa, or IVb with an objective worsening of their symptoms (exacerbation) and which, in the opinion of the investigator, may be eligible for rescue therapy with IVIg or PLEX or a temporary use or dose increase of steroids or immunosuppressants. Confirmation of the diagnosis is documented and supported by:
  (i) History of abnormal neuromuscular transmission demonstrated by single-fiber electromyography or repetitive nerve stimulation; or
  (ii) History of positive edrophonium chloride test; or
  (iii) Demonstrated improvement in MG signs on oral cholinesterase inhibitors as assessed by the treating physician.
Study eligibility also requires QMG value of 11 points with no more than 25% points due to ocular symptoms.

X study-eligible patients are randomized at a 1:1 ratio to receive ARGX-113 (10 mg/kg) or placebo in 4 infusions administered one week apart over three weeks, in addition to Standard of Care (SoC). SoC for a patient is the stable dose and administration of their MG treatment prior to enrollment. Permitted SoC for MG treatment under this study includes azathioprine (AZA), other non-steroidal immunosuppressant drugs (NSIDs: e.g., methotrexate, cyclosporine, tacrolimus, mycophenolate mofetil, and cyclophosphamide), steroids, as well as cholinesterase inhibitors.

ARGX-113 (provided as a sterile, colorless, clear concentrate solution for intravenous administration in a formulation of 25 mM sodium phosphate, 100 mM sodium chloride, and 150 mM L-arginine hydrochloride, (pH 6.7) with 0.02% (w/v) polysorbate 80) or matching placebo is administered via intravenous (IV) infusion (250 mL total volume) over a period of 2 hours on Days 1, 8, 15, and 22. At the end of the 3-week treatment period, the patients enter a 4-week follow-up period during which they are treated with SoC only.

Assessment during the follow-up period is performed at Days 29, 36, and 50, and will include efficacy and safety parameters.

Study procedures, including endpoint assessments, will be performed according to the Schedule of Assessments. Cholinesterase inhibitors must be held for at least 10 hours prior to performing MG efficacy scales.

The efficacy analysis is performed on full analysis set (FAS) and on per protocol (PP) populations.

Figure 12:
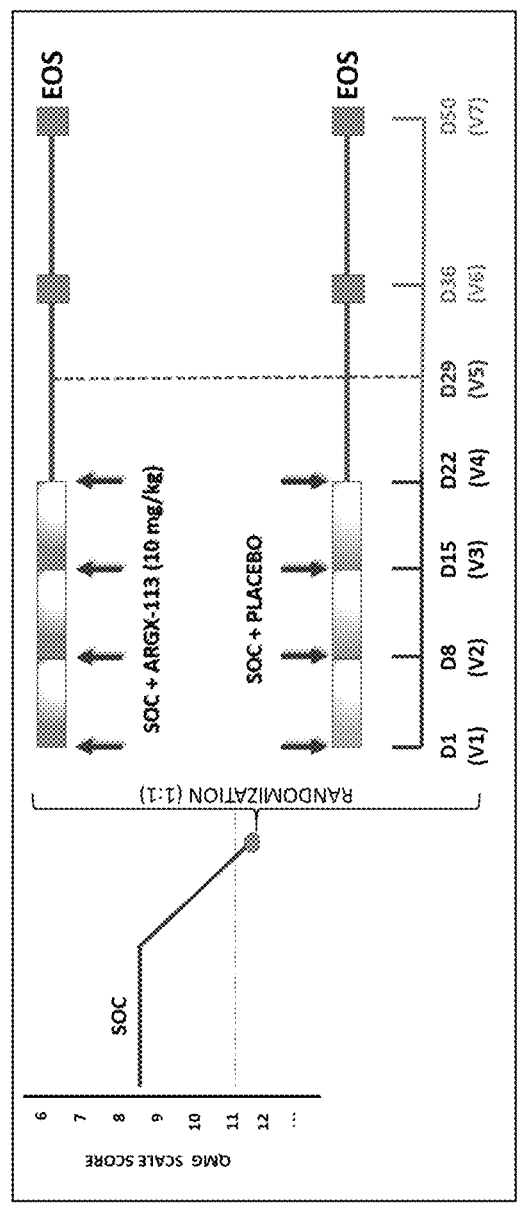
FIG. 12 depicts a schematic of the study design for the ARGX-113 Phase III clinical trial protocol. SOC, standard of care; EOS, end of study.

A schematic of study design is presented in FIG. 12.

Study assessments include QMG score change from baseline (defined as the score immediately prior to first dose at Visit 1) to day 29; QMG score change from baseline to day 8, 15 and 22; MG-ADL and MGC score change from baseline to day 8, 15, 22 and 29; percent change from baseline in QMG, MG-ADL and MGC at day 8, 15, 22 and 29; percentage of patients that have a decrease of at least 4 points of the QMG score at day 8, 15, 22 and 29; percentage decrease (compared to baseline) of total IgG level at day 8, 15, 22 and 29; percentage decrease (compared to baseline) of AChR autoantibodies in AChR-positive patients at day 8, 15, 22 and 29; and MGQoL15 and EQ-5D score and percent change from baseline to day 8, 15, 22 and 29.

Data Analysis

The primary endpoint, QMG score change from baseline between groups at day 29, is analyzed by means of mixed-model repeated measures (MMRM) analysis.

The other continuous variables (MG-ADL, MGC, IgG, AChR, MGQoL15, and EQ-5D, either in absolute values or percent decrease/change forms) are analyzed using the same approach as for QMG.

Alpha adjustment is performed on the primary efficacy endpoint (QMG score change from baseline to day 29) and on the following secondary endpoints: clinically significant improvement in QMG score at day 29 (i.e., assessment of percentage of patients having a decrease of at least 4 points of the QMG score at day 29), in combination with early onset assessment of QMG score change from baseline. The Hochberg procedure is used for alpha adjustment.

Binary variables with repeated measurements along the study, such as the decrease of at least 4 points of the QMG, are analyzed using a generalized linear mixed model based on the based on the logit link function.

The main efficacy analysis is based on all randomized patients with baseline evaluation following the Intent-to-Treat (ITT), and the primary endpoint is also assessed using the Per Protocol (PP) subset.

Example 4: Phase III Study of ARGX-113 in Patients with Generalized Myasthenia Gravis A 26-week, randomized, double blind, placebo controlled, multicenter Phase III study (ADAPT Study) was undertaken to evaluate the efficacy, safety, and tolerability of ARGX-113 in patients with generalized myasthenia gravis.

Patients at least 18 years of age with Myasthenia Gravis Foundation of America (MGFA) class II, III, IVa, and IVb disease, MG-ADL score 5, and on a stable dose of standard of care (SoC) treatment were eligible for enrollment, provided they did not have any one or more of severe infection, total IgG level <6 g/L, and documented lack of clinical response to PLEX (plasma exchange). Patients eligible for enrollment included those who were seropositive and those who were seronegative for anti-AChR antibodies.

Stable SoC requirements prior to screening for entry into the study included (i) non-steroidal immunosuppressants—on treatment for at least 6 months and no dose changes within the last 3 months; (ii) steroids—on treatment for at least 3 months and no dose changes within the last month; and/or (iii) acetylcholinesterase inhibitors—on treatment with a stable dose with no dose escalation within the last 2 weeks.

Figure 13:
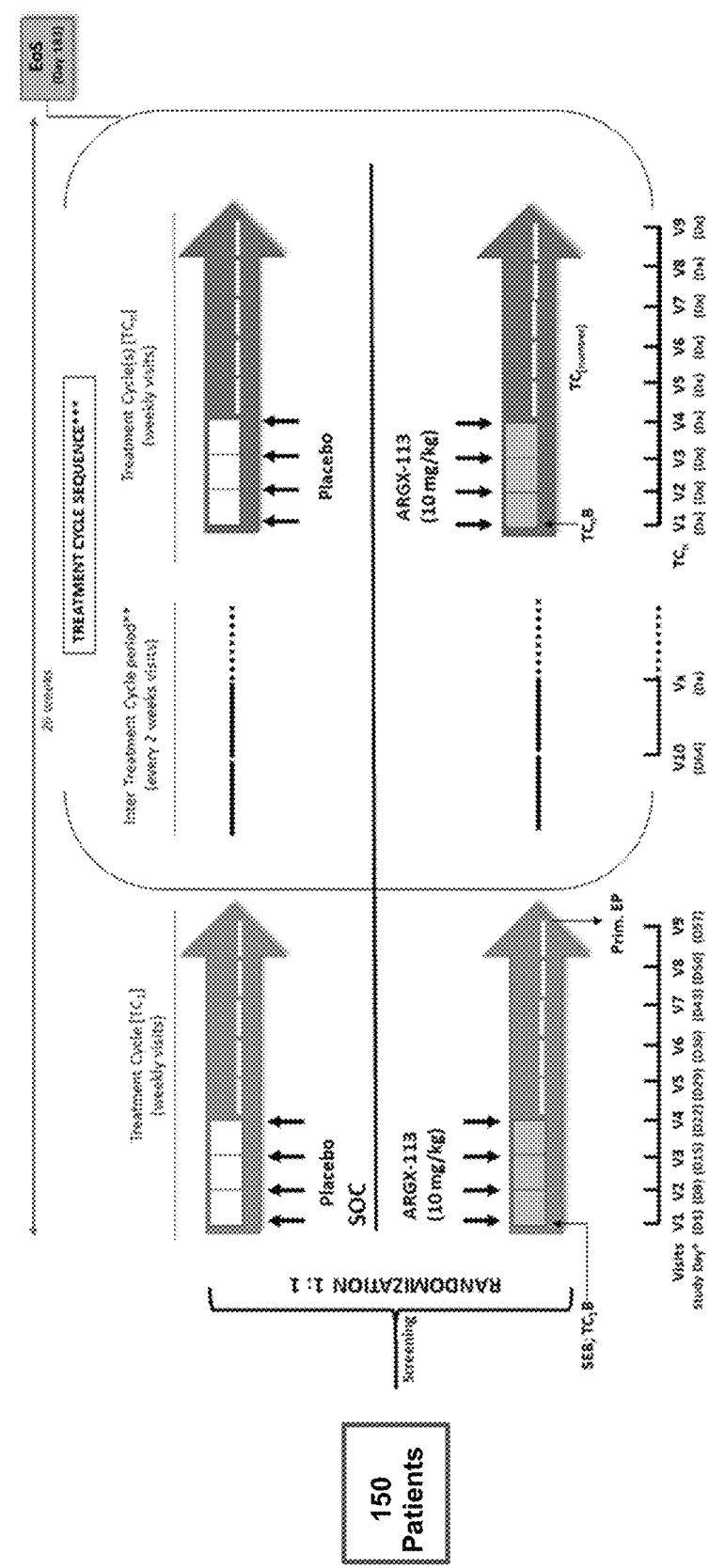
FIG. 13 depicts a schematic of the study design for the ARGX-113 Phase III clinical trial protocol in the ADAPT Study (Example 4). EoS, end of study; Prim. EP, primary endpoint; SEB, study entry baseline; SOC, standard of care; $TC_n$, treatment cycle$_{(number)}$; $TC_nB$, treatment cycle$_{(number)}$ baseline.

FIG. 13 depicts the study design. 150 study-eligible patients were screened and randomized 1:1 into groups receiving either ARGX-113 or placebo control. All patients remained on SoC treatment during the study. Patients in each study group then embarked upon an 8-week long initial treatment cycle comprised of, first, a three-week long infusion period, and then a 5-week long follow-up period. Upon completion of the 8-week long initial treatment cycle, each patient then embarked upon one or more treatment cycle sequences, each such treatment cycle sequence comprised of, first, an inter-treatment period of variable length depending on protocol-defined clinical need, and then an 8-week long treatment cycle, the latter again comprised of, first, a three-week long infusion period, and then a 5-week long follow-up period.

Patients in each study group had a study entry baseline and an initial treatment cycle (TC,) lasting 8 weeks, during which time each patient had 9 weekly patient visits (V1-V9), where ARGX-113 (10 mg/kg i.v. infusion) or placebo (i.v. infusion) was administered at each of V1 (Day 1), V2 (Day 8), V3 (Day 15), and V4 (Day 22), followed by weekly visits over 5 weeks (V5-V9) without further ARGX-113 or placebo until reaching a primary endpoint at day 57, after which patients entered a second phase of the study during which patients received one or more individual patient-tailored subsequent treatment cycle sequences. In each subsequent treatment cycle sequence, patients received neither ARGX-113 nor placebo during an initial inter-treatment cycle period with every-other-week visits, followed by (if needed, based on individual patient's protocol-defined clinical need—see below) a treatment cycle ($TC_n$) with weekly visits. As in the initial treatment cycle described above, the treatment cycle in each treatment cycle sequence consisted of establishing a treatment cycle baseline ($TCB_n$) at the outset of 9 weekly patient visits (V1-V9) over 8 weeks, where ARGX-113 (10 mg/kg i.v. infusion) or placebo (i.v. infusion) was administered at each of V1 (Day x), V2 (Day x+7), V3 (Day x+14), and V4 (Day x+21), followed by weekly visits over 5 weeks (V5-V9) without further ARGX-113 or placebo. Thus, inter-treatment cycles were tailored to each subject based on protocol-defined clinical need. Each $TC_n$ was then followed by another treatment cycle sequence. The treatment cycle sequence could be repeated as many times as needed during the timeframe of the study, provided that the last treatment cycle did not start later than Day 126 of the study. In this way, the final treatment cycle would be a full 8 weeks. End of study was reached at Day 183 for each patient.

Each patient was eligible to receive a new treatment cycle with ARGX-113 or placebo when all of the following criteria were met:

(1) The patient had completed the previous treatment cycle (8 weeks);

(2) The patient had a total MG-ADL score of 5;

(3) The treatment cycle could start at the latest on Day 126 and could be completed within the timeframe of the trial (26 weeks); and (4) In case the patient was an MG-ADL responder at the previous treatment cycle, the patient had lost the response.

An MG-ADL responder was defined as a patient having a reduction of 2 points on MG-ADL score compared to treatment cycle baseline, for at least 4 consecutive weeks, where the first of these reductions occurred at the latest 1 week after the last infusion. Thus, an MG-ADL responder could be identified only during the 5-week follow-up period of a treatment cycle, even though an MG-ADL responder could first meet the score reduction requirement during either the 3-week treatment period or the 5-week follow-up period of the treatment cycle.

A QMG responder was defined as a patient having a reduction of 3 points on QMG score compared to treatment cycle baseline, for at least 4 consecutive weeks, where the first of these reductions occurred at the latest 1 week after the last infusion. Thus, a QMG responder could be identified only during the 5-week follow-up period of a treatment cycle, even though a QMG responder could first meet the score reduction requirement during either the 3-week treatment period or the 5-week follow-up period of the treatment cycle.

Loss of response was defined as no longer showing a decrease of 2 points on the total MG-ADL score compared to the corresponding treatment cycle baseline.

Protocol-defined clinical deterioration was defined as a patient experiencing new or worsening respiratory/bulbar symptoms or at least a 2-point increase of individual non-ocular MG-ADL items.

Rescue therapy was permitted for patients experiencing protocol-defined MG clinical deterioration, provided the treating physician believed the patient's health was in jeopardy. Permitted rescue therapies were PLEX, IVIg, immunoadsorption, and/or increased steroid dose. Patients receiving rescue therapy were discontinued from further participation in the study.

The primary endpoint for this study was percentage of MG-ADL responders in patient population seropositive for anti-AChR antibody. Secondary endpoints for this study were (i) percentage of QMG responders in patient population seropositive for anti-AChR antibody; (ii) percentage of MG-ADL responders in overall patient population (seropositive and seronegative for anti-AChR antibody); and (iii) duration of treatment response.

Example 5: Rollover Open-Label Phase III Study of ARGX-113 in Patients with Generalized Myasthenia Gravis A follow-on 26-week, single-arm, open-label, multicenter Phase III study (ADAPT+Study) was undertaken to evaluate further the safety and tolerability of ARGX-113 in patients with generalized myasthenia gravis.

Figure 14:
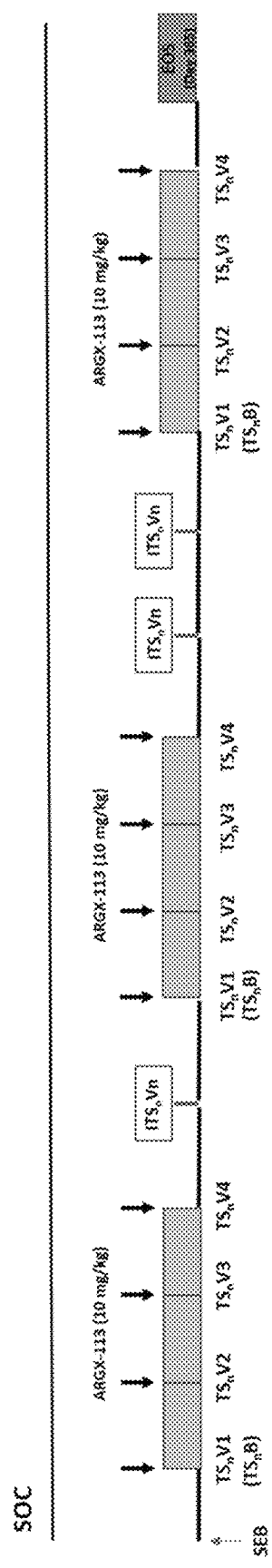
FIG. 14 depicts a schematic of the study design for the ARGX-113 Phase III clinical trial protocol in the ADAPT+ Study (Example 5). EOS, end of study; $ITS_nV$, inter-treatment sequence$_{(number)}$ visit; SEB, study entry baseline; SOC, standard of care; $TS_nB$, treatment sequence$_{(number)}$ baseline; $TS_nV$, treatment sequence$_{(number)}$ visit.

FIG. 14 depicts the study design. Study-eligible patients were selected (rolled over) from ARGX-113 and placebo groups in the ADAPT Study. All patients remained on SoC treatment during the study, subject to adjustment as specified below.

Patients from the ADAPT Study described in Example 4 were eligible to roll over into the ADAPT+Study when (i) they reached the end of study visit at week 26 of that Study, or if they required retreatment and the 8-week cycle could not be completed by week 26 (i.e., after Day 126). Patients who received rescue therapy or were otherwise discontinued early from study or treatment in the ADAPT Study were excluded from this study. Taken together with the ADAPT Study, patients in this follow-on study were followed for approximately 1 year where they received multiple treatment cycles, each treatment cycle comprising a 3-week treatment period, during which patients received 4 doses of ARGX-113 10 mg/kg i.v. infusion, followed by a 5-week follow-up period and/or an inter-treatment cycle period, with times between treatment periods varying from patient to patient based upon individual protocol-defined clinical need.

Each patient was eligible to receive a new treatment cycle with ARGX-113 when all of the following criteria were satisfied:

(1) The patient had a total MG-ADL score of 5 points with more than 50% of the score due to non-ocular symptoms;

(2) The patient showed a reduction of total MG-ADL score of <2 points compared to the score at the last treatment cycle baseline in the ADAPT Study (Example 4) for the first treatment period in this study, or compared to the last treatment period baseline for all subsequent treatment periods ($TP_n$) in this (ADAPT+) study; and (3) The patient had completed the previous treatment period.

The SoC was required to remain stable until the end of the first treatment period (4 weekly doses over 3 weeks), and it was required to remain stable during each treatment period. However, reductions in SoC were allowed between treatment periods in accordance with medical practice.

Rescue therapy was permitted and defined as in the ADAPT Study (Example 4).

We claim:

1. A method of treating generalized myasthenia gravis (gMG) in a subject in need thereof comprising intravenously administering to the subject an FcRn antagonist consisting of a variant Fc region, wherein the variant Fc region consists of two Fc domains which form a homodimer, wherein the amino acid sequence of each of the Fc domains consists of SEQ ID NO: 2 or SEQ ID NO: 3, wherein the FcRn antagonist is administered using a phased dosing schedule comprising an induction phase followed by a maintenance phase, wherein the induction phase lasts for 7, 8, 9, or 10 weeks and consists of 4 doses of 10 mg/kg of the FcRn antagonist, wherein each dose of the FcRn antagonist is administered once weekly during weeks 1, 2, 3, and 4 of the induction phase;

wherein the maintenance phase comprises one or more cycles as needed based on clinical need thereafter, wherein each cycle consists of 4 doses of 10 mg/kg of the FcRn antagonist within 1 month, wherein each dose of each cycle is administered once weekly; and wherein the subject is positive for auto-antibodies binding to nicotinic acetylcholine receptor (anti-AChR).

2. The method of claim 1, wherein the amino acid sequence of each of the Fc domains consists of SEQ ID NO: 2.

3. The method of claim 1, wherein the FcRn antagonist is efgartigimod.

4. The method of claim 1, wherein the amino acid sequence of each of the Fc domains consists of SEQ ID NO: 3.

5. The method of claim 1, wherein the subject, prior to first administration of the FcRn antagonist, has confirmed diagnosis gMG, has Class II-IVa disease according to the Myasthenia Gravis Foundation of America (MGFA) classification system, and has an MG-ADL score of at least 5 with more than 50% of the score attributable to non-ocular items.

6. The method of claim 1, wherein the gMG is not responsive to a standard myasthenia gravis therapy selected from the group consisting of intravenous immunoglobulin (IVIg), plasmapheresis, azathioprine, non-steroidal immunosuppressant drugs, steroids, cholinesterase inhibitors, immunoadsorption, and eculizumab.

7. The method of claim 1, wherein administration of the FcRn antagonist improves one or more therapeutic evaluation scores in the subject selected from the group consisting of Quantitative Myasthenia Gravis (QMG) score and Myasthenia Gravis activities of daily living (MG-ADL) score.

8. The method of claim 7, wherein the QMG score is decreased by at least 3 points at day 8, 15, 22, 29, or 36 compared to a baseline QMG score as measured prior to administration of the FcRn antagonist at day 1.

9. The method of claim 7, wherein the MG-ADL score is decreased by at least 2 points at day 8, 15, 22, 29, or 36 compared to a baseline MG-ADL score as measured prior to administration of the FcRn antagonist at day 1.

10. The method of claim 1, wherein the subject exhibits a clinically meaningful improvement in MG-ADL score.

11. The method of claim 10, wherein the subject exhibits a clinically meaningful improvement in MG-ADL score no later than 1 week after the last of the 4 weekly administrations of the induction phase or no later than 1 week after the last of the 4 weekly administrations of a cycle during the maintenance phase.

12. The method of claim 10, wherein the clinically meaningful improvement in MG-ADL score is a 2-point or greater reduction in score.

13. The method of claim 1, wherein the subject exhibits an improvement of at least 2 points in MG-ADL score at day 29 or 36 compared to a baseline MG-ADL score as measured prior to administration of the FcRn antagonist at day 1.

14. The method of claim 1, wherein the subject exhibits an improvement of at least 2 points in MG-ADL score for a period of at least 6 weeks.

15. The method of claim 1, wherein the subject exhibits an MG-ADL response, wherein an MG-ADL response is a reduction of >2 points in MG-ADL score compared to treatment cycle baseline, for at least 4 consecutive weeks, wherein the first of the reductions occurs at the latest 1 week after the last administration of the treatment cycle, wherein the treatment cycle comprises 4 weekly administrations of the FcRn antagonist.

16. The method of claim 1, wherein the subject exhibits a QMG response, wherein a QMG response is a reduction of >3 points in QMG score compared to treatment cycle baseline, for at least 4 consecutive weeks, wherein the first of the reductions occurs at the latest 1 week after the last administration of the treatment cycle, wherein the treatment cycle comprises 4 weekly administrations of the FcRn antagonist.

17. The method of claim 1, wherein the doses of the induction phase are administered on days 1, 8, 15, and 22.

18. The method of claim 1, wherein the induction phase lasts for 7 weeks.

19. The method of claim 1, wherein the induction phase lasts for 8 weeks.

20. The method of claim 1, wherein each cycle of the maintenance phase lasts for 8 weeks, and wherein the 4 doses of each cycle of the maintenance phase are administered during weeks 1, 2, 3, and 4 of each 8-week cycle.

21. The method of claim 1, wherein the clinical need is determined based on a total MG-ADL score of ≥5 in the subject or a total MG-ADL score of ≥5 with more than 50% of the score due to non-ocular symptoms in the subject.

* * * * *

SEQUENCE LISTING

```
<160> NUMBER OF SEQ ID NOS: 57

<210> SEQ ID NO 1
<211> LENGTH: 221
<212> TYPE: PRT
<213> ORGANISM: Artificial
<220> FEATURE:
<223> OTHER INFORMATION: Synthetic peptide

<400> SEQUENCE: 1

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Tyr Ile Thr Arg Glu Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu Lys
        195                 200                 205

Phe His Tyr Thr Gln Lys Ser Leu Ser Leu Ser Pro Gly
    210                 215                 220
```

```
<210> SEQ ID NO 2
<211> LENGTH: 227
<212> TYPE: PRT
<213> ORGANISM: Artificial
<220> FEATURE:
<223> OTHER INFORMATION: Synthetic peptide

<400> SEQUENCE: 2

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu Lys Phe His Tyr Thr Gln Lys Ser Leu Ser Leu Ser
    210                 215                 220

Pro Gly Lys
225

<210> SEQ ID NO 3
<211> LENGTH: 226
<212> TYPE: PRT
<213> ORGANISM: Artificial
<220> FEATURE:
<223> OTHER INFORMATION: Synthetic peptide

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

-continued

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu Lys Phe His Tyr Thr Gln Lys Ser Leu Ser Leu Ser
    210                 215                 220

Pro Gly
225

<210> SEQ ID NO 4
<211> LENGTH: 5
<212> TYPE: PRT
<213> ORGANISM: Artificial
<220> FEATURE:
<223> OTHER INFORMATION: Synthetic peptide

<400> SEQUENCE: 4

Glu Tyr Ala Met Gly
1               5

<210> SEQ ID NO 5
<211> LENGTH: 5
<212> TYPE: PRT
<213> ORGANISM: Artificial
<220> FEATURE:
<223> OTHER INFORMATION: Synthetic peptide

<400> SEQUENCE: 5

Val Tyr Ala Met Gly
1               5

<210> SEQ ID NO 6
<211> LENGTH: 17
<212> TYPE: PRT
<213> ORGANISM: Artificial
<220> FEATURE:
<223> OTHER INFORMATION: Synthetic peptide

<400> SEQUENCE: 6

Ser Ile Gly Ser Ser Gly Gly Gln Thr Lys Tyr Ala Asp Ser Val Lys
1               5                   10                  15

Gly

<210> SEQ ID NO 7
<211> LENGTH: 17
<212> TYPE: PRT
<213> ORGANISM: Artificial
<220> FEATURE:
<223> OTHER INFORMATION: Synthetic peptide
```

<400> SEQUENCE: 7

Ser Ile Gly Ser Ser Gly Gly Pro Thr Lys Tyr Ala Asp Ser Val Lys
1               5                   10                  15

Gly

<210> SEQ ID NO 8
<211> LENGTH: 7
<212> TYPE: PRT
<213> ORGANISM: Artificial
<220> FEATURE:
<223> OTHER INFORMATION: Synthetic peptide

<400> SEQUENCE: 8

Leu Ser Thr Gly Glu Leu Tyr
1               5

<210> SEQ ID NO 9
<211> LENGTH: 7
<212> TYPE: PRT
<213> ORGANISM: Artificial
<220> FEATURE:
<223> OTHER INFORMATION: Synthetic peptide

<400> SEQUENCE: 9

Leu Ser Ile Arg Glu Leu Val
1               5

<210> SEQ ID NO 10
<211> LENGTH: 7
<212> TYPE: PRT
<213> ORGANISM: Artificial
<220> FEATURE:
<223> OTHER INFORMATION: Synthetic peptide

<400> SEQUENCE: 10

Leu Ser Ile Val Asp Ser Tyr
1               5

<210> SEQ ID NO 11
<211> LENGTH: 7
<212> TYPE: PRT
<213> ORGANISM: Artificial
<220> FEATURE:
<223> OTHER INFORMATION: Synthetic peptide

<400> SEQUENCE: 11

Leu Ser Leu Gly Asp Ser Tyr
1               5

<210> SEQ ID NO 12
<211> LENGTH: 7
<212> TYPE: PRT
<213> ORGANISM: Artificial
<220> FEATURE:
<223> OTHER INFORMATION: Synthetic peptide

<400> SEQUENCE: 12

Leu Ala Ile Gly Asp Ser Tyr
1               5

<210> SEQ ID NO 13
<211> LENGTH: 14
<212> TYPE: PRT
<213> ORGANISM: Artificial
<220> FEATURE:

```
<223> OTHER INFORMATION: Synthetic peptide

<400> SEQUENCE: 13

Thr Gly Thr Gly Ser Asp Val Gly Ser Tyr Asn Leu Val Ser
1               5                   10

<210> SEQ ID NO 14
<211> LENGTH: 7
<212> TYPE: PRT
<213> ORGANISM: Artificial
<220> FEATURE:
<223> OTHER INFORMATION: Synthetic peptide

<400> SEQUENCE: 14

Gly Asp Ser Gln Arg Pro Ser
1               5

<210> SEQ ID NO 15
<211> LENGTH: 10
<212> TYPE: PRT
<213> ORGANISM: Artificial
<220> FEATURE:
<223> OTHER INFORMATION: Synthetic peptide

<400> SEQUENCE: 15

Cys Ser Tyr Ala Gly Ser Gly Ile Tyr Val
1               5                   10

<210> SEQ ID NO 16
<211> LENGTH: 7
<212> TYPE: PRT
<213> ORGANISM: Artificial
<220> FEATURE:
<223> OTHER INFORMATION: Synthetic peptide

<400> SEQUENCE: 16

Gly Asp Ser Glu Arg Pro Ser
1               5

<210> SEQ ID NO 17
<211> LENGTH: 10
<212> TYPE: PRT
<213> ORGANISM: Artificial
<220> FEATURE:
<223> OTHER INFORMATION: Synthetic peptide

<400> SEQUENCE: 17

Ser Ser Tyr Ala Gly Ser Gly Ile Tyr Val
1               5                   10

<210> SEQ ID NO 18
<211> LENGTH: 5
<212> TYPE: PRT
<213> ORGANISM: Artificial
<220> FEATURE:
<223> OTHER INFORMATION: Synthetic peptide

<400> SEQUENCE: 18

Thr Tyr Ala Met Gly
1               5

<210> SEQ ID NO 19
<211> LENGTH: 5
<212> TYPE: PRT
<213> ORGANISM: Artificial
<220> FEATURE:
<223> OTHER INFORMATION: Synthetic peptide
```

<400> SEQUENCE: 19

Asp Tyr Ala Met Gly
1               5

<210> SEQ ID NO 20
<211> LENGTH: 5
<212> TYPE: PRT
<213> ORGANISM: Artificial
<220> FEATURE:
<223> OTHER INFORMATION: Synthetic peptide

<400> SEQUENCE: 20

Asn Tyr Ala Met Gly
1               5

<210> SEQ ID NO 21
<211> LENGTH: 14
<212> TYPE: PRT
<213> ORGANISM: Artificial
<220> FEATURE:
<223> OTHER INFORMATION: Synthetic peptide

<400> SEQUENCE: 21

Ser Ile Gly Ser Ser Gly Ala Gln Thr Arg Tyr Ala Asp Ser
1               5                   10

<210> SEQ ID NO 22
<211> LENGTH: 14
<212> TYPE: PRT
<213> ORGANISM: Artificial
<220> FEATURE:
<223> OTHER INFORMATION: Synthetic peptide

<400> SEQUENCE: 22

Ser Ile Gly Ala Ser Gly Ser Gln Thr Arg Tyr Ala Asp Ser
1               5                   10

<210> SEQ ID NO 23
<211> LENGTH: 14
<212> TYPE: PRT
<213> ORGANISM: Artificial
<220> FEATURE:
<223> OTHER INFORMATION: Synthetic peptide

<400> SEQUENCE: 23

Ser Ile Gly Ala Ser Gly Ala Gln Thr Arg Tyr Ala Asp Ser
1               5                   10

<210> SEQ ID NO 24
<211> LENGTH: 14
<212> TYPE: PRT
<213> ORGANISM: Artificial
<220> FEATURE:
<223> OTHER INFORMATION: Synthetic peptide

<400> SEQUENCE: 24

Ser Ile Gly Ala Ser Gly Gly Gln Thr Arg Tyr Ala Asp Ser
1               5                   10

<210> SEQ ID NO 25
<211> LENGTH: 7
<212> TYPE: PRT
<213> ORGANISM: Artificial
<220> FEATURE:
<223> OTHER INFORMATION: Synthetic peptide

```
<400> SEQUENCE: 25

Leu Ala Ile Gly Asp Ser Tyr
1               5

<210> SEQ ID NO 26
<211> LENGTH: 10
<212> TYPE: PRT
<213> ORGANISM: Artificial
<220> FEATURE:
<223> OTHER INFORMATION: Synthetic peptide

<400> SEQUENCE: 26

Gly Phe Thr Phe Ser Asn Tyr Gly Met Val
1               5                   10

<210> SEQ ID NO 27
<211> LENGTH: 17
<212> TYPE: PRT
<213> ORGANISM: Artificial
<220> FEATURE:
<223> OTHER INFORMATION: Synthetic peptide

<400> SEQUENCE: 27

Tyr Ile Asp Ser Asp Gly Asp Asn Thr Tyr Tyr Arg Asp Ser Val Lys
1               5                   10                  15

Gly

<210> SEQ ID NO 28
<211> LENGTH: 8
<212> TYPE: PRT
<213> ORGANISM: Artificial
<220> FEATURE:
<223> OTHER INFORMATION: Synthetic peptide

<400> SEQUENCE: 28

Gly Ile Val Arg Pro Phe Leu Tyr
1               5

<210> SEQ ID NO 29
<211> LENGTH: 16
<212> TYPE: PRT
<213> ORGANISM: Artificial
<220> FEATURE:
<223> OTHER INFORMATION: Synthetic peptide

<400> SEQUENCE: 29

Lys Ser Ser Gln Ser Leu Val Gly Ala Ser Gly Lys Thr Tyr Leu Tyr
1               5                   10                  15

<210> SEQ ID NO 30
<211> LENGTH: 7
<212> TYPE: PRT
<213> ORGANISM: Artificial
<220> FEATURE:
<223> OTHER INFORMATION: Synthetic peptide

<400> SEQUENCE: 30

Leu Val Ser Thr Leu Asp Ser
1               5

<210> SEQ ID NO 31
<211> LENGTH: 9
<212> TYPE: PRT
<213> ORGANISM: Artificial
<220> FEATURE:
<223> OTHER INFORMATION: Synthetic peptide
```

```
<400> SEQUENCE: 31

Leu Gln Gly Thr His Phe Pro His Thr
1               5

<210> SEQ ID NO 32
<211> LENGTH: 5
<212> TYPE: PRT
<213> ORGANISM: Artificial
<220> FEATURE:
<223> OTHER INFORMATION: Synthetic peptide

<400> SEQUENCE: 32

Ser Tyr Gly Ile Ser
1               5

<210> SEQ ID NO 33
<211> LENGTH: 17
<212> TYPE: PRT
<213> ORGANISM: Artificial
<220> FEATURE:
<223> OTHER INFORMATION: Synthetic peptide

<400> SEQUENCE: 33

Glu Ile Tyr Pro Arg Ser Gly Asn Thr Tyr Tyr Asn Glu Lys Phe Lys
1               5                   10                  15

Gly

<210> SEQ ID NO 34
<211> LENGTH: 9
<212> TYPE: PRT
<213> ORGANISM: Artificial
<220> FEATURE:
<223> OTHER INFORMATION: Synthetic peptide

<400> SEQUENCE: 34

Ser Thr Thr Val Ser Pro Ala Asp Phe
1               5

<210> SEQ ID NO 35
<211> LENGTH: 9
<212> TYPE: PRT
<213> ORGANISM: Artificial
<220> FEATURE:
<223> OTHER INFORMATION: Synthetic peptide

<400> SEQUENCE: 35

Ser Thr Thr Val Ser Pro Pro Pro Ile
1               5

<210> SEQ ID NO 36
<211> LENGTH: 9
<212> TYPE: PRT
<213> ORGANISM: Artificial
<220> FEATURE:
<223> OTHER INFORMATION: Synthetic peptide

<400> SEQUENCE: 36

Ser Thr Thr Val Ser Pro Pro Ala His
1               5

<210> SEQ ID NO 37
<211> LENGTH: 9
<212> TYPE: PRT
<213> ORGANISM: Artificial
<220> FEATURE:
```

```
<223> OTHER INFORMATION: Synthetic peptide

<400> SEQUENCE: 37

Ser Thr Thr Val Ala Pro Pro Arg Leu
1               5

<210> SEQ ID NO 38
<211> LENGTH: 9
<212> TYPE: PRT
<213> ORGANISM: Artificial
<220> FEATURE:
<223> OTHER INFORMATION: Peptide

<400> SEQUENCE: 38

Ser Thr Thr Val His Pro Asp Arg Asn
1               5

<210> SEQ ID NO 39
<211> LENGTH: 9
<212> TYPE: PRT
<213> ORGANISM: Artificial
<220> FEATURE:
<223> OTHER INFORMATION: Synthetic peptide

<400> SEQUENCE: 39

Ser Thr Thr Val Ser Pro Pro Ala Leu
1               5

<210> SEQ ID NO 40
<211> LENGTH: 9
<212> TYPE: PRT
<213> ORGANISM: Artificial
<220> FEATURE:
<223> OTHER INFORMATION: Synthetic peptide

<400> SEQUENCE: 40

Ser Thr Thr Val His Pro Asp His Asn
1               5

<210> SEQ ID NO 41
<211> LENGTH: 9
<212> TYPE: PRT
<213> ORGANISM: Artificial
<220> FEATURE:
<223> OTHER INFORMATION: Synthetic peptide

<400> SEQUENCE: 41

Ser Thr Thr Val Ser Pro Pro His Leu
1               5

<210> SEQ ID NO 42
<211> LENGTH: 9
<212> TYPE: PRT
<213> ORGANISM: Artificial
<220> FEATURE:
<223> OTHER INFORMATION: Synthetic peptide

<400> SEQUENCE: 42

Ser Thr Thr Val Ala Pro Pro Pro Leu
1               5

<210> SEQ ID NO 43
<211> LENGTH: 9
<212> TYPE: PRT
<213> ORGANISM: Artificial
<220> FEATURE:
<223> OTHER INFORMATION: Synthetic peptide
```

```
<400> SEQUENCE: 43

Ser Thr Thr Val Ala Pro Pro Gly His
1               5

<210> SEQ ID NO 44
<211> LENGTH: 9
<212> TYPE: PRT
<213> ORGANISM: Artificial
<220> FEATURE:
<223> OTHER INFORMATION: Synthetic peptide

<400> SEQUENCE: 44

Ser Thr Thr Val Ser Pro Pro Arg Val
1               5

<210> SEQ ID NO 45
<211> LENGTH: 9
<212> TYPE: PRT
<213> ORGANISM: Artificial
<220> FEATURE:
<223> OTHER INFORMATION: Synthetic peptide

<400> SEQUENCE: 45

Ser Thr Thr Val Ser Pro Pro Pro Leu
1               5

<210> SEQ ID NO 46
<211> LENGTH: 9
<212> TYPE: PRT
<213> ORGANISM: Artificial
<220> FEATURE:
<223> OTHER INFORMATION: Synthetic peptide

<400> SEQUENCE: 46

Ser Thr Thr Val Ala Pro Pro Ala His
1               5

<210> SEQ ID NO 47
<211> LENGTH: 9
<212> TYPE: PRT
<213> ORGANISM: Artificial
<220> FEATURE:
<223> OTHER INFORMATION: Synthetic peptide

<400> SEQUENCE: 47

Ser Thr Thr Val Arg Pro Pro Gly Ile
1               5

<210> SEQ ID NO 48
<211> LENGTH: 9
<212> TYPE: PRT
<213> ORGANISM: Artificial
<220> FEATURE:
<223> OTHER INFORMATION: Synthetic peptide

<400> SEQUENCE: 48

Ser Thr Thr Val Ser Ala Pro Gly Val
1               5

<210> SEQ ID NO 49
<211> LENGTH: 9
<212> TYPE: PRT
<213> ORGANISM: Artificial
<220> FEATURE:
<223> OTHER INFORMATION: Synthetic peptide
<220> FEATURE:
```

```
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 49

Ser Thr Thr Val Xaa Pro Pro Xaa Xaa
1               5

<210> SEQ ID NO 50
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (5)..(9)
<223> OTHER INFORMATION: Xaa can be any naturally occurring amino acid

<400> SEQUENCE: 50

Ser Thr Thr Val Xaa Xaa Xaa Xaa Xaa
1               5

<210> SEQ ID NO 51
<211> LENGTH: 11
<212> TYPE: PRT
<213> ORGANISM: Artificial
<220> FEATURE:
<223> OTHER INFORMATION: Synthetic peptide

<400> SEQUENCE: 51

Lys Ala Ser Asp His Ile Asn Asn Trp Leu Ala
1               5                   10

<210> SEQ ID NO 52
<211> LENGTH: 7
<212> TYPE: PRT
<213> ORGANISM: Artificial
<220> FEATURE:
<223> OTHER INFORMATION: Synthetic peptide

<400> SEQUENCE: 52

Gly Ala Thr Ser Leu Glu Thr
1               5

<210> SEQ ID NO 53
<211> LENGTH: 9
<212> TYPE: PRT
<213> ORGANISM: Artificial
<220> FEATURE:
<223> OTHER INFORMATION: Synthetic peptide

<400> SEQUENCE: 53

Gln Gln Tyr Trp Ser Thr Pro Tyr Thr
1               5

<210> SEQ ID NO 54
<211> LENGTH: 9
<212> TYPE: PRT
<213> ORGANISM: Artificial
<220> FEATURE:
<223> OTHER INFORMATION: Synthetic peptide

<400> SEQUENCE: 54
```

```
Asn Thr Tyr Gly Asn Asn Pro His Thr
1               5

<210> SEQ ID NO 55
<211> LENGTH: 9
<212> TYPE: PRT
<213> ORGANISM: Artificial
<220> FEATURE:
<223> OTHER INFORMATION: Synthetic peptide

<400> SEQUENCE: 55

His Gln Tyr Tyr Asn Thr Pro Tyr Thr
1               5

<210> SEQ ID NO 56
<211> LENGTH: 8
<212> TYPE: PRT
<213> ORGANISM: Artificial
<220> FEATURE:
<223> OTHER INFORMATION: Synthetic peptide

<400> SEQUENCE: 56

Gln Tyr Tyr Ser Thr Pro Tyr Thr
1               5

<210> SEQ ID NO 57
<211> LENGTH: 9
<212> TYPE: PRT
<213> ORGANISM: Artificial
<220> FEATURE:
<223> OTHER INFORMATION: Synthetic peptide

<400> SEQUENCE: 57

Gln Gln Tyr Tyr Ser Thr Pro Tyr Thr
1               5
```